US00RE48335E

(19) United States
(12) Reissued Patent
Li et al.

(10) Patent Number: US RE48,335 E
(45) Date of Reissued Patent: Dec. 1, 2020

(54) POLYMYXIN DERIVATIVES AS ANTIMICROBIAL COMPOUNDS

(71) Applicant: Monash University, Clayton (AU)

(72) Inventors: Jian Li, Carnegie (AU); Roger Nation, Ivanhoe East (AU); Tony Velkov, Clarinda (AU); Philip Thompson, Northcote (AU); Kade D. Roberts, Flemington (AU)

(73) Assignee: Monash University, Clayton (AU)

(21) Appl. No.: 16/144,967

(22) Filed: Sep. 27, 2018

Related U.S. Patent Documents

Reissue of:
(64) Patent No.: 10,047,126
Issued: Aug. 14, 2018
Appl. No.: 15/301,310
PCT Filed: Apr. 1, 2015
PCT No.: PCT/AU2015/050149
§ 371 (c)(1),
(2) Date: Oct. 17, 2016
PCT Pub. No.: WO2015/149131
PCT Pub. Date: Oct. 8, 2015

(30) Foreign Application Priority Data

Apr. 1, 2014 (AU) ..... 2014901182

(51) Int. Cl.
*C07K 7/62* (2006.01)
*A61K 38/12* (2006.01)
*A61K 38/00* (2006.01)

(52) U.S. Cl.
CPC ..... *C07K 7/62* (2013.01); *A61K 38/12* (2013.01); *A61K 38/00* (2013.01)

(58) Field of Classification Search
CPC ..... C07K 7/62; A61K 38/12; A61K 38/00
See application file for complete search history.

(56) References Cited

U.S. PATENT DOCUMENTS 7,811,790 B2 * 10/2010 Park ..... C12N 15/52 435/183
2006/0004185 A1 1/2006 Leese et al.
2014/0073559 A1 3/2014 Curran et al.
2018/0282374 A1 10/2018 Roberts et al.

FOREIGN PATENT DOCUMENTS

TW 2010/35111 A1 10/2010
WO 2006/045156 A1 5/2006
WO WO 2010/075416 A1 7/2010
WO 2010/130007 A1 11/2010
WO WO 2012/051663 4/2012
WO WO 2012/168820 12/2012
WO 2013/072695 A1 5/2013
WO WO 2015/135976 9/2015

OTHER PUBLICATIONS

Orwa et al, "Isolation and Structural Characterization of Colistin Components," The Journal of Antibiotics, vol. 54, No. 7, pp. 595-599. (Year: 2001).*
First Office Action in Chinese application No. 201580027296.9 dated Mar. 4, 2019.
Magee et al., "Discovery of Dap-3 Polymyxin Analogues for the Treatment of Multidrug-resistant Gram-negative Nosocomial Infections", J Med Chem. (2013) 56(12): 5079-5093.
Kadar et al., "The Renaissance of Polymyxins," *Current Medicinal Chemistry*, 20(30): 3759-3773 (2013).
Kanazawa et al., "Contribution of Each Amino Acid Residue in Polymyxin $B_3$ to Antimicrobial and Lipopolysaccharide Binding Activity," *Chem. Pharm. Bull.*, 57(3): 240-244 (Mar. 2009).
Kimura et al., "Analytical and Preparative Methods for Polymyxin Antibiotics Using High-Performance Liquid Chromatography with a Porous Styrene-Divinylbenzene Copolymer Packing," *Journal of Chromatography*, 206: 563-572 (1981).
Niu et al., "Polymyxin P is the active principle in suppressing phytopathogenic *Erwinia* spp. by the biocontrol rhizobacterium *Paenibacillus polymyxa* M-1," *BMC Microbiology*, 13(137): 1-13 (2013).
Terabe et al., "Separation of Polymyxins and Octapeptins by High-Performance Liquid Chromatography," *Journal of Chromatography*, 173: 313-320 (1979).
Van Den Bossche et al., "Identification of impurities in polymyxin B and colistin bulk sample using liquid chromatography coupled to mass spectrometry," *Talanta*, 83: 1521-1529 (2011).
Velkov et al., "Teaching 'Old' Polymyxins New Tricks: New-Generation Lipopeptides Targeting Gram-Negative 'Superbugs,'" *ACS Chem. Biol.*, 9: 1172-1177 (2014).

* cited by examiner

*Primary Examiner* — Alan D Diamond
(74) *Attorney, Agent, or Firm* — Knobbe, Martens, Olson & Bear LLP

(57) ABSTRACT

The present invention relates to antimicrobial compounds and their uses, and in particular to peptide antibiotics which may be used in the treatment of bacterial infections such as Gram-negative bacterial infections, particularly those caused by multidrug-resistant (MDR) pathogens.

4 Claims, No Drawings

POLYMYXIN DERIVATIVES AS ANTIMICROBIAL COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*STATEMENT OF GOVERNMENT INTEREST*

*This invention was made with government support under R01 AI098771 awarded by the National Institute of Allergy and Infectious Diseases (NIAID), an institute of the National Institutes of Health (NIH). The government has certain rights in the invention.*

CROSS-REFERENCE TO RELATED APPLICATIONS

This application is a U.S. national stage application of the PCT International Application No. PCT/AU2015/050149, filed Apr. 1, 2015 which claims the benefit of foreign priority of Australian application 2014901182, filed on Apr. 1, 2014. The foregoing applications are incorporated herein by reference in their entireties.

FIELD OF THE INVENTION

The present invention relates to antimicrobial compounds and their uses, and in particular to peptide antibiotics which may be used in the treatment of bacterial infections such as Gram-negative bacterial infections, particularly those caused by multidrug-resistant (MDR) pathogens.

BACKGROUND OF THE INVENTION

The world is facing an enormous and growing threat from the emergence of bacteria that are resistant to almost all available antibiotics. Whilst a small number of new antibiotics targeting multidrug-resistant (MDR) Gram-positive bacteria have been approved in the past two decades, there has been a marked decline in the discovery of novel antibiotics for the treatment of Gram-negative bacteria.

Representative genera of Gram-negative bacteria are: Acinetobacter; Actinobacillus; Bartonella; Bordetella; Brucella; Burkholderia; Campylobacter; Cyanobacteria; Enterobacter; Envinia; Escherichia; Francisella; Helicobacter; Hemophilus; Klebsiella; Legionella; Moraxella; Morganella; Neisseria; Pasteurella; Proteus; Providencia; Pseudomonas; Salmonella; Serratia; Shigella; Stenotrophomonas; Treponema; Vibrio; and Yersinia.

The Infectious Diseases Society of America (IDSA) has placed P. aeruginosa, A. baumannii and K. pneumoniae on a 'hit list' of the six top-priority dangerous MDR microorganisms, the so-called 'superbugs', in its recent 'Bad Bugs Need Drugs' campaign. While the recently approved tigecycline is active against a range of clinically important Gram-negative pathogens, including Acinetobacter baumannii, it is reported to not be effective against Pseudomonas aeruginosa. Numerous hospitals worldwide have experienced outbreaks of infections caused by P. aeruginosa, A. baumannii or K. pneumoniae that are resistant to all commercially available antibiotics, except for the last-line therapy polymyxins.

Polymyxins belong to a class of peptides which was discovered more than 60 years ago. They are produced by nonribosomal biosynthetic enzymes from the secondary metabolic pathways in Paenibacillus polymyxa. There are two polymyxins clinically available, colistin (polymyxin E) and polymyxin B. Commercial preparations of polymyxin B and colistin are mixtures of closely related peptides obtained from fermentation (Orwa, J. A., et al. (2001) J. Chromatography A. 912, 369-373; Govaerts, C., et al. (2002) J. Chromatography A. 976, 65-78). The two major components found in polymyxin B preparations are namely polymyxin $B_1$ and $B_2$, whilst commercial preparations of colistin contain two major components labelled with colistin A and B. The structures of these polymyxin B and colistin components are shown below.

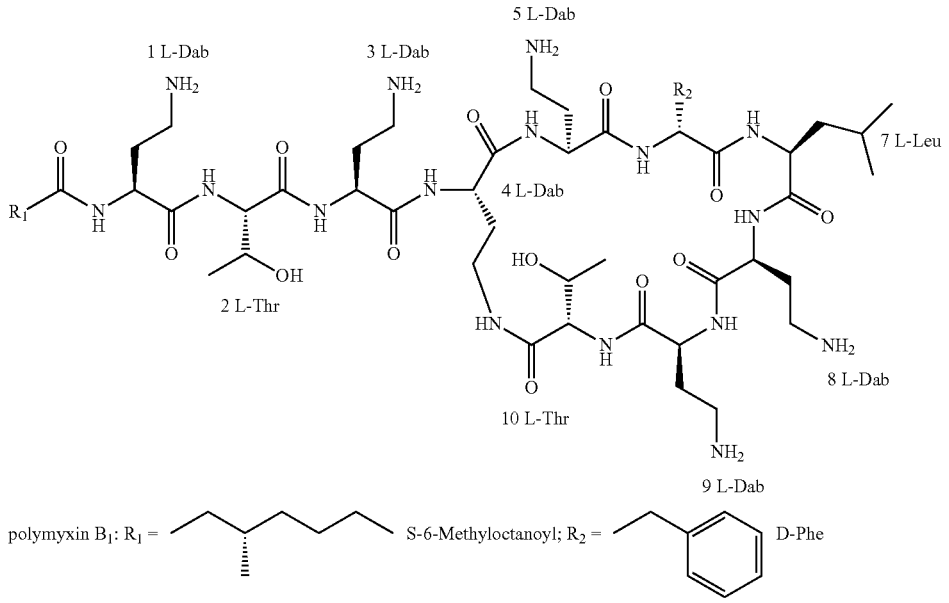

-continued polymyxin $B_2$: $R_1$ = 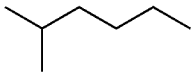 6-Methylheptanoyl; $R_2$ = 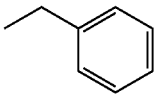 D-Phe colistin A: $R_1$ = 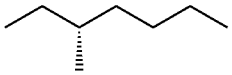 S-6-Methylloctanoyl; $R_2$ = 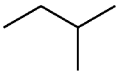 D-Leu colistin B: $R_1$ = 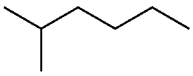 6-Methylheptanoyl; $R_2$ = 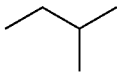 D-Leu Polymyxins are now being used as a last-line class of antibiotics in patients where all other available antibiotics are inactive. Despite the efficacy of polymyxins in treating certain Gram-negative bacterial infections, it has been shown that parenteral administration of colistin (as its inactive prodrug colistin methanesulphonate) and polymyxin B can be potentially nephrotoxic in up to 60% of patients, which limits them from being used more routinely to treat MDR Gram-negative infections. Furthermore, since nephrotoxicity is the major dose-limiting factor for the currently available polymyxins, suboptimal dosing of polymyxins can promote the emergence of polymyxin resistance. Accordingly there exists a need to develop novel polymyxin compounds that provide similar or better efficacy as the clinical available polymyxins but without the nephrotoxic side effects.

SUMMARY OF THE INVENTION

It has now been found that certain polymyxin analogues have reduced nephrotoxic side effects relative to polymyxin B or colistin, whilst retaining or improving their efficacy against Gram-negative bacteria, in particular, MDR Gram-negative bacteria.

Accordingly, in one aspect the present invention provides a method of preventing or treating a multidrug-resistant (MDR) Gram-negative bacterial infection comprising administering a therapeutically effective amount of one or more compounds of the formula (I) or formula (II) to a subject in need thereof:

wherein $R^1$ is selected from —$C(O)C_{1-22}$alkyl, —$C(O)C_{2-22}$alkenyl, —$C(O)C_{5-12}$aryl, —$C(O)C_{1-22}$alkyl$C_{5-12}$aryl, —$C(O)C_{1-22}$alkyl$C_{3-12}$cycloalkyl, —$C(O)C_{5-10}$aryl$C_{2-22}$alkenyl, —$C(O)C_{4-12}$cycloalkyl, —$C(O)C_{3-12}$cycloalkyl$C_{1-22}$alkyl, —$C(O)C_{3-12}$cycloalkyl$C_{2-22}$alkenyl, —$C(S)C_{1-22}$alkyl, —$C(S)C_{2-22}$alkenyl, —$C(S)C_{5-10}$aryl, —$C(S)C_{1-22}$alkyl$C_{5-12}$aryl, —$C(S)C_{1-22}$alkyl$C_{3-12}$cycloalkyl, —$C(S)C_{4-12}$cycloalkyl, —$C(S)C_{5-10}$aryl$C_{1-22}$alkyl, —$C(S)C_{5-10}$aryl$C_{2-22}$alkenyl, —$C(S)C_{3-12}$cycloalkyl$C_{1-22}$alkyl, —$C(S)C_{3-12}$cycloalkyl$C_{2-22}$alkenyl, —$C(NH)C_{1-22}$alkyl, —$C(NH)C_{2-22}$alkenyl, —$C(NH)C_{5-10}$aryl, —$C(NH)C_{1-22}$alkyl$C_{5-12}$aryl, —$C(NH)C_{1-22}$alkyl$C_{3-12}$cycloalkyl, —$C(NH)C_{4-12}$cycloalkyl, —$C(NH)C_{5-10}$aryl$C_{1-22}$alkyl, —$C(NH)C_{5-10}$aryl$C_{2-22}$alkenyl, —$C(NH)C_{3-12}$cycloalkyl$C_{1-22}$alkyl, —$C(NH)C_{3-12}$cycloalkyl$C_{2-22}$alkenyl, —$S(O)_2C_{1-22}$alkyl, —$S(O)_2C_{2-22}$alkenyl, —$S(O)_2C_{5-10}$aryl, —$S(O)_2C_{4-12}$cycloalkyl, —$S(O)_2C_{5-10}$aryl$C_{1-22}$alkyl, —$S(O)_2C_{5-10}$aryl$C_{2-22}$alkenyl, —$S(O)_2C_{3-12}$cycloalkyl$C_{1-22}$alkyl and —$S(O)_2C_{3-12}$cycloalkyl$C_{2-22}$alkenyl, each optionally substituted with one or more $C_{1-2}$alkyl, halo, or trihalo$C_{1-2}$alkyl;

$R^2$ represents a side chain of an amino acid selected from serine or threonine;

$R^3$ represents a side chain of an amino acid selected from leucine, phenylalanine, norleucine, norvaline or t-butylglycine;

$R^4$ represents a side chain of an amino acid selected from alanine, threonine, serine, valine, t-butylglycine, 2-aminobutyric acid or 2-aminoisobutyric acid;

(I)

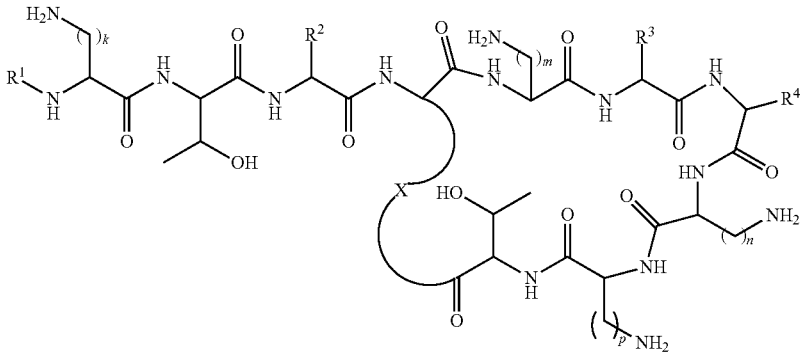

X is a residue of the side chain of an amino acid selected from diaminobutyric acid, diaminopropionic acid, lysine or ornithine; and k, m, n and p are individually selected from 1, 2, or 3; or formula (II):

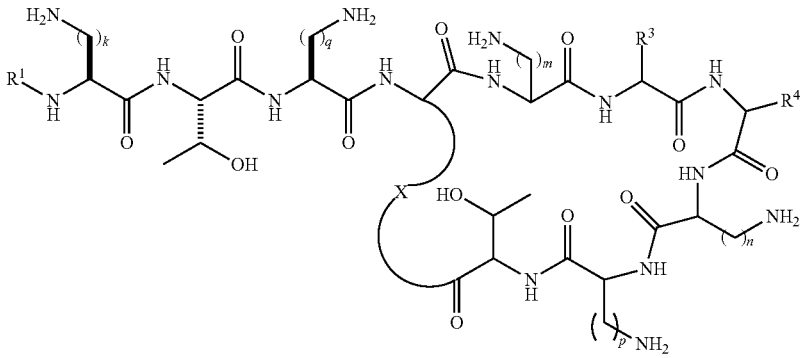

(II)

wherein $R^1$, $R^3$, $R^4$, X, k, m, n and p are as defined above for formula (I); and q is 1, 2 or 3; or pharmaceutically acceptable salts thereof.

In another aspect, the present invention provides the use of one or more compounds of formula (I) and/or formula (II) as hereinbefore described, or pharmaceutically acceptable salts thereof, in the manufacture of a medicament for the prevention or treatment of a multidrug-resistant (MDR) Gram-negative bacterial infection.

In another aspect, the present invention provides one or more compounds of formula (I) and/or formula (II) as hereinbefore described, or pharmaceutically acceptable salts thereof, for use in the prevention or treatment of a multidrug-resistant (MDR) Gram-negative bacterial infection.

In another aspect the present invention provides compound of the formula (Ia):

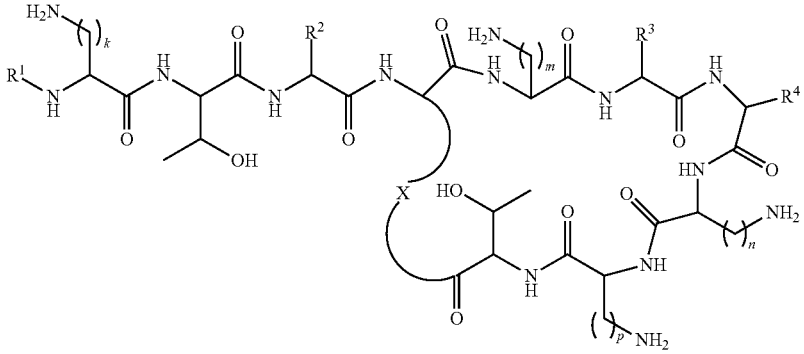

(Ia)

wherein $R^1$ is selected from —C(O)$C_{1-22}$alkyl, —C(O)$C_{2-22}$alkenyl, —C(O)$C_{5-12}$aryl, —C(O)$C_{1-22}$alkyl$C_{5-12}$aryl, —C(O)$C_{1-22}$alkyl$C_{3-12}$cycloalkyl, —C(O)$C_{5-10}$aryl$C_{2-22}$alkenyl, —C(O)$C_{4-12}$cycloalkyl, —C(O)$C_{3-12}$cycloalkyl$C_{1-22}$alkyl, —C(O)$C_{3-12}$cycloalkyl$C_{2-22}$alkenyl, —C(S)$C_{1-22}$alkyl, —C(S)$C_{2-22}$alkenyl, —C(S)$C_{5-10}$aryl, —C(S)$C_{1-22}$alkyl$C_{5-12}$aryl, —C(S)$C_{1-22}$alkyl$C_{3-12}$cycloalkyl, —C(S)$C_{4-12}$cycloalkyl, —C(S)$C_{5-10}$aryl$C_{1-22}$alkyl, —C(S)$C_{5-10}$aryl$C_{2-22}$alkenyl, —C(S)$C_{3-12}$cycloalkyl$C_{1-22}$alkyl, —C(S)$C_{3-12}$cycloalkyl$C_{2-22}$alkenyl, —C(NH)$C_{1-22}$alkyl, —C(NH)$C_{2-22}$alkenyl, —C(NH)$C_{5-10}$aryl, —C(NH)$C_{1-22}$alkyl$C_{5-12}$aryl, —C(NH)$C_{1-22}$alkyl$C_{3-12}$cycloalkyl, —C(NH)$C_{4-12}$cycloalkyl, —C(NH)$C_{5-10}$aryl$C_{1-22}$alkyl, —C(NH)$C_{5-10}$aryl$C_{2-12}$alkenyl, —C(NH)$C_{3-12}$cycloalkyl$C_{1-22}$alkyl, —C(NH)$C_{3-12}$cycloalkyl$C_{2-22}$alkenyl, —S(O)$_2$$C_{1-22}$alkyl, —S(O)$_2$$C_{2-22}$alkenyl, —S(O)$_2$$C_{5-10}$aryl, —S(O)$_2$$C_{4-12}$cycloalkyl, —S(O)$_2$$C_{5-10}$aryl$C_{1-22}$alkyl, —S(O)$_2$$C_{5-10}$aryl$C_{2-22}$alkenyl, —S(O)$_2$$C_{3-12}$cycloalkyl$C_{1-22}$alkyl and —S(O)$_2$$C_{3-12}$cycloalkyl$C_{2-22}$alkenyl, each optionally substituted with one or more $C_{1-2}$alkyl, halo, or trihalo$C_{1-2}$alkyl;

$R^2$ represents a side chain of an amino acid selected from serine or threonine;

$R^3$ represents a side chain of an amino acid selected from leucine, phenylalanine, norleucine, norvaline or t-butylglycine;

$R^4$ represents a side chain of an amino acid selected from alanine, threonine, serine, valine, t-butylglycine, 2-aminobutyric acid or 2-aminoisobutyric acid;

X is a residue of the side chain of an amino acid selected from diaminobutyric acid, diaminopropionic acid, lysine or ornithine; and k, m, n and p are individually selected from 1, 2, or 3;

with the proviso that when $R^3$ is the side chain residue of leucine or phenylalanine, $R^4$ is the side chain residue of threonine and k, m, n and p are 2, $R^1$ is not S-6-methyloctanoyl or 6-methylheptanoyl; or pharmaceutically acceptable salts thereof In a further aspect, the present invention provides a compound of the formula (IIa):

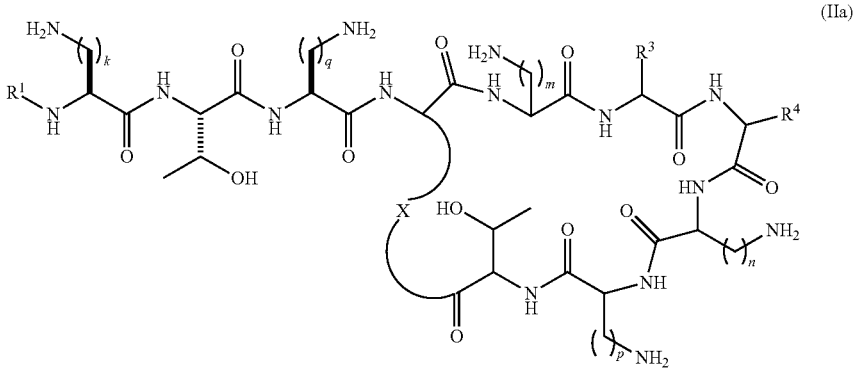

(IIa)

wherein $R^1$ is selected from —C(O)$C_{1-22}$alkyl, —C(O)$C_{2-22}$alkenyl, —C(O)$C_{5-12}$aryl, —C(O)$C_{1-22}$alkyl$C_{5-12}$aryl, —C(O)$C_{1-22}$alkyl$C_{3-12}$cycloalkyl, —C(O)$C_{5-10}$aryl$C_{2-22}$alkenyl, —C(O)$C_{4-12}$cycloalkyl, —C(O)$C_{3-12}$cycloalkyl$C_{1-22}$alkyl, —C(O)$C_{3-12}$cycloalkyl$C_{2-22}$alkenyl, —C(S)$C_{1-22}$alkyl, —C(S)$C_{2-22}$alkenyl, —C(S)$C_{5-10}$aryl, —C(S)$C_{1-22}$alkyl$C_{5-12}$aryl, —C(S)$C_{1-22}$alkyl$C_{3-12}$cycloalkyl, —C(S)$C_{4-12}$cycloalkyl, —C(S)$C_{5-10}$aryl$C_{1-22}$alkyl, —C(S)$C_{5-10}$aryl$C_{2-22}$alkenyl, —C(S)$C_{3-12}$cycloalkyl$C_{1-22}$alkyl, —C(S)$C_{3-12}$cycloalkyl$C_{2-22}$alkenyl, —C(NH)$C_{1-22}$alkyl, —C(NH)$C_{2-22}$alkenyl, —C(NH)$C_{5-10}$aryl, —C(NH)$C_{1-22}$alkyl$C_{5-12}$aryl, —C(NH)$C_{1-22}$alkyl$C_{3-12}$cycloalkyl, —C(NH)$C_{4-12}$cycloalkyl, —C(NH)$C_{5-10}$aryl$C_{1-22}$alkyl, —C(NH)$C_{5-10}$aryl$C_{2-22}$alkenyl, —C(NH)$C_{3-12}$cycloalkyl$C_{1-22}$alkyl, —C(NH)$C_{3-12}$cycloalkyl$C_{2-22}$alkenyl, —S(O)$_2$$C_{1-22}$alkyl, —S(O)$_2$$C_{2-22}$alkenyl, —S(O)$_2$$C_{5-10}$aryl, —S(O)$_2$$C_{4-12}$cycloalkyl, —S(O)$_2$$C_{5-10}$aryl$C_{1-22}$alkyl, —S(O)$_2$$C_{5-10}$aryl$C_{2-22}$alkenyl, —S(O)$_2$$C_{3-12}$cycloalkyl$C_{1-22}$alkyl and —S(O)$_2$$C_{3-12}$cycloalkyl$C_{2-22}$alkenyl, each optionally substituted with one or more $C_{1-2}$alkyl, halo, or trihalo$C_{1-2}$alkyl;

$R^3$ represents a side chain of an amino acid selected from leucine, phenylalanine, norleucine, norvaline or t-butylglycine;

$R^4$ represents a side chain of an amino acid selected from alanine, threonine, serine, valine, t-butylglycine, 2-aminobutyric acid or 2-aminoisobutyric acid;

X is a residue of the side chain of an amino acid selected from diaminobutyric acid, diaminopropionic acid, lysine or ornithine; and k, m, n, p and q are individually selected from 1, 2, or 3;

with the proviso that when $R^3$ is the side chain residue of leucine, $R^4$ is the side chain residue of threonine and k, m, n, p and q are 2, $R^1$ is not S-6-methyloctanoyl or 6-methylheptanoyl, or pharmaceutically acceptable salts thereof.

In another aspect the invention provides a pharmaceutical composition comprising a therapeutically effective amount of one or more compounds as hereinbefore defined, or pharmaceutically acceptable salts thereof, together with at least one pharmaceutically acceptable carrier or diluent.

In another aspect the invention provides a method of preventing or treating a Gram-negative bacterial infection comprising the step of administering a therapeutically effective amount of one or more compounds of the formula (Ia) and/or (IIa) as hereinbefore described, or pharmaceutically acceptable salts thereof, to a subject in need thereof.

In another aspect the invention provides the use of one or more compounds of the formula (Ia) and/or (IIa) as hereinbefore described, or pharmaceutically acceptable salts thereof, in the manufacture of a medicament for the prevention or treatment of a Gram-negative bacterial infection.

In another aspect the invention provides one or more compounds of the formula (Ia) and/or (IIa) as hereinbefore described, or pharmaceutically acceptable salts thereof, for use in the prevention or treatment of a Gram-negative bacterial infection.

These and other aspects of the present invention will become more apparent to the skilled addressee upon reading the following detailed description in connection with the accompanying examples and claims.

DETAILED DESCRIPTION OF THE INVENTION

The initial cellular target of polymyxins in Gram-negative bacteria is the lipopolysaccharide (LPS) component of the outer membrane (OM). It is believed that the LPS target is generally conserved across most, if not all, Gram-negative bacteria.

In general, LPS is composed of three domains, a conserved inner core 2-keto-3-deoxyoctanoic acid bound to lipid A and a variable O-antigen composed of repeating units of various polysaccharides. The consensus structure of lipid A consists of a β-1'-6-linked D-glucosamine disaccharide that is phosphorylated at the 1- and 4'-positions. An example of the structure of lipid A from P. aeruginosa is shown below:

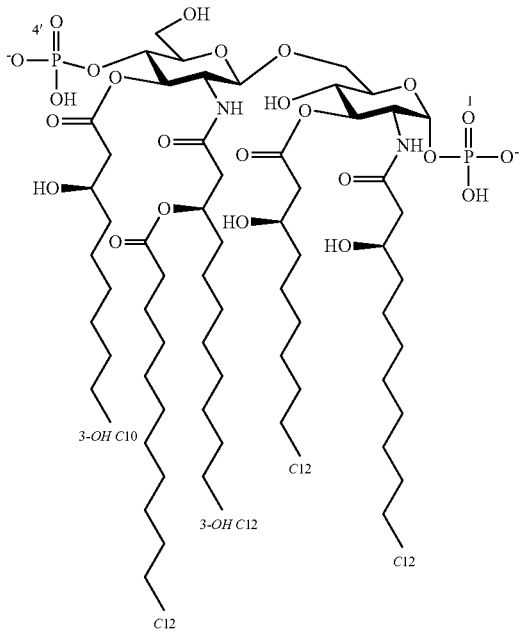

Lipid A usually contains six acyl chains. Four β-hydroxy acyl chains (usually $C_{10}$ to $C_{14}$ in length) are attached directly to the glucosamine sugars, while a secondary acyl chain is often attached to the β-hydroxy group on each of two of the chains. Lipid A acts as a hydrophobic anchor with the tight packing of the fatty acyl chains helping to stabilise the overall outer membrane structure.

It is believed that there is an initial polar interaction between the cationic polymyxin peptide (particularly the charged α,γ-diaminobutyric acid (Dab) residues) and the lipid A component of LPS in the outer membrane, thereby displacing divalent cations ($Ca^{2+}$ and $Mg^{2+}$) from the negatively charged phosphate groups of lipid A. This initial interaction is followed by uptake across the outer membrane and interaction with the cytoplasmic membrane.

Polymyxin B and colistin (polymyxin E) first became available for clinical use as antibiotics in the 1950s. Shortly after, their use fell out of favour because of concerns about nephrotoxic side effects. These observed nephrotoxic side effects for colistin resulted in the peptide rarely being used as an antibiotic during the period of 1980-2000. More recently it has found use again as a last-line antibiotic, predominantly due to necessity, in patients where all other antibiotics are found to be ineffective. Furthermore, since nephrotoxicity is the major dose-limiting factor for the current polymyxins, compounds having an improved nephrotoxicity profile would allow higher doses to be administered to more effectively treat infections and suppress the emergence of polymyxin resistance.

It has now surprisingly been found that the compounds of the present invention are effective against Gram-negative bacteria whilst displaying an improved nephrotoxicity profile relative to polymyxin B or colistin. The present inventors have discovered that certain amino acid residues at three key locations within the polymyxin structure, in combination with specific N-terminal fatty acyl groups, can significantly reduce the level of nephrotoxicity of the compound whilst maintaining or improving the compound's antibacterial efficacy.

In this specification a number of terms are used which are well known to a skilled addressee. Nevertheless, for the purposes of clarity a number of terms will be defined. As used herein, the term "alkyl", used either alone or in compound words, denotes straight chain or branched alkyl. Preferably the alkyl group is a straight chain alkyl group. Prefixes such as "$C_{1-22}$" are used to denote the number of carbon atoms within the alkyl group (from 1 to 22 in this case). Examples of straight chain and branched alkyl include methyl, ethyl, n-propyl, isopropyl, n-butyl, sec-butyl, t-butyl, n-pentyl, hexyl, heptyl, 5-methylheptyl, 5-methylhexyl, octyl, nonyl, decyl, undecyl, dodecyl and docosyl ($C_{22}$).

As used herein, the term "alkenyl", used either alone or in compound words, denotes straight chain or branched hydrocarbon residues containing at least one carbon to carbon double bond including ethylenically mono-, di- or polyunsaturated alkyl groups as previously defined. Preferably the alkenyl group is a straight chain alkenyl group. Prefixes such as "$C_{2-22}$" are used to denote the number of carbon atoms within the alkenyl group (from 2 to 22 in this case). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1,4-pentadienyl, 1,3-hexadienyl, 1,4-hexadienyl and 5-docosenyl ($C_{22}$).

As used herein, the term "cycloalkyl", used either alone or in compound words, denotes a cyclic alkyl group. Prefixes such as "$C_{3-12}$" are used to denote the number of carbon atoms within the cyclic portion of the alkyl group (from 3 to 12 in this case). Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and cyclododecyl.

As used herein, the term "aryl" denotes any single- or polynuclear, conjugated or fused residues of aromatic hydrocarbon ring systems. Prefixes such as "$C_{6-16}$" are used to denote the number of carbon atoms within the cyclic portion of the aryl group (from 6 to 16 in this case). Examples of aryl include phenyl (single nuclear), naphthyl (fused polynuclear), biphenyl (conjugated polynuclear) and tetrahydronaphthyl (fused polynuclear).

The term "halo" used herein refers to fluoro, chloro, bromo or iodo.

As used herein, reference to an amino acid "side chain" takes its standard meaning in the art. Examples of side chains of amino acids are shown below:

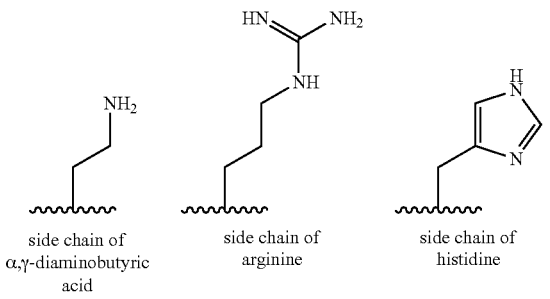

-continued

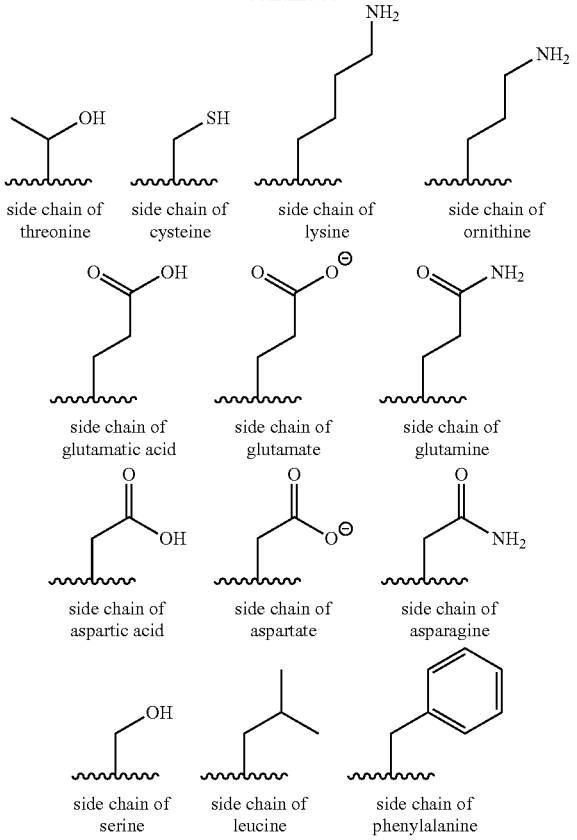

As used herein, non-naturally occurring amino acids include any compound with both amino and carboxyl functionality, derivatives thereof, or derivatives of a naturally occurring amino acid. These amino acids form part of the peptide chain through bonding via their amino and carboxyl groups. Alternatively, these derivatives may bond with other natural or non-naturally occurring amino acids to form a non-peptidyl linkage.

In addition to the negatively charged side chains shown above, it will be appreciated that a number of the side chains may also be protonated and so become positively charged, such as the side chain of lysine. The present invention contemplates within its scope these protonated side chains as well.

It will be understood that the compounds of the present invention may exist in one or more stereoisomeric forms (e.g. diastereomers). The present invention includes within its scope all of these stereoisomeric forms either isolated (in, for example, enantiomeric isolation), or in combination (including racemic mixtures and diastereomic mixtures). The present invention contemplates the use of amino acids in both L and D forms, including the use of amino acids independently selected from L and D forms, for example, where the peptide comprises two Dab residues, each Dab residue may have the same, or opposite, absolute stereochemistry. Unless stated otherwise, the amino acid is taken to be in the L-configuration.

The invention thus also relates to compounds in substantially pure stereoisomeric form with respect to the asymmetric centres of the amino acid residues, e.g., greater than about 90% de, such as about 95% to 97% de, or greater than 99% de, as well as mixtures, including racemic mixtures, thereof. Such diastereomers may be prepared by asymmetric synthesis, for example, using chiral intermediates, or mixtures may be resolved by conventional methods, e.g., chromatography, or use of a resolving agent.

In some preferred embodiments of the invention, and with reference to the general formulae (Ia) and (IIa), one or more of the following preferred embodiments apply:

a) $R^1$ is selected from —C(O)$C_{1-22}$alkyl, —C(O)$C_{2-22}$alkenyl, —C(O)$C_{5-12}$aryl, —C(O)$C_{1-22}$alkyl$C_{5-12}$aryl, —C(O)$C_{1-22}$alkyl$C_{3-12}$cycloalkyl, —C(O)$C_{5-10}$aryl$C_{2-22}$alkenyl, —C(O)$C_{4-12}$cycloalkyl, —C(O)$C_{3-12}$cycloalkyl$C_{1-22}$alkyl, —C(O)$C_{3-12}$cycloalkyl$C_{2-22}$alkenyl, —C(S)$C_{1-22}$alkyl, —C(S)$C_{2-22}$alkenyl, —C(S)$C_{5-10}$aryl, —C(S)$C_{1-22}$alkyl$C_{5-12}$aryl, —C(S)$C_{1-22}$alkyl$C_{3-12}$cycloalkyl, —C(S)$C_{4-12}$cycloalkyl, —C(S)$C_{5-10}$aryl$C_{1-22}$alkyl, —C(S)$C_{5-10}$aryl$C_{2-22}$alkenyl, —C(S)$C_{3-12}$cycloalkyl$C_{1-22}$alkyl, —C(S)$C_{3-12}$cycloalkyl$C_{2-22}$alkenyl, —C(NH)$C_{1-22}$alkyl, —C(NH)$C_{2-22}$alkenyl, —C(NH)$C_{5-10}$aryl, —C(NH)$C_{1-22}$alkyl$C_{5-12}$aryl, —C(NH)$C_{1-22}$alkyl$C_{3-12}$cycloalkyl, —C(NH)$C_{4-12}$cycloalkyl, —C(NH)$C_{5-10}$aryl$C_{1-22}$alkyl, —C(NH)$C_{5-10}$aryl$C_{2-22}$alkenyl, —C(NH)$C_{3-12}$cycloalkyl$C_{1-22}$alkyl, —C(NH)$C_{3-12}$cycloalkyl$C_{2-22}$alkenyl, —S(O)$_2C_{1-22}$alkyl, —S(O)$_2C_{2-22}$alkenyl, —S(O)$_2C_{5-10}$aryl, —S(O)$_2C_{4-12}$cycloalkyl, —S(O)$_2C_{5-10}$aryl$C_{1-22}$alkyl, —S(O)$_2C_{5-10}$aryl$C_{2-22}$alkenyl, —S(O)$_2C_{3-12}$cycloalkyl$C_{1-22}$alkyl and —S(O)$_2C_{3-12}$cycloalkyl$C_{2-22}$alkenyl, each optionally substituted with one or more $C_{1-2}$alkyl, halo, or trihalo$C_{1-2}$alkyl.

b) $R^1$ is selected from hexanoyl, hepatanoyl, octanoyl, nonanoyl, decanoyl, dodecanoyl, S,R-6-methyloctanoyl (racemic mixture), R-6-methyloctanoyl, 7-methyl octanoyl, S-5-methyl heptanoyl, R-5-methyl heptanoyl, S,R-5-methyl heptanoyl (racemic mixture), 4-biphenylcarboxyl, 4-trifluoromethylbenzoyl, 4-ethylbenzoyl, 3,4-dichlorobenzoyl, 4-chlorobenzoyl, 3-chlorobenzoyl, pentafluorobenzoyl, 4-methylbenzoyl, 4-ethylphenylacetyl, phenylacetyl, 4-methylphenylacetyl, 4-trifluoromethylphenylacetyl, pentafluorophenyl acetyl, 3,4-dichlorophenylacetyl, 4-chlorophenyl acetyl, 3-chlorophenyl acetyl, 2-chlorobenzoyl, 2-fluorobenzoyl, 2-methyl benzoyl, 2-chlorophenylacetyl, 2-methylphenyl acetyl, 2-fluorophenylacetyl, 2,3-dichlorobenzoyl, 2,3-dimethylbenzoyl, 2,4-dichlorophenylacetyl, 2,4-dichlorobenzoyl, 2,4-dimethylbenzoyl, 2-chloro-4-methylbenzoyl, 2-chloro-4-trifluoromethylbenzoyl, 3-fluorobenzoyl, 3-methylbenzoyl, 3-trifuoromethylbenzoyl, 3,4-dimethylbenzoyl, 3-fluoro-4-methylbenzoyl, 4-chloro-3-methylbenzoyl, 3,4-dimethylphenylacetyl, 3-chloro-4-methylbenzoyl, 4-chloro-3-fluorobenzoyl, 3-fluoro-4-trifluoromethylbenzoyl, 3-chloro-4-fluorobenzoyl, 4-methyl-3-trifluoromethylbenzoyl, 3-methyl-4-trifluoromethylbenzoyl, 3-methyl-5-trifluoromethylbenzoyl, 3,5-dimethylbenzoyl, 3,5-dichlorobenzoyl, 3,5-bis(trifluoromethyl) benzoyl, 3-fluoro-5-trifluoromethylbenzoyl, 3-chloro-5-methylbenzoyl, 3-chloro-5-fluorobenzoyl, benzoyl, 2,4,6-tri methylbenzoyl, 2,4,6-tri chlorobenzoyl, 2-chloro-4-fluorobenzoyl, 4-chloro-2-fluorobenzoyl, 3,4,5-trifluoromethylbenzoyl, 4-chloro-2-trifluoromethylbenzoyl, 2-fluoro-4-trifluoromethylbenzoyl, 3-biphenylcarboxyl, 4-chlorobiphenyl-4-carboxyl, 3-phenylproponyl, 4-phenylbutanoyl, 2,4-di chlorophenyl sulfonyl, 4-chloro-3-tri fluoromethyl benzoyl, 4-isopropylbenzoyl, 4-chloro-3-fluorobenzoyl, 3-chloro-4-trifluoromethylbenzoyl.

c) $R^1$ is selected from hexanoyl, hepatanoyl, octanoyl, nonanoyl, decanoyl, dodecanoyl, S,R-6-methyloctanoyl (racemic mixture), R-6-methyloctanoyl, 7-methyl octanoyl, S-5-methylheptanoyl, R-5-methylheptanoyl, S,R-5-methylheptanoyl (racemic mixture), 4-biphenylcarboxyl, 4-trifluoromethylbenzoyl, 4-ethylbenzoyl, 3,4-dichlorobenzoyl, 4-chlorobenzoyl, 3-chlorobenzoyl, pentafluorobenzoyl, 4-methylbenzoyl, 4-ethylphenylacetyl, phenylacetyl, 4-methylphenylacetyl, 4-trifluoromethylphenylacetyl, pentafluorophenyl acetyl, 3,4-dichlorophenylacetyl, 4-chlorophenyl acetyl, 3-chlorophenyl acetyl, 2-chlorobenzoyl, 2-fluorobenzoyl, 2-methylbenzoyl, 2-chlorophenyl acetyl, 2-fluorophenylacetyl, 2-methylphenylacetyl, 2,3-dichlorobenzoyl, 2,3-dimethylbenzoyl, 2,4-dichlorophenylacetyl, 2,4-dichlorobenzoyl, 2,4-dimethylbenzoyl, 2-chloro-4-methylbenzoyl, 2-chloro-4-trifluoromethylbenzoyl, 3-fluorobenzoyl, 3-methylbenzoyl, 3-trifuoromethylbenzoyl, 3,4-dimethylbenzoyl, 3-fluoro-4-methylbenzoyl, 4-chloro-3-methylbenzoyl, 3,4-dimethylphenyl acetyl, 3-chloro-4-methylbenzoyl, 4-chloro-3-fluorobenzoyl, 3-fluoro-4-trifluoromethylbenzoyl, 3-chloro-4-fluorobenzoyl, 4-methyl-3-trifluoromethylbenzoyl, 3-methyl-4-trifluoromethylbenzoyl, 3-methyl-5-trifluoromethylbenzoyl, 3,5-dimethylbenzoyl, 3,5-dichlorobenzoyl, 3,5-bis(trifluoromethyl) benzoyl, 3-fluoro-5-trifluoromethylbenzoyl, 3-chloro-5-methylbenzoyl, 3-chloro-5-fluorobenzoyl, 2,4,6-trimethylbenzoyl, 2,4,6-tri chlorobenzoyl, 2-chloro-4-fluorobenzoyl, 4-chloro-2-fluorobenzoyl, 3,4,5-trifluoromethylbenzoyl, 4-chloro-2-trifluoromethylbenzoyl, 2-fluoro-4-trifluoromethylbenzoyl, 3-biphenylcarboxyl, 4-chloro-biphenyl-4-carboxyl, 3-phenylproponyl, 4-phenylbutanoyl, 2,4-di chlorophenyl sulfonyl, 4-chloro-3-trifluoromethylbenzoyl, 4-isopropylbenzoyl, 4-chloro-3-fluorobenzoyl, 3-chloro-4-trifluoromethylbenzoyl.

d) $R^1$ is selected from hexanoyl, hepatanoyl, octanoyl, nonanoyl, decanoyl, dodecanoyl, S,R-6-methyloctanoyl (racemic mixture), R-6-methyloctanoyl, 7-methyl octanoyl, S-5-methylheptanoyl, R-5-methylheptanoyl, S,R-5-methylheptanoyl (racemic mixture), 4-biphenylcarboxyl, 4-trifluoromethylbenzoyl, 4-ethylbenzoyl, 3,4-di chlorobenzoyl, 4-chlorobenzoyl, 3-chlorobenzoyl, pentafluorobenzoyl, 4-methylbenzoyl, 4-ethylphenyl acetyl, phenylacetyl, 4-methylphenyl acetyl, 4-trifluoromethyl phenyl acetyl, pentafluorophenylacetyl, 3,4-dichlorophenylacetyl, 4-chlorophenylacetyl and 3-chlorophenylacetyl.

e) $R^2$ represents a side chain of an amino acid selected from serine or threonine.

f) $R^3$ represents a side chain of an amino acid selected from leucine, phenylalanine, norleucine, norvaline or t-butylglycine.

g) $R^4$ represents a side chain of an amino acid selected from alanine, threonine, serine, valine, t-butylglycine, 2-aminobutyric acid or 2-aminoisobutyric acid.

h) $R^4$ represents a side chain of an amino acid selected from alanine, threonine, serine, 2-aminobutyric acid, or 2-aminoisobutyric acid.

i) X is a residue of the side chain of an amino acid selected from diaminobutyric acid, diaminopropionic acid, lysine or ornithine.

j) X is a residue of the side chain of diaminobutyric acid.

k) m, n and p are each 2

In a preferred embodiment X is the side chain residue of diaminobutyric acid and m, n and p are 2.

Accordingly, in a further embodiment, the present invention provides compounds of the formula (Ia) represented by the formula (Ib):

(Ib)

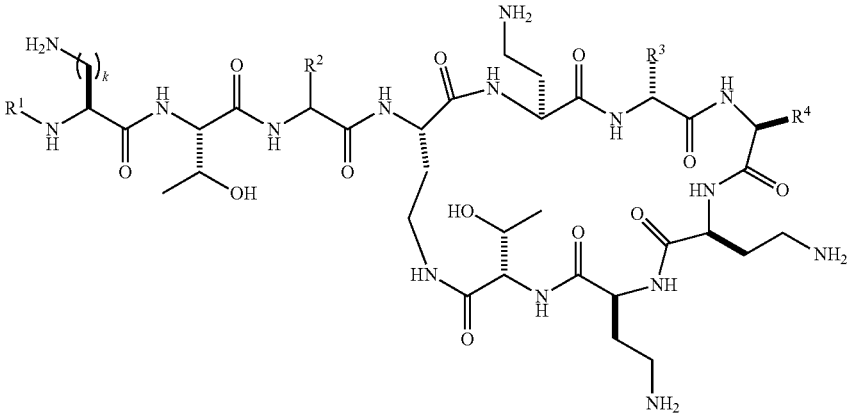

wherein $R^1$ is selected from hexanoyl, hepatanoyl, octanoyl, nonanoyl, decanoyl, dodecanoyl, S,R-6-methyloctanoyl (racemic mixture), R-6-methyloctanoyl, 7-methyloctanoyl, S-5-methylheptanoyl, R-5-methylheptanoyl, S,R-5-methylheptanoyl (racemic mixture), 4-biphenylcarboxyl, 4-trifluoromethylbenzoyl, 4-ethylbenzoyl, 3,4-dichlorobenzoyl, 4-chlorobenzoyl, 3-chlorobenzoyl, pentafluorobenzoyl, 4-methylbenzoyl, 4-ethylphenyl acetyl, phenyl acetyl, 4-methylphenyl acetyl, 4-trifluoromethylphenyl acetyl, pentafluorophenyl acetyl, 3,4-dichlorophenylacetyl, 4-chlorophenyl acetyl, 3-chlorophenyl acetyl, 2-chlorobenzoyl, 2-fluorobenzoyl, 2-methylbenzoyl, 2-chlorophenyl acetyl, 2-fluorophenylacetyl, 2-methylphenylacetyl, 2,3-dichlorobenzoyl, 2,3-dimethylbenzoyl, 2,4-dichlorophenylacetyl, 2,4-dichlorobenzoyl, 2,4-dimethylbenzoyl, 2-chloro-4-methylbenzoyl, 2-chloro-4-trifluoromethylbenzoyl, 3-fluorobenzoyl, 3-methylbenzoyl, 3-trifuoromethylbenzoyl, 3,4-dimethylbenzoyl, 3-fluoro-4-methylbenzoyl, 4-chloro-3-methylbenzoyl, 3,4-dimethylphenyl acetyl, 3-chloro-4-methylbenzoyl, 4-chloro-3-fluorobenzoyl, 3-fluoro-4-trifluoromethylbenzoyl, 3-chloro-4-fluorobenzoyl, 4-methyl-3-trifluoromethylbenzoyl, 3-methyl-4-trifluoromethylbenzoyl, 3-methyl-5-trifluoromethylbenzoyl, 3,5-dimethylbenzoyl, 3,5-dichlorobenzoyl, 3,5-bis(trifluoromethyl) benzoyl, 3-fluoro-5-trifluoromethylbenzoyl, 3-chloro-5-methylbenzoyl, 3-chloro-5-fluorobenzoyl, 2,4,6-trimethylbenzoyl, 2,4,6-tri chlorobenzoyl, 2-chloro-4-fluorobenzoyl, 4-chloro-2-fluorobenzoyl, 3,4,5-trifluoromethylbenzoyl, 4-chloro-2-trifluoromethylbenzoyl, 2-fluoro-4-trifluoromethylbenzoyl, 3-biphenylcarboxyl, 4-chloro-biphenyl-4-carboxyl, 3-phenylproponyl, 4-phenylbutanoyl, 2,4-di chlorophenyl sulfonyl, 4-chloro-3-trifluoromethylbenzoyl, 4-isopropylbenzoyl, 4-chloro-3-fluorobenzoyl, 3-chloro-4-trifluoromethylbenzoyl;

$R^2$ represents a side chain of an amino acid selected from serine or threonine;

$R^3$ represents a side chain of an amino acid selected from leucine, phenylalanine, norleucine, norvaline or t-butylglycine;

$R^4$ represents a side chain of an amino acid selected from alanine, threonine, serine, valine, t-butylglycine, 2-aminobutyric acid or 2-aminoisobutyric acid; and k is 1, 2 or 3; or pharmaceutically acceptable salts thereof.

In a further embodiment the present invention provides compounds of the formula (IIa) represented by the formula (IIb):

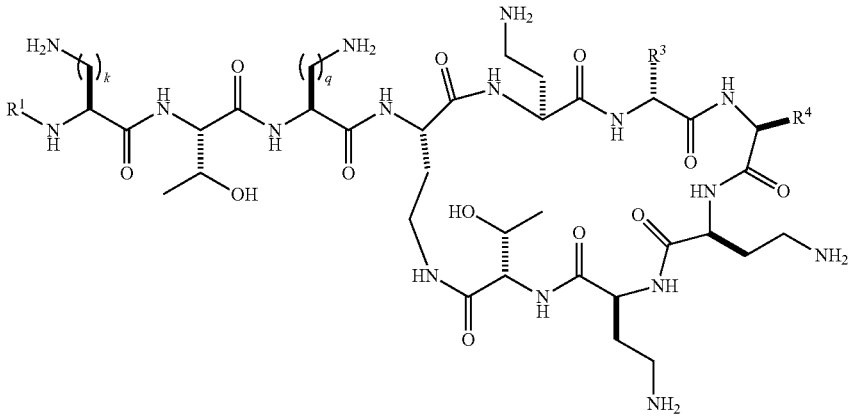

(IIb)

wherein $R^1$ is selected from hexanoyl, hepatanoyl, octanoyl, nonanoyl, decanoyl, dodecanoyl, S,R-6-methyloctanoyl (racemic mixture), R-6-methyloctanoyl, 7-methyloctanoyl, S-5-methylheptanoyl, R-5-methylheptanoyl, S,R-5-methylheptanoyl (racemic mixture), 4-biphenylcarboxyl, 4-trifluoromethylbenzoyl, 4-ethylbenzoyl, 3,4-dichlorobenzoyl, 4-chlorobenzoyl, 3-chlorobenzoyl, pentafluorobenzoyl, 4-methylbenzoyl, 4-ethylphenyl acetyl, phenyl acetyl, 4-methylphenyl acetyl, 4-trifluoromethylphenyl acetyl, pentafluorophenyl acetyl, 3,4-dichlorophenylacetyl, 4-chlorophenyl acetyl, 3-chlorophenyl acetyl, 2-chlorobenzoyl, 2-fluorobenzoyl, 2-methylbenzoyl, 2-chlorophenyl acetyl, 2-fluorophenylacetyl, 2-methylphenylacetyl, 2,3-dichlorobenzoyl, 2,3-dimethylbenzoyl, 2,4-dichlorophenylacetyl, 2,4-dichlorobenzoyl, 2,4-dimethylbenzoyl, 2-chloro-4-methylbenzoyl, 2-chloro-4-trifluoromethylbenzoyl, 3-fluorobenzoyl, 3-methylbenzoyl, 3-trifuoromethylbenzoyl, 3,4-dimethylbenzoyl, 3-fluoro-4-methylbenzoyl, 4-chloro-3-methylbenzoyl, 3,4-dimethylphenyl acetyl, 3-chloro-4-methylbenzoyl, 4-chloro-3-fluorobenzoyl, 3-fluoro-4-trifluoromethylbenzoyl, 3-chloro-4-fluorobenzoyl, 4-methyl-3-trifluoromethylbenzoyl, 3-methyl-4-trifluoromethylbenzoyl, 3-methyl-5-trifluoromethylbenzoyl, 3,5-dimethylbenzoyl, 3,5-dichlorobenzoyl, 3,5-bis(trifluoromethyl)benzoyl, 3-fluoro-5-trifluoromethylbenzoyl, 3-chloro-5-methylbenzoyl, 3-chloro-5-fluorobenzoyl, 2,4,6-trimethylbenzoyl, 2,4,6-tri chlorobenzoyl, 2-chloro-4-fluorobenzoyl, 4-chloro-2-fluorobenzoyl, 3,4,5-trifluoromethylbenzoyl, 4-chloro-2-trifluoromethylbenzoyl, 2-fluoro-4-trifluoromethylbenzoyl, 3-biphenylcarboxyl, 4-chloro-biphenyl-4-carboxyl, 3-phenylproponyl, 4-phenylbutanoyl, 2,4-dichlorophenylsulfonyl, 4-chloro-3-trifluoromethylbenzoyl, 4-isopropylbenzoyl, 4-chloro-3-fluorobenzoyl, 3-chloro-4-trifluoromethylbenzoyl;

$R^3$ represents a side chain of an amino acid selected from leucine, phenylalanine, norleucine, norvaline or t-butylglycine;

$R^4$ represents a side chain of an amino acid selected from alanine, threonine, serine, valine, t-butylglycine, 2-aminobutyric acid or 2-aminoisobutyric acid; and k and q are individually selected from 1, 2, or 3; or pharmaceutically acceptable salts thereof.

In another embodiment compounds of the formula (Ia) are selected from those compounds listed in Table 1.

TABLE 1

Compounds of formula (Ia):

(Ia)

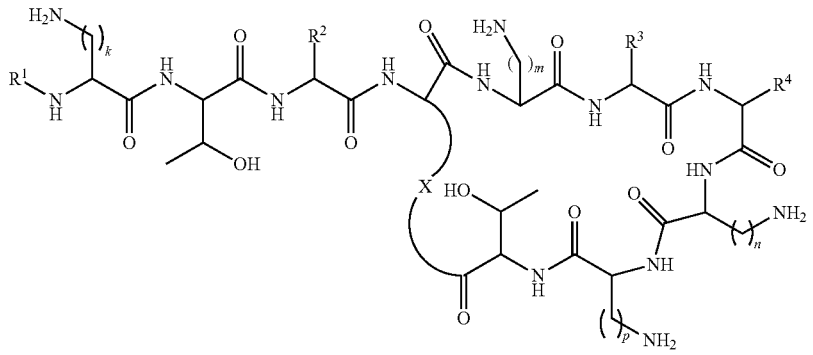

| Compound | $R^1$ | $R^2$ | $R^3$ | $R^4$ | X | k | m | n | p |
|---|---|---|---|---|---|---|---|---|---|
| 1 | Octanoyl | D-Ser[a] | D-Leu[a] | Thr[a] | Dab[a] | 2 | 2 | 2 | 2 |
| 2 | Octanoyl | D-Ser | D-Leu | Ala | Dab | 2 | 2 | 2 | 2 |
| 3 | Octanoyl | D-Ser | D-Phe | Thr | Dab | 2 | 2 | 2 | 2 |
| 4 | Octanoyl | Ser | D-Leu | Thr | Dab | 2 | 2 | 2 | 2 |
| 5 | Octanoyl | D-Ser | D-Leu | Val | Dab | 2 | 2 | 2 | 2 |
| 6 | Octanoyl | D-Ser | D-Leu | Ser | Dab | 2 | 2 | 2 | 2 |
| 7 | Octanoyl | D-Ser | D-Nle | Thr | Dab | 2 | 2 | 2 | 2 |
| 8 | Hexanoyl | D-Ser | D-Leu | Thr | Dab | 2 | 2 | 2 | 2 |
| 9 | Decanoyl | D-Ser | D-Leu | Thr | Dab | 2 | 2 | 2 | 2 |
| 10 | Dodec[a] | D-Ser | D-Leu | Thr | Dab | 2 | 2 | 2 | 2 |
| 11 | 4-BPC | D-Ser | D-Leu | Thr | Dab | 2 | 2 | 2 | 2 |
| 12 | PA | D-Ser | D-Leu | Thr | Dab | 2 | 2 | 2 | 2 |
| 13 | Octanoyl | D-Ser | D-Leu | Thr | Dab | 1 | 2 | 2 | 2 |
| 14 | Octanoyl | D-Ser | D-Leu | Thr | Dab | 3 | 2 | 2 | 2 |
| 15 | Octanoyl | D-Thr | D-Leu | Thr | Dab | 2 | 2 | 2 | 2 |
| 16 | Heptanoyl | D-Ser | D-Leu | Thr | Dab | 2 | 2 | 2 | 2 |
| 17 | Nonanoyl | D-Ser | D-Leu | Thr | Dab | 2 | 2 | 2 | 2 |
| 18 | 3-TFMB | D-Ser | D-Leu | Abu | Dab | 2 | 2 | 2 | 2 |
| 19 | 3-TFMB | D-Ser | D-Leu | Thr | Dab | 2 | 2 | 2 | 2 |

[a]for $R^2$, $R^3$, $R^4$ and X, the amino acid shown in these columns is indicative of the side chain and stereochemistry at these positions; Dodec = dodecanoyl, 4-BPC = 4-biphenylcarboxyl, PA = phenylacetyl, 3-TFMB = 3-trifluoromethylbenzoyl, Dab = diaminobutyric acid, Nle = norleucine, Abu = 2-aminobutyric acid, Phe = phenylalanine, Thr = threonine, Ala = alanine, Ser = serine, Val = valine, D- indicates D-amino acids.

In another embodiment compounds of the formula (IIa) are selected from those compounds listed in Table 2.

TABLE 2

Compounds of formula (IIa):

(IIa)

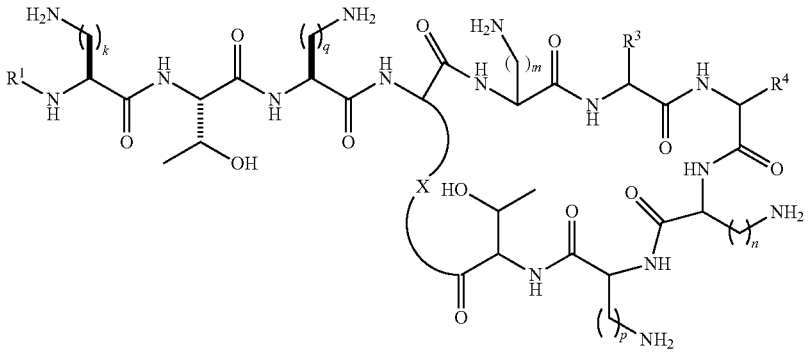

| Compound | $R^1$ | $R^3$ | $R^4$ | X | k | q | m | n | p |
|---|---|---|---|---|---|---|---|---|---|
| 20 | Octanoyl | D-Leu[a] | Thr[a] | Dab[a] | 2 | 2 | 2 | 2 | 2 |
| 21 | Octanoyl | D-Leu | Ala | Dab | 2 | 2 | 2 | 2 | 2 |
| 22 | Octanoyl | D-Phe | Thr | Dab | 2 | 2 | 2 | 2 | 2 |
| 23 | Octanoyl | D-Leu | Val | Dab | 2 | 2 | 2 | 2 | 2 |
| 24 | Octanoyl | D-Nle | Thr | Dab | 2 | 2 | 2 | 2 | 2 |

TABLE 2-continued

Compounds of formula (IIa):

(IIa)

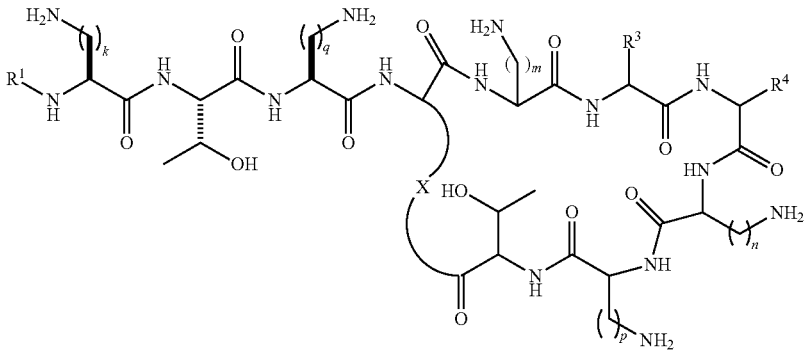

| Compound | $R^1$ | $R^3$ | $R^4$ | X | k | q | m | n | p |
|---|---|---|---|---|---|---|---|---|---|
| 25 | Octanoyl | D-Leu | Ser | Dab | 2 | 2 | 2 | 2 | 2 |
| 26 | Hexanoyl | D-Leu | Thr | Dab | 2 | 2 | 2 | 2 | 2 |
| 27 | Decanoyl | D-Leu | Thr | Dab | 2 | 2 | 2 | 2 | 2 |
| 28 | Dodec[a] | D-Leu | Thr | Dab | 2 | 2 | 2 | 2 | 2 |
| 29 | 4-BPC | D-Leu | Thr | Dab | 2 | 2 | 2 | 2 | 2 |
| 30 | PA | D-Leu | Thr | Dab | 2 | 2 | 2 | 2 | 2 |
| 31 | Octanoyl | D-Leu | Thr | Dab | 1 | 2 | 2 | 2 | 2 |
| 32 | Octanoyl | D-Leu | Thr | Dab | 3 | 2 | 2 | 2 | 2 |
| 33 | Octanoyl | D-Leu | Thr | Dab | 2 | 1 | 2 | 2 | 2 |
| 34 | Octanoyl | D-Leu | Thr | Dab | 2 | 3 | 2 | 2 | 2 |
| 35 | Octanoyl | D-Leu | Ala | Dab | 2 | 1 | 2 | 2 | 2 |
| 36 | Octanoyl | D-Leu | Val | Dab | 2 | 1 | 2 | 2 | 2 |
| 37 | Decanoyl | D-Leu | Thr | Dab | 2 | 1 | 2 | 2 | 2 |
| 38 | Decanoyl | D-Leu | Ala | Dab | 2 | 1 | 2 | 2 | 2 |
| 39 | Decanoyl | D-Leu | Val | Dab | 2 | 1 | 2 | 2 | 2 |
| 40 | Decanoyl | D-Leu | Ala | Dab | 2 | 2 | 2 | 2 | 2 |
| 41 | Decanoyl | D-Leu | Val | Dab | 2 | 2 | 2 | 2 | 2 |
| 42 | Heptanoyl | D-Leu | Thr | Dab | 2 | 2 | 2 | 2 | 2 |
| 43 | Nonanoyl | D-Leu | Thr | Dab | 2 | 2 | 2 | 2 | 2 |
| 44 | Heptanoyl | D-Leu | Thr | Dab | 2 | 1 | 2 | 2 | 2 |
| 45 | Octanoyl | D-Leu | Aib | Dab | 2 | 1 | 2 | 2 | 2 |
| 46 | Octanoyl | D-Leu | Abu | Dab | 2 | 1 | 2 | 2 | 2 |
| 47 | Octanoyl | D-Leu | Tle | Dab | 2 | 1 | 2 | 2 | 2 |
| 48 | Octanoyl | D-Leu | Thr | Dab | 1 | 1 | 2 | 2 | 2 |
| 49 | Octanoyl | D-Nva | Thr | Dab | 2 | 1 | 2 | 2 | 2 |
| 50 | Octanoyl | D-Leu | Thr | Dab | 2 | 1 | 2 | 2 | 1 |
| 51 | Octanoyl | D-Leu | Thr | Dab | 2 | 1 | 2 | 1 | 2 |
| 52 | Octanoyl | D-Leu | Thr | Dab | 2 | 1 | 1 | 2 | 2 |
| 53 | Octanoyl | D-Leu | Thr | Dab | 2 | 1 | 2 | 2 | 3 |
| 54 | Octanoyl | D-Leu | Thr | Dab | 2 | 1 | 2 | 3 | 2 |
| 55 | Octanoyl | D-Leu | Thr | Dab | 2 | 1 | 3 | 2 | 2 |
| 56 | 4-TFMB | D-Leu | Thr | Dab | 2 | 1 | 2 | 2 | 2 |
| 57 | 3,4-DCB | D-Leu | Thr | Dab | 2 | 1 | 2 | 2 | 2 |
| 58 | Nonanoyl | D-Leu | Thr | Dab | 2 | 1 | 2 | 2 | 2 |
| 59 | Nonanoyl | D-Leu | Abu | Dab | 2 | 1 | 2 | 2 | 2 |
| 60 | Octanoyl | D-Leu | Abu | Dab | 2 | 2 | 2 | 2 | 2 |
| 61 | 3-CPA | D-Leu | Thr | Dab | 2 | 1 | 2 | 2 | 2 |
| 62 | 2,4-DCPA | D-Leu | Thr | Dab | 2 | 1 | 2 | 2 | 2 |
| 63 | Heptanoyl | D-Leu | Abu | Ala | 2 | 1 | 2 | 2 | 2 |
| 64 | Heptanoyl | D-Leu | Abu | Dab | 2 | 1 | 2 | 2 | 2 |
| 65 | 6-MH | D-Leu | Ala | Dab | 2 | 1 | 2 | 2 | 2 |
| 66 | 6-MH | D-Leu | Abu | Dab | 2 | 1 | 2 | 2 | 2 |
| 67 | Hexanoyl | D-Leu | Ala | Dab | 2 | 1 | 2 | 2 | 2 |
| 68 | Hexanoyl | D-Leu | Abu | Dab | 2 | 1 | 2 | 2 | 2 |
| 69 | Octanoyl | D-Nva | Abu | Dab | 2 | 1 | 2 | 2 | 2 |
| 70 | 2,4-DCPA | D-Leu | Abu | Dab | 2 | 1 | 2 | 2 | 2 |
| 71 | 3,4-DCB | D-Leu | Abu | Dab | 2 | 1 | 2 | 2 | 2 |
| 72 | 2-CB | D-Leu | Abu | Dab | 2 | 1 | 2 | 2 | 2 |
| 73 | 2-FB | D-Leu | Abu | Dab | 2 | 1 | 2 | 2 | 2 |
| 74 | 4-TFMB | D-Leu | Abu | Dab | 2 | 1 | 2 | 2 | 2 |
| 75 | 2-MB | D-Leu | Abu | Dab | 2 | 1 | 2 | 2 | 2 |
| 76 | 2-MPA | D-Leu | Abu | Dab | 2 | 1 | 2 | 2 | 2 |
| 77 | 4-CPA | D-Leu | Abu | Dab | 2 | 1 | 2 | 2 | 2 |
| 78 | PA | D-Leu | Abu | Dab | 2 | 1 | 2 | 2 | 2 |
| 79 | 3-CPA | D-Leu | Abu | Dab | 2 | 1 | 2 | 2 | 2 |
| 80 | 4-MPA | D-Leu | Abu | Dab | 2 | 1 | 2 | 2 | 2 |
| 81 | 3,4-DCPA | D-Leu | Abu | Dab | 2 | 1 | 2 | 2 | 2 |

TABLE 2-continued

Compounds of formula (IIa):

(IIa)

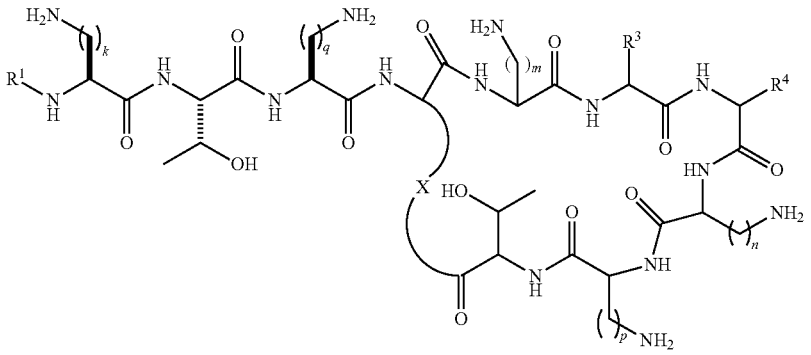

| Compound | $R^1$ | $R^3$ | $R^4$ | X | k | q | m | n | p |
|---|---|---|---|---|---|---|---|---|---|
| 82 | 2,4-DCB | D-Leu | Abu | Dab | 2 | 1 | 2 | 2 | 2 |
| 83 | 3,4-DMB | D-Leu | Abu | Dab | 2 | 1 | 2 | 2 | 2 |
| 84 | 2-CPA | D-Leu | Abu | Dab | 2 | 1 | 2 | 2 | 2 |
| 85 | 2-FPA | D-Leu | Abu | Dab | 2 | 1 | 2 | 2 | 2 |
| 86 | 3-FB | D-Leu | Abu | Dab | 2 | 1 | 2 | 2 | 2 |
| 87 | 3-MB | D-Leu | Abu | Dab | 2 | 1 | 2 | 2 | 2 |
| 88 | 3-CB | D-Leu | Abu | Dab | 2 | 1 | 2 | 2 | 2 |
| 89 | 2,4-DMB | D-Leu | Abu | Dab | 2 | 1 | 2 | 2 | 2 |
| 90 | 2,3-DCB | D-Leu | Abu | Dab | 2 | 1 | 2 | 2 | 2 |
| 91 | 2,3-DMB | D-Leu | Abu | Dab | 2 | 1 | 2 | 2 | 2 |
| 92 | 2,4,6-TMB | D-Leu | Abu | Dab | 2 | 1 | 2 | 2 | 2 |
| 93 | 3,5-DMB | D-Leu | Abu | Dab | 2 | 1 | 2 | 2 | 2 |
| 94 | 4-CB | D-Leu | Abu | Dab | 2 | 1 | 2 | 2 | 2 |
| 95 | 2,4,6-TCB | D-Leu | Abu | Dab | 2 | 1 | 2 | 2 | 2 |
| 96 | 3,5-DCB | D-Leu | Abu | Dab | 2 | 1 | 2 | 2 | 2 |
| 97 | 3,5-BTFMB | D-Leu | Abu | Dab | 2 | 1 | 2 | 2 | 2 |
| 98 | 4-MB | D-Leu | Abu | Dab | 2 | 1 | 2 | 2 | 2 |
| 99 | 4-IPB | D-Leu | Abu | Dab | 2 | 1 | 2 | 2 | 2 |
| 100 | 4-EB | D-Leu | Abu | Dab | 2 | 1 | 2 | 2 | 2 |
| 101 | 2-C-4-MB | D-Leu | Abu | Dab | 2 | 1 | 2 | 2 | 2 |
| 102 | 3-F-4-MB | D-Leu | Abu | Dab | 2 | 1 | 2 | 2 | 2 |
| 103 | 3,4-DMPA | D-Leu | Abu | Dab | 2 | 1 | 2 | 2 | 2 |
| 104 | 4-C-3-MB | D-Leu | Abu | Dab | 2 | 1 | 2 | 2 | 2 |
| 105 | 3-C-4-MB | D-Leu | Abu | Dab | 2 | 1 | 2 | 2 | 2 |
| 106 | 3-TFMB | D-Leu | Abu | Dab | 2 | 1 | 2 | 2 | 2 |
| 107 | 4-C-3-FB | D-Leu | Abu | Dab | 2 | 1 | 2 | 2 | 2 |
| 108 | 3-F-5-TFMB | D-Leu | Abu | Dab | 2 | 1 | 2 | 2 | 2 |
| 109 | 2-C-4-TFMB | D-Leu | Abu | Dab | 2 | 1 | 2 | 2 | 2 |
| 110 | 3-C-4-FB | D-Leu | Abu | Dab | 2 | 1 | 2 | 2 | 2 |
| 111 | 3-F-4-TFMB | D-Leu | Abu | Dab | 2 | 1 | 2 | 2 | 2 |
| 112 | 4-C-3-TFMB | D-Leu | Abu | Dab | 2 | 1 | 2 | 2 | 2 |
| 113 | 4-M-3-TFMB | D-Leu | Abu | Dab | 2 | 1 | 2 | 2 | 2 |
| 114 | 3-C-5-MB | D-Leu | Abu | Dab | 2 | 1 | 2 | 2 | 2 |
| 115 | 3-C-4-TFMB | D-Leu | Abu | Dab | 2 | 1 | 2 | 2 | 2 |
| 116 | 3-C-5-FB | D-Leu | Abu | Dab | 2 | 1 | 2 | 2 | 2 |
| 117 | 3,5-DCB | D-Leu | Ala | Dab | 2 | 1 | 2 | 2 | 2 |
| 118 | 3,5-DCB | D-Leu | Thr | Dab | 2 | 1 | 2 | 2 | 2 |
| 119 | 3-M-4-TFMB | D-Leu | Abu | Dab | 2 | 1 | 2 | 2 | 2 |
| 120 | 3-M-5-TFMB | D-Leu | Abu | Dab | 2 | 1 | 2 | 2 | 2 |
| 121 | 3-TFMB | D-Nle | Abu | Dab | 2 | 1 | 2 | 2 | 2 |
| 122 | 3-TFMB | D-Phe | Abu | Dab | 2 | 1 | 2 | 2 | 2 |
| 123 | 3-TFMB | D-Nle | Thr | Dab | 2 | 1 | 2 | 2 | 2 |
| 124 | 3-TFMB | D-Phe | Thr | Dab | 2 | 1 | 2 | 2 | 2 |
| 125 | 3-TFMB | D-Nle | Ala | Dab | 2 | 1 | 2 | 2 | 2 |
| 126 | 3-TFMB | D-Phe | Ala | Dab | 2 | 1 | 2 | 2 | 2 |
| 127 | 4-TFMPA | D-Leu | Abu | Dab | 2 | 1 | 2 | 2 | 2 |
| 128 | Octanoyl | D-Phe | Ala | Dab | 2 | 1 | 2 | 2 | 2 |
| 129 | Octanoyl | D-Phe | Thr | Dab | 2 | 1 | 2 | 2 | 2 |
| 130 | Octanoyl | D-Phe | Abu | Dab | 2 | 1 | 2 | 2 | 2 |
| 131 | Heptanoyl | D-Phe | Abu | Dab | 2 | 1 | 2 | 2 | 2 |
| 132 | Nonanoyl | D-Leu | Ala | Dab | 2 | 1 | 2 | 2 | 2 |
| 133 | 3,4,5-TFB | D-Leu | Abu | Dab | 2 | 1 | 2 | 2 | 2 |
| 134 | 4-C-2-FB | D-Leu | Abu | Dab | 2 | 1 | 2 | 2 | 2 |
| 135 | 2-C-4-FB | D-Leu | Abu | Dab | 2 | 1 | 2 | 2 | 2 |
| 136 | 4-C-2-TFMB | D-Leu | Abu | Dab | 2 | 1 | 2 | 2 | 2 |
| 137 | 2-F-4-TFMB | D-Leu | Abu | Dab | 2 | 1 | 2 | 2 | 2 |
| 138 | 3-BPC | D-Leu | Abu | Dab | 2 | 1 | 2 | 2 | 2 |

TABLE 2-continued

Compounds of formula (IIa):

(IIa)

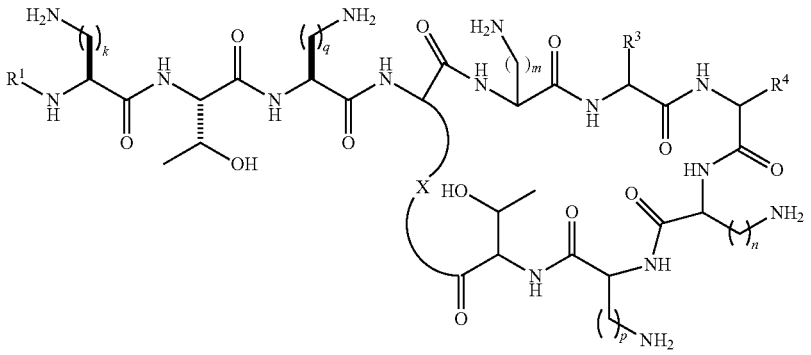

| Compound | $R^1$ | $R^3$ | $R^4$ | X | k | q | m | n | p |
|---|---|---|---|---|---|---|---|---|---|
| 139 | (S,R)-6-MO | D-Leu | Abu | Dab | 2 | 1 | 2 | 2 | 2 |
| 140 | Octanoyl | D-Phe | Aib | Dab | 2 | 1 | 2 | 2 | 2 |
| 141 | 3-TFMB | D-Leu | Abu | Dab | 3 | 1 | 2 | 2 | 2 |
| 142 | 4-BPC | D-Leu | Abu | Dab | 2 | 1 | 2 | 2 | 2 |
| 143 | Nonanoyl | D-Phe | Ser | Dab | 2 | 1 | 2 | 2 | 2 |
| 144 | 4-Cl-BP-4-C | D-Leu | Ala | Dab | 2 | 1 | 2 | 2 | 2 |
| 145 | 3-PP | D-Leu | Abu | Dab | 2 | 1 | 2 | 2 | 2 |
| 146 | 4-PB | D-Leu | Ala | Dab | 2 | 1 | 2 | 2 | 2 |
| 147 | 2,4-DCB | D-Leu | Abu | Dab | 2 | 3 | 2 | 2 | 2 |
| 148 | 2,4-DCPS | D-Leu | Abu | Dab | 2 | 1 | 2 | 2 | 2 |
| 149 | Octanoyl | D-Leu | Thr | Orn | 2 | 2 | 2 | 2 | 2 |

[a]for $R^3$, $R^4$ and X, the amino acid shown in these columns is indicative of the side chain and stereochemistry at these positions; Dodec = dodecanoyl, 4-BPC = 4-biphenylcarboxyl, PA = phenylacetyl, 6-MH = 6-methylheptanoyl, 4-TFMPA = 4-trifluoromethylphenylacetyl, 2-MB = 2-methylbenzoyl, 3-MB = 3-methylbenzoyl, 4-MB = 4-methylbenzoyl, 3-F-4-MB = 3-fluoro-4-methylbenzoyl, 4-C-3-MB = 4-chloro-3-methylbenzoyl, 3-C-4-MB = 3-chloro-4-methylbenzoyl, 3-C-5-MB = 3-chloro-5-methylbenzoyl, 2-FPA = 2-fluorophenylacetyl, 3-TFMB = 3-trifluoromethylbenzoyl, 4-TFMB = 4-trifluoromethylbenzoyl, 2-C-4-TFMB = 2-chloro-4-trifluoromethylbenzoyl, 4-C-3-TFMB = 4-chloro-3-trifluoromethylbenzoyl, 3-C-4-TFMB = 3-chloro-4-trifluoromethylbenzoyl, 3-F-4-TFMB = 3-fluoro-4-trifluoromethylbenzoyl, 3-F-5-TFMB = 3-fluoro-5-trifluoromethylbenzoyl, 4-M-3-TFMB = 4-methyl-3-trifluoromethylbenzoyl, 3-M-4-TFMB = 3-methyl-4-trifluoromethylbenzoyl, 3-M-5-TFMB = 3-methyl-5-trifluoromethylbenzoyl, 2-F-4-TFMB = 2-fluoro-4-trifluoromethylbenzoyl, 3,4,5-TFMB = 3,4,5-trifluoromethylbenzoyl, 4-C-2-TFMB = 4-chloro-2-trifluoromethylbenzoyl, 3,5-BTFMB = 3,5-bis(trifluoromethyl)benzoyl, 2,4,6-TMB = 2,4,6-trimethylbenzoyl, 2,3-DMB = 2,3-dimethylbenzoyl, 2,4-DMB = 2,4-dimethylbenzoyl, 3,4-DMB = 3,4-dimethylbenzoyl, 3,5-DMB = 3,5-dimethylbenzoyl, 2-C-4-MB = 2-chloro-4-methylbenzoyl, 4-EB = 4-ethylbenzoyl, 4-IPB = 4-Isopropylbenzoyl, 2,4-DCPA = 2,4-dichlorophenylacetyl, 3,4-DCPA = 3,4-dichlorophenylacetyl, 2-CPA = 2-chlorophenylacetyl, 3-CPA = 3-chlorophenylacetyl, 4-CPA = 4-chlorophenylacetyl, 2-CB = 2-chlorobenzoyl, 3-CB = 3-chlorobenzoyl, 4-CB = 4-chlorobenzoyl, 2,3-DCB = 2,3-dichlorobenzoyl, 2,4-DCB = 2,4-dichlorobenzoyl, 3,4-DCB = 3,4-dichlorobenzoyl, 3,5-DCB = 3,5-dichlorobenzoyl, 2,4,6-TCB = 2,4,6-trichlorobenzoyl, 2-FB = 2-fluorobenzoyl, 3-FB = 3-fluorobenzoyl, 2-C-4-FB = 2-chloro-4-fluorobenzoyl, 3-C-4-FB = 3-Chloro-4-fluorobenzoyl, 3-C-5-FB = 3-chloro-5-fluorobenzoyl, 4-C-2-FB = 4-chloro-2-fluorobenzoyl, 4-C-3-FB = 4-chloro-3-fluorobenzoyl, 2-MPA = 2-methylphenylacetyl, 4-MPA = 4-methylphenylacetyl, 3,4-DMPA = 3,4-dimethylphenylacetyl, (S,R)-6-MO = (S,R)-6-methyloctanoyl, 3-BPC = 3-biphenylcarboxyl, 4-Cl-BP-4-C = 4-chloro-biphenyl-4-carboxyl, 3-PP = 3-phenylproponyl, 4-PB = 4-phenylbutanoyl, 2,4-DCPS = 2,4-dichlorophenylsulfonyl, Dab = diaminobutyric acid, Tle = t-butylglycine, Aib = aminoisobutyric acid, Abu = 2-aminobutyric acid, Phe = phenylalanine, Thr = threonine, Ala = alanine, Ser = serine, Val = valine, Nva = norvaline, Nle = norleucine, D- indicates D-amino acids.

In another preferred embodiment there is provided methods preventing or treating a MDR Gram-negative bacterial infection comprising administering a therapeutically effective amount of one or more compounds of the formula (I) and/or formula (II) as herein defined.

Accordingly, in a further preferred embodiment there is provided one or more compounds of formula (I) and/or formula (II) as herein defined for use in the prevention or treatment of a MDR Gram-negative bacterial infection.

It will be appreciated that for Gram-negative bacteria to be multidrug-resistant the bacteria will be non-susceptible to at least one agent in three or more antibacterial categories. Gram-negative bacteria that are non-susceptible to at least one agent in all but two or fewer antibacterial categories are classified as extensively, or extremely, drug resistant (XDR). Gram-negative bacteria that are non-susceptible to all agents in all antibacterial categories are classified as "pandrug-resistant" (PDR) (Magiorakos, A. P. et al. (2011) European Society of Clinical Microbiology and Infectious Diseases, Clin Microbiol Infect, 18, 268-281). Table 3 provides a list of antibacterial agents falling within each of the antibacterial categories.

TABLE 3

Antibacterial categories and agents

| Antibacterial Category | Antibacterial Agent |
|---|---|
| Aminoglycosides | Gentamicin |
| | Tobramycin |
| | Amikacin |
| | Netilmicin |
| Antipseudomonal carbapenems | Imipenem |
| | Meropenem |
| | Doripenem |
| Antipseudomonal cephalosporins | Ceftazidime |
| | Cefepime |
| Antipseudomonal fluoroquinolones | Ciprofloxacin |
| | Levofloxacin |
| Antipseudomonal penicillins + β-lactamase inhibitors | Ticarcillin-clavulanic acid |
| | Piperacillin-tazobactum |
| Monobactams | Aztreonam |
| Phosphonic acids | Fosfomycin |
| Polymyxins | Colistin |
| | Polymyxin B |

It will be appreciated that in order to treat a Gram-negative bacterial infection in a subject in need thereof, it may be beneficial to administer to the subject one or more compounds of the formula (I) as herein described or one or more compounds of the formula (II) as herein described. It is envisaged that in one embodiment, treatment of a Gram-negative bacterial infection will comprise administering to a subject in need thereof a compound of the formula (I). It is also envisaged that treatment of a Gram-negative bacterial infection will comprise administration of a compound of the formula (II) to a subject in need thereof.

It will be appreciated that in order to minimise the nephrotoxic side effects associated with the polymyxin analogues in current clinical use and to maintain or improve upon the efficacy of the compounds against a broad spectrum of Gram-negative bacteria, it may be beneficial to administer to the subject in need thereof a combination of two or more compounds of the present invention. It is envisaged that in one embodiment, treatment of a Gram-negative bacterial infection will comprise administration of two or more compounds of the formula (I) to a subject in need thereof. It is also envisaged that treatment of a Gram-negative bacterial infection will comprise administration of two or more compounds of the formula (II) to a subject in need thereof. In other embodiments it is envisaged that treatment of a Gram-negative bacterial infection will comprise administration of one or more compounds of the formula (I) together with one or more compounds of the formula (II) to a subject in need thereof. In further embodiments it is envisaged that treatment of a Gram-negative bacterial infection will comprise administration of one or both of the naturally occurring polymyxin analogues polymyxin $D_1/D_2$ to a subject in need thereof (compounds 150 and 151, respectively). In another embodiment it is envisaged that treatment of a Gram-negative bacterial infection will comprise administration of one or both of the naturally occurring polymyxin analogues polymyxin $M_1/M_2$ to a subject in need thereof (compounds 152 and 153, respectively).

In a preferred embodiment there is provided the use of one or more compounds of the formula (Ia) and/or (IIa) as hereinbefore defined in the manufacture of a medicament for preventing or treating a Gram-negative bacterial infection.

In a further preferred embodiment there is provided one or more compounds of the formula (Ia) and/or (IIa) as hereinbefore defined for use in the prevention or treatment a Gram-negative bacterial infection.

Polymyxin D and polymyxin M, like polymyxin B and colistin, are mixtures of closely related peptides obtained from fermentation (Table 4). However, unlike polymyxin B and colistin, the components of the polymyxin D and M mixtures obtained from fermentation have not been well characterised. To date, the components that have been identified in polymyxin D preparations are polymyxin $D_1$ and $D_2$, whilst for polymyxin M the components are polymyxin $M_1$ and $M_2$ (Kimura, Y, et al. (1981), J. Chromatography, 206, 563-572; Orwa, J. A., et al. (2001) J. Chromatography A. 912, 369-373; Govaerts, C., et al. (2002) J. Chromatography A. 976, 65-78). Because of their perceived nephrotoxic side effects, polymyxin D and M mixtures, or their individual components, have not found use in the clinical treatment of Gram-negative bacterial infections, in particular, MDR Gram-negative bacterial infections (Bryer, M. S., et al. (1949) Ann. N. Y. Acad. Sci., 51, 935-943; Brownlee, G., et. Al. (1949) Ann. N. Y. Acad. Sci., 51, 952-957; Filippos'yan, S. T. Antibiotiki, (1969) 14, 5, 459-463).

TABLE 4

The chemical structures of the polymyxin B, E (Colistin), D and M lipopeptides.

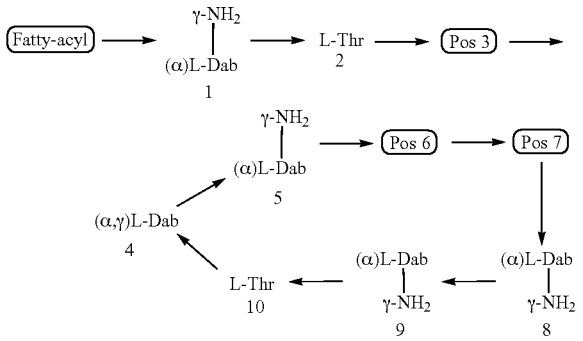

| Polymyxin | Fatty-acyl group | Pos 3 | Pos 6 | Pos 7 |
|---|---|---|---|---|
| $B_1$ | (S)-6-methyloctanoyl | L-Dab | D-Phe | L-Leu |
| $B_2$ | 6-methylheptanoyl | L-Dab | D-Phe | L-Leu |
| $E_1$ (Colistin A) | (S)-6-methyloctanoyl | L-Dab | D-Leu | L-Leu |
| $E_2$ (Colistin B) | 6-methylheptanoyl | L-Dab | D-Leu | L-Leu |
| $D_1$ (150) | (S)-6-methyloctanoyl | D-Ser | D-Leu | L-Thr |
| $D_2$ (151) | 6-methylheptanoyl | D-Ser | D-Leu | L-Thr |
| $M_1$ (152) | (S)-6-methyloctanoyl | L-Dab | D-Leu | L-Thr |
| $M_2$ (153) | 6-methylheptanoyl | L-Dab | D-Leu | L-Thr |

D-Dab = D-diaminobutyric acid, L-Dab = L-diaminobutyric acid, D-Phe = D-phenylalanine, L-Leu = L-Leucine, D-Ser = D-Serine, L-Thr = L-Threonine However, the present inventors have discovered that the perceived nephrotoxicity associated with the individual components polymyxin $D_1/D_2$ and polymyxin $M_1/M_2$ is unwarranted. Without wishing to be limited by theory, it is believed that this may be attributed to the fact that earlier toxicity tests were conducted on samples of polymyxin D mixtures and polymyxin M mixtures that were not well characterised in terms of chemical composition and purity, and not on pure samples of the individual components obtained by total organic synthesis or pure samples obtained by extensively purifying fermentation products (Bell. P. H. and Bone J. F., (1949) Ann. N. Y. Acad. Sci., 51, 897-908; Bryer, M. S., et al. (1949) Ann. N. Y. Acad. Sci., 51, 935-943; Brownlee, G., et. Al. (1949) Ann. N. Y. Acad. Sci., 51, 952-957). The present inventors have discovered that pure isolates of the individual components polymyxin $D_2$ and polymyxin $M_2$ exhibit no significant nephrotoxicity in the in vivo nephrotoxicity model tested. Pure isolates of the individual components polymyxin $D_1$ and polymyxin $M_1$ exhibit some nephrotoxicity, but have improved nephrotoxicity profiles compared to the clinically available polymyxin B and colistin.

It has now been found that certain combinations of amino acid residues at the $3^{rd}$, $6^{th}$ and $7^{th}$ positions of the polymyxin core, together with select N-terminal fatty acyl groups, can reduce the nephrotoxicity of the resultant compounds relative to polymyxin B or colistin, whilst maintaining or improving the compound's antibacterial efficacy. Without wishing to be limited by theory, it is believed that replacement of one or both of the $6^{th}$ and $7^{th}$ residues in the polymyxin compound with less hydrophobic residues can reduce the level of nephrotoxicity. It is also believed that selection of certain amino acid residues at the $3^{rd}$ position and certain N-terminal fatty acyl group reduces the nephrotoxicity of the resultant compound due to the effect these groups have on the overall conformation of the compound.

It is believed that the change in conformation interferes with the compounds ability to form key interactions with molecular targets that trigger physiological events that lead to nephrotoxicity.

In general, techniques for preparing the compounds of the invention are well known in the art for example see:

a) Alewood, P.; Alewood, D.; Miranda, L.; Love, S.; Meutermans, W.; Wilson, D. (1997) Meth. Enzymol., 289, 14-28;

b) Merrifield, R. B. (1964) J. Am. Chem. Soc., 85, 2149;

c) Bodanzsky, "Principles of Peptide Synthesis", 2nd Ed., Springer-Verlag (1993); and d) Houghten, (1985) Proc. Natl. Acad. Sci. USA, 82, 5131.

Of particular relevance to the synthesis polymyxin type compounds are: Sharma, S. K., et al. (1999) J. Pept. Res. 53, 501-506; Kline, T., Holub, D., Therrien, J. et al. (2001) J. Pept. Res. 57, 175-187; de Visser, P. C., et al. (1999) J. Pept. Res. 61, 298-306; Sukura, N., et al. (2004) Bull. Chem. Soc. Jpn. 77, 1915-1924; and Vaara, M., Fox, J., Loidl, G., Siikanen, O. et al. (2008) Antimicrob. Agents Chemother. 52(9), 3229-3236. The entire contents of these documents are incorporated herein by reference.

Known solid or solution phase techniques may be used in the synthesis of the compounds of the present invention, such as coupling of the N- or C-terminus to a solid support (typically a resin) followed by step-wise synthesis of the linear peptide. An orthogonal protecting group strategy may be used to facilitate selective deprotection and cyclization to form the cyclic heptapeptide core of the compound. Protecting group chemistries for the protection of amino acid residues, including side chains, are well known in the art and may be found, for example, in: Theodora W. Greene and Peter G. M. Wuts, Protecting Groups in Organic Synthesis (Third Edition, John Wiley & Sons, Inc, 1999), the entire contents of which is incorporated herein by reference.

As a general strategy, the synthesis of the compounds of the present invention may be performed in four stages. In the first stage, amino acids may be protected for incorporation into the compound, such as the protection of isoleucine as Fmoc-isoleucine. Second, a partially protected linear peptide which selectively exposes only the functional groups required for cyclisation may be synthesised using solid phase techniques. Third the cyclisation reaction may be performed in solution to produce the protected cyclic lipopeptide. Fourth the remaining side chain protecting groups may be deprotected to furnish the compound.

Where the compounds of the present invention require purification, chromatographic techniques such as high-performance liquid chromatography (HPLC) and reversed-phase HPLC may be used. The peptides may be characterised by mass spectrometry and/or other appropriate methods.

Where the compound comprises one or more functional groups that may be protonated or deprotonated (for example at physiological pH) the compound may be prepared and/or isolated as a pharmaceutically acceptable salt. It will be appreciated that the compound may be zwitterionic at a given pH. As used herein the expression "pharmaceutically acceptable salt" refers to the salt of a given compound, wherein the salt is suitable for administration as a pharmaceutical. Such salts may be formed, for example, by the reaction of an acid or a base with an amine or a carboxylic acid group respectively.

Pharmaceutically acceptable acid addition salts may be prepared from inorganic and organic acids. Examples of inorganic acids include hydrochloric acid, hydrobromic acid, sulfuric acid, nitric acid, phosphoric acid and the like. Examples of organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts may be prepared from inorganic and organic bases. Corresponding counter ions derived from inorganic bases include the sodium, potassium, lithium, ammonium, calcium and magnesium salts. Organic bases include primary, secondary and tertiary amines, substituted amines including naturally-occurring substituted amines, and cyclic amines, including isopropylamine, trimethyl amine, diethylamine, tri ethyl amine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine.

Acid/base addition salts tend to be more soluble in aqueous solvents than the corresponding free acid/base forms.

The compounds of the invention may be in crystalline form or as solvates (e.g. hydrates) and it is intended that both forms are within the scope of the present invention. The term "solvate" is a complex of variable stoichiometry formed by a solute (in this invention, a peptide of the invention) and a solvent. Such solvents should not interfere with the biological activity of the solute. Solvents may be, by way of example, water, ethanol or acetic acid. Methods of solvation are generally known within the art.

The compounds of the invention may be in the form of a pro-drug. The term "pro-drug" is used in its broadest sense and encompasses those derivatives that are converted in vivo to the peptides of the invention. Such derivatives would readily occur to those skilled in the art and include, for example, compounds where a free hydroxy group is converted into an ester derivative or a ring nitrogen atom is converted to an N-oxide. Examples of ester derivatives include alkyl esters (for example acetates, lactates and glutamines), phosphate esters and those formed from amino acids (for example valine). Any compound that is a prodrug of a compound of the invention is within the scope and spirit of the invention. Conventional procedures for the preparation of suitable prodrugs according to the invention are described in text books, such as "Design of Prodrugs" Ed. H. Bundgaard, Elsevier, 1985, the entire contents of which is incorporated herein by reference.

The present invention also provides a pharmaceutical composition comprising a therapeutically effective amount of a compound as hereinbefore defined, or a pharmaceutically acceptable salt thereof, together with at least one pharmaceutically acceptable carrier or diluent.

The term "composition" is intended to include the formulation of an active ingredient with encapsulating material as carrier, to give a capsule in which the active ingredient (with or without other carrier) is surrounded by carriers.

While the compounds as hereinbefore described, or pharmaceutically acceptable salts thereof, may be the sole active ingredient administered to the subject, the administration of other active ingredient(s) with the compound is within the scope of the invention. In one or more embodiments it is envisaged that a combination of two or more of the compounds of the invention will be administered to the subject. It is envisaged that the compound(s) could also be administered with one or more additional therapeutic agents in combination. The combination may allow for separate, sequential or simultaneous administration of the compound (s) as hereinbefore described with the other active ingredient (s). The combination may be provided in the form of a pharmaceutical composition.

The term "combination", as used herein refers to a composition or kit of parts where the combination partners as defined above can be dosed dependently or independently or by use of different fixed combinations with distinguished amounts of the combination partners, i.e., simultaneously or at different time points. The combination partners can then, e.g., be administered simultaneously or chronologically staggered, that is at different time points and with equal or different time intervals for any part of the kit of parts. The ratio of the total amounts of the combination partners to be administered in the combination can be varied, e.g. in order to cope with the needs of a patient sub-population to be treated or the needs of the single patient which different needs can be due to age, sex, body weight, etc. of the patients.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the active compound care should be taken to ensure that the activity of the compound is not destroyed in the process and that the compound is able to reach its site of action without being destroyed. In some circumstances it may be necessary to protect the compound by means known in the art, such as, for example, micro encapsulation. Similarly the route of administration chosen should be such that the compound reaches its site of action.

Those skilled in the art may readily determine appropriate formulations for the compounds of the present invention using conventional approaches. Identification of preferred pH ranges and suitable excipients, for example antioxidants, is routine in the art. Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

The compounds as hereinbefore described, or pharmaceutically acceptable salts thereof, may be prepared in parenteral dosage forms, including those suitable for intravenous, intrathecal, and intracerebral or epidural delivery. The pharmaceutical forms suitable for injectable use include sterile injectable solutions or dispersions, and sterile powders for the extemporaneous preparation of sterile injectable solutions. They should be stable under the conditions of manufacture and storage and may be preserved against reduction or oxidation and the contaminating action of microorganisms such as bacteria or fungi.

The solvent or dispersion medium for the injectable solution or dispersion may contain any of the conventional solvent or carrier systems for the active compound, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolarity, for example, sugars or sodium chloride. Preferably, the formulation for injection will be isotonic with blood. Prolonged absorption of the injectable compositions can be brought about by the use in the compositions of agents delaying absorption, for example, aluminium monostearate and gelatin. Pharmaceutical forms suitable for injectable use may be delivered by any appropriate route including intravenous, intramuscular, intracerebral, intrathecal, epidural injection or infusion.

Sterile injectable solutions are prepared by incorporating the compounds of the invention in the required amount in the appropriate solvent with various of the other ingredients such as those enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

Other pharmaceutical forms include oral and enteral formulations of the present invention, in which the active compound may be formulated with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal or sublingual tablets, troches, capsules, elixirs, suspensions, syrups, wafers, and the like. The amount of active compound in such therapeutically useful compositions is such that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the compounds of the invention may be incorporated into sustained-release preparations and formulations, including those that allow specific delivery of the active peptide to specific regions of the gut.

Liquid formulations may also be administered enterally via a stomach or oesophageal tube. Enteral formulations may be prepared in the form of suppositories by mixing with appropriate bases, such as emulsifying bases or water-soluble bases. It is also possible, but not necessary, for the compounds of the present invention to be administered topically, intranasally, intravaginally, intraocularly and the like.

The compounds of the present invention may be administered by inhalation in the form of an aerosol spray from a pressurised dispenser or container, which contains a propellant such as carbon dioxide gas, dichlorodifluoromethane, nitrogen, propane or other suitable gas or combination of gases. The compounds may also be administered using a nebuliser.

It will be appreciated that the compounds of the present invention, having improved nephrotoxicity profiles, are particularly useful when the compounds are administered enterally or parentarally, for example, orally, intravenously or intramuscularly.

Pharmaceutically acceptable vehicles and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate the compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically acceptable vehicle. The specification for the novel dosage unit forms of the invention are dictated by and directly dependent on (a) the unique characteristics of the active material and the particular therapeutic effect to be achieved, and (b) the limitations inherent in the art of compounding active materials for the treatment of disease in living subjects having a diseased condition in which bodily health is impaired as herein disclosed in detail.

As mentioned above the principal active ingredient may be compounded for convenient and effective administration in therapeutically effective amounts with a suitable pharmaceutically acceptable vehicle in dosage unit form. A unit dosage form can, for example, contain the principal active compound in amounts ranging from 0.25 μg to about 2000 mg. Expressed in proportions, the active compound may be present in from about 0.25 μg to about 2000 mg/mL of carrier. In the case of compositions containing supplementary active ingredients, the dosages are determined by reference to the usual dose and manner of administration of the said ingredients.

As used herein, the term "effective amount" refers to an amount of compound which, when administered according to a desired dosing regimen, provides the desired therapeutic activity. Dosing may occur once, or at intervals of minutes or hours, or continuously over any one of these periods. Suitable dosages may lie within the range of about 0.1 μg per kg of body weight to 1 g per kg of body weight per dosage. A typical dosage is in the range of 1 μg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

The terms "treatment" and "treating" as used herein cover any treatment of a condition or disease in an animal, preferably a mammal, more preferably a human, and includes: (i) inhibiting the bacterial infection, e.g. arresting its proliferation; (ii) relieving the infection, e.g. causing a reduction in the severity of the infection; or (iii) relieving the conditions caused by the infection, e.g. symptoms of the infection. The terms "prevention" and "preventing" as used herein cover the prevention or prophylaxis of a condition or disease in an animal, preferably a mammal, more preferably a human and includes preventing the bacterial infection from occurring in a subject which may be predisposed to infection but has not yet been diagnosed as being infected.

In some embodiments the Gram-negative bacterial infection may be caused by one or more species selected from one or more of the genera: Acinetobacter; Actinobacillus; Bartonella; Bordetella; Brucella; Burkholderia; Campylobacter; Cyanobacteria; Enterobacter; Envinia; Escherichia; Francisella; Helicobacter; Hemophilus; Klebsiella; Legionella; Moraxella; Morganella; Neisseria; Pasteurella; Proteus; Providencia; Pseudomonas; Salmonella; Serratia; Shigella; Stenotrophomonas; Treponema; Vibrio; and Yersinia. Specific examples of species are Pseudomonas aeruginosa, Acinetobacter baumannii, Klebsiella pneumoniae, Stenotrophomonas maltophilia, Enterobacter cloacae, Escherichia coli and Salmonella enterica.

The invention will now be described with reference to the following non-limiting examples:

Example 1: Methods for Preparing Compounds of the General Formulae (I) and (II)

The following example is representative of the present invention, and provides detailed methods for preparing exemplary compounds of the present invention.

Synthesis of Compound 1:

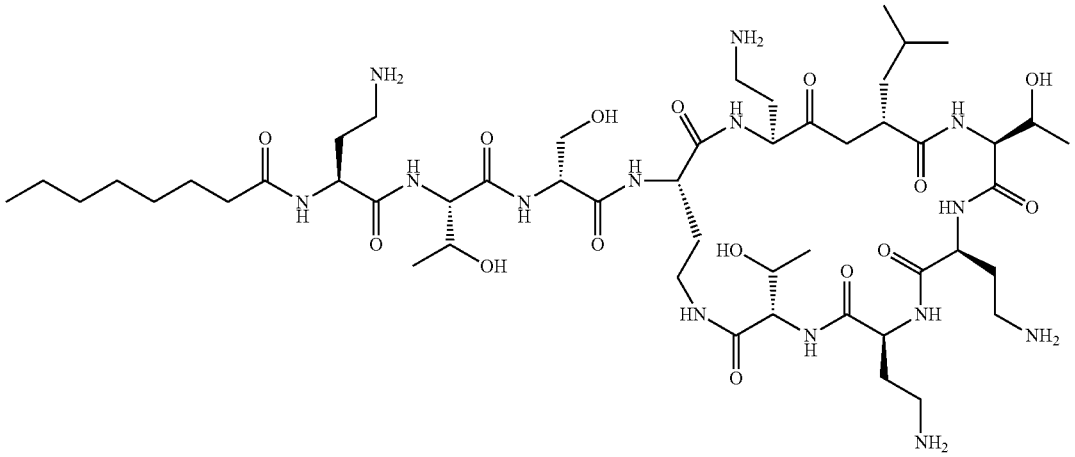

Synthesis of the protected linear peptide (residues 1-10 and the N-terminal cap) was conducted on a Protein Technologies Prelude automated peptide synthesizer using standard Fmoc solid-phase peptide chemistry.

Specifically, synthesis was undertaken using TCP-Resin, pre-loaded with Fmoc-Thr(tBu)-OH, 0.1 mmol scale. Coupling of the Fmoc-amino acids was performed using the default instrument protocol: 3 molar equivalents (relative to resin loading) of Fmoc amino acid and HCTU in DMF with activation in situ, using 6 molar equivalents of DIPEA. This was carried out for 50 min at room temperature. Fmoc deprotection was conducted using the default instrument protocol: 20% piperidine in dimethylformamide (1×5 min, 1×10 min) at room temperature. The resin was washed with DMF then treated with 3% hydrazine in DMF (4×15 min) to remove the ivDde group.

The protected linear peptide was cleaved from the resin by treating the resin with 10-20% hexafluoroisopropanol (HFIP) in DCM (1×30 min, 1×5 min). The resulting solution was concentrated in vacuo and the resulting residue (crude protected linear peptide) dissolved in DMF (10 mL) to which DPPA, (0.3 mmol, 0.65 μL, 3 molar equivalents relative to the loading of the resin) and DIPEA (0.6 mmol, 104 μL, 6 molar equivalents relative to the loading of the resin) were added. This solution was stirred at room temperature overnight. The reaction solution was then concentrated under vacuum overnight. The resulting residue was taken up in a solution of 2.5% EDT, 5% TIPS in TFA and stirred at room temperature for 2 h. To this solution 40 mL of diethyl ether was added. The resulting precipitate was collected by centrifugation and washed twice more with diethyl ether (40 mL) then air-dried in a fume food to give the crude cyclic peptide as a white solid. The resulting solid was taken up in Milli-Q water (5 mL) and de-salted using a Vari-Pure WE SAX column.

The crude cyclic peptide was purified by reversed-phase HPLC (RP-HPLC) on an Agilent 1200 quaternary pump system with a photodiode array detector (214 nm) using a Phenomenex Axia column (Luna $C_8$(2), 50×21.3 mm ID). A gradient of 60% acetonitrile in 0.1% aqueous TFA over 60 min were employed at a flow rate of 5 mL/min. Fractions collected were analysed using a Shimadzu 2020 LCMS system, incorporating a photodiode array detector (214 nm) coupled directly to an electrospray ionization source and a single quadrupole mass analyser. RP-HPLC was carried out employing a Phenomenex column (Luna C8(2), 100×2.0 mm ID) eluting with a gradient of 80% acetonitrile in 0.05% aqueous TFA, over 10 min at a flow rate of 0.2 mL/min. Mass spectra were acquired in the positive ion mode with a scan range of 200-2,000 m/z. The combined fractions were freeze-dried for two days to give compound 1 as a white TFA salt in a yield of 42.9 mg. The purity was 99.7% as estimated by RP-HPLC at 214 nm. The compound was confirmed as having the correct molecular weight (1130.2) by ESI-MS analysis: m/z (monoisotopic): $[M+2H]^{2+}$ 566.15.

It will be understood that this representative synthesis may be applied to the synthesis of a range of compounds described herein. For example, the representative synthesis may be applied to the synthesis of compounds 2 to 153 as herein described and listed in Tables 5 and 6 below.

TABLE 5

Characterisation data for compounds of the invention represented by formula (Ic):

(Ic)

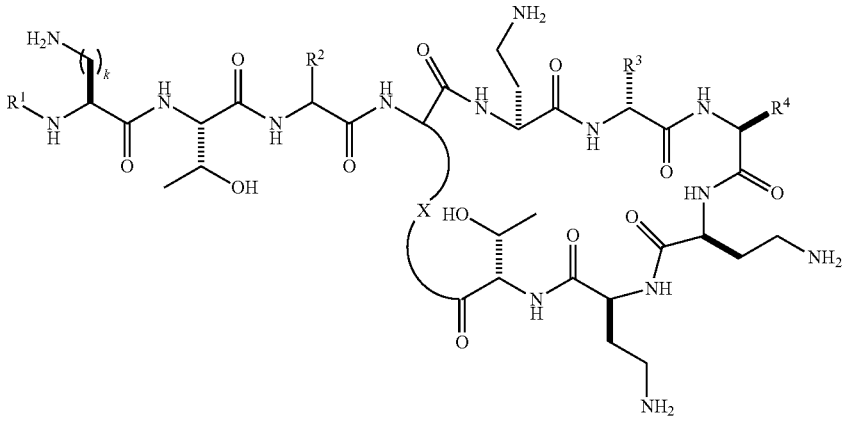

| No | $R^1$ | $R^2$ | $R^3$ | $R^4$ | X | k | Compound data |
|---|---|---|---|---|---|---|---|
| 2 | Octanoyl | D-Ser | D-Leu | Ala | Dab | 2 | Yield: 43.0 mg, Purity: (99.4%) MS Data: $[M + 2H]^{2+}$ = 551.5 |
| 3 | Octanoyl | D-Ser | D-Phe | Thr | Dab | 2 | Yield: 59.0 mg, Purity: (98.4%) MS Data: $[M + 2H]^{2+}$ = 583.4 |
| 4 | Ocatanoyl | Ser | D-Leu | Thr | Dab | 2 | Yield: 58.7 mg, Purity: (99.7%) MS Data: $[M + 2H]^{2+}$ = 566.3 |
| 5 | Octanoyl | D-Ser | D-Leu | Val | Dab | 2 | Yield: 65.5 mg, Purity: (98.9%) MS Data: $[M + 2H]^{2+}$ = 565.4 |
| 6 | Octanoyl | D-Ser | D-Leu | Ser | Dab | 2 | Yield: 53.1 mg, Purity: (99.3%) MS Data: $[M + 2H]^{2+}$ = 559.4 |
| 7 | Octanoyl | D-Ser | D-Nle | Thr | Dab | 2 | Yield: 40.0 mg, Purity: (99.2%) MS Data: $[M + 2H]^{2+}$ = 566.3 |
| 8 | Hexanoyl | D-Ser | D-Leu | Thr | Dab | 2 | Yield: 61.0 mg, Purity: (99.2%) MS Data: $[M + 2H]^{2+}$ = 552.25 |
| 9 | Decanoyl | D-Ser | D-Leu | Thr | Dab | 2 | Yield: 63.7 mg, Purity: (99.6%) MS Data: $[M + 2H]^{2+}$ = 580.3 |
| 10 | Dodec | D-Ser | D-Leu | Thr | Dab | 2 | Yield: 39.0 mg, Purity: (98.6%) MS Data: $[M + 2H]^{2+}$ = 594.30 |
| 11 | 4-BPC | D-Ser | D-Leu | Thr | Dab | 2 | Yield: 68.5 mg, Purity: (99.4%) MS Data $[M + 2H]^{2+}$ = 593.25 |
| 12 | PA | D-Ser | D-Leu | Thr | Dab | 2 | Yield: mg, Purity: (99.1%) MS Data: $[M + 2H]^{2+}$ = 562.20 |
| 13 | Octanoyl | D-Ser | D-Leu | Thr | Dab | 1 | Yield: 63.8 mg, Purity: (98.3%) MS Data: $[M + 2H]^{2+}$ = 559.25 |
| 14 | Octanoyl | D-Ser | D-Leu | Thr | Dab | 3 | Yield: 69.3 mg, Purity: (99.5%) MS Data: $[M + 2H]^{2+}$ = 573.30 |
| 15 | Octanoyl | D-Thr | D-Leu | Thr | Dab | 2 | Yield: 60.3 mg, Purity: (98.6%) MS Data: $[M + 2H]^{2+}$ = 573.3 |
| 16 | Heptanoyl | D-Ser | D-Leu | Thr | Dab | 2 | Yield: 50.0 mg, Purity: (99.3%) MS Data: $[M + 2H]^{2+}$ = 559.25 |
| 17 | Nonanoyl | D-Ser | D-Leu | Thr | Dab | 2 | Yield: 56.4 mg, Purity: (99.0%) MS Data: $[M + 2H]^{2+}$ = 573.25 |
| 18 | 3-TFMB | D-Ser | D-Leu | Abu | Dab | 2 | Yield: 15.5 mg, Purity: (97.3%) MS Data: $[M + 2H]^{2+}$ = 582.1 |
| 19 | 3-TFMB | D-Ser | D-Leu | Thr | Dab | 2 | Yield: 12.6 mg, Purity: (97.3%) MS Data: $[M + 2H]^{2+}$ = 590.05 |
| 150 | (S)-6-MO (polymyxin $D_1$) | D-Ser | D-Leu | Thr | Dab | 2 | Yield: 56.6 mg, Purity: (99.2%) MS Data: $[M + 2H]^{2+}$ = 573.3 |
| 151 | 6-MH (polymyxin $D_2$) | D-Ser | D-Leu | Thr | Dab | 2 | Yield: 47.7 mg, Purity: (96.8%) MS Data: $[M + 2H]^{2+}$ = 566.3 |

a) for $R^2$, $R^3$ $R^4$ and X, the amino acid shown in these columns is indicative of the side chain and stereochemistry at these positions; Dodec = dodecanoyl, 3-TFMB = 3-trifluoromethylbenzoyl, (S)-6-MO = (S)-6-methyloctanoyl, 6-MH = 6-methylheptanoyl, Dab = diaminobutyric acid, Phe = phenylalanine, Thr = threonine, Ala = alanine, Ser = serine, Val = valine, Nle = norleucine, Abu = 2-aminobutyric acid, D- indicates D-amino acids.

TABLE 6

Characterisation data for compounds of the invention represented by formula IIc:

(IIc)

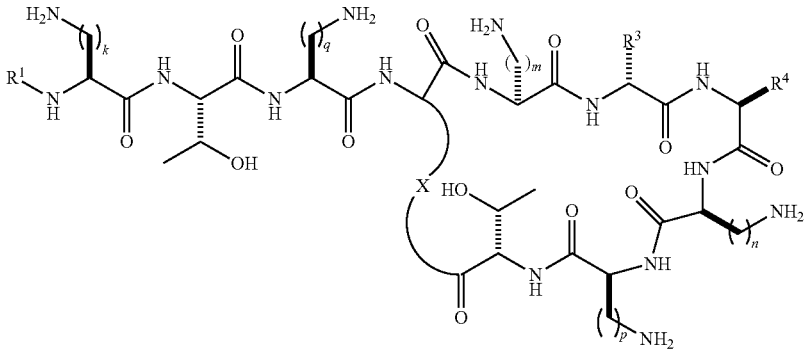

| No. | $R^1$ | $R^3$ | $R^4$ | X | k | q | m | n | p | Compound Data |
|---|---|---|---|---|---|---|---|---|---|---|
| 20 | Octanoyl | D-Leu | Thr | Dab | 2 | 2 | 2 | 2 | 2 | Yield: 54.7 mg, Purity: (98.4%) MS Data: $[M + 2H]^{2+}$ = 572.80 |
| 21 | Octanoyl | D-Leu | Ala | Dab | 2 | 2 | 2 | 2 | 2 | Yield: 57.0 mg, Purity: (98.2%) MS Data: $[M + 2H]^{2+}$ = 557.65 |
| 22 | Octanoyl | D-Phe | Thr | Dab | 2 | 2 | 2 | 2 | 2 | Yield: 54.8 mg, Purity: (99.3%) MS Data: $[M + 2H]^{2+}$ = 589.8 |
| 23 | Octanoyl | D-Leu | Val | Dab | 2 | 2 | 2 | 2 | 2 | Yield: 41.2 mg, Purity: (99.3%) MS Data: $[M + 2H]^{2+}$ = 571.80 |
| 24 | Octanoyl | D-Nle | Thr | Dab | 2 | 2 | 2 | 2 | 2 | Yield: 61.2 mg, Purity: (98.9%) MS Data: $[M + 2H]^{2+}$ = 572.80 |
| 25 | Octanoyl | D-Leu | Ser | Dab | 2 | 2 | 2 | 2 | 2 | Yield: 49.8 mg, Purity: (99.2%) MS Data: $[M + 2H]^{2+}$ = 565.75 |
| 26 | Hexanoyl | D-Leu | Thr | Dab | 2 | 2 | 2 | 2 | 2 | Yield: 73.3 mg, Purity: (99.6%) MS Data: $[M + 2H]^{2+}$ = 558.75 |
| 27 | Decanoyl | D-Leu | Thr | Dab | 2 | 2 | 2 | 2 | 2 | Yield: 64.1 mg, Purity: (98.9%) MS Data: $[M + 2H]^{2+}$ = 586.8 |
| 28 | Dodec | D-Leu | Thr | Dab | 2 | 2 | 2 | 2 | 2 | Yield: 51.0 mg, Purity: (99.6%) MS Data: $[M + 2H]^{2+}$ = 600.85 |
| 29 | 4-BPC | D-Leu | Thr | Dab | 2 | 2 | 2 | 2 | 2 | Yield: 69.0 mg, Purity: (98.8%) MS Data: $[M + 2H]^{2+}$ = 599.75 |
| 30 | PA | D-Leu | Thr | Dab | 2 | 2 | 2 | 2 | 2 | Yield: 69.3 mg, Purity: (99.1%) MS Data: $[M + 2H]^{2+}$ = 568.75 |
| 31 | Octanoyl | D-Leu | Thr | Dab | 1 | 2 | 2 | 2 | 2 | Yield: 68.9 mg, Purity: (98.9%) MS Data: $[M + 2H]^{2+}$ = 565.80 |
| 32 | Octanoyl | D-Leu | Thr | Dab | 3 | 2 | 2 | 2 | 2 | Yield: 77.4 mg, Purity: (98.5%) MS Data: $[M + 2H]^{2+}$ = 579.80 |
| 33 | Octanoyl | D-Leu | Thr | Dab | 2 | 1 | 2 | 2 | 2 | Yield: 72.2 mg, Purity: (98.8%) MS Data: $[M + 2H]^{2+}$ = 565.80 |

TABLE 6-continued

Characterisation data for compounds of the invention represented by formula IIc:

(IIc)

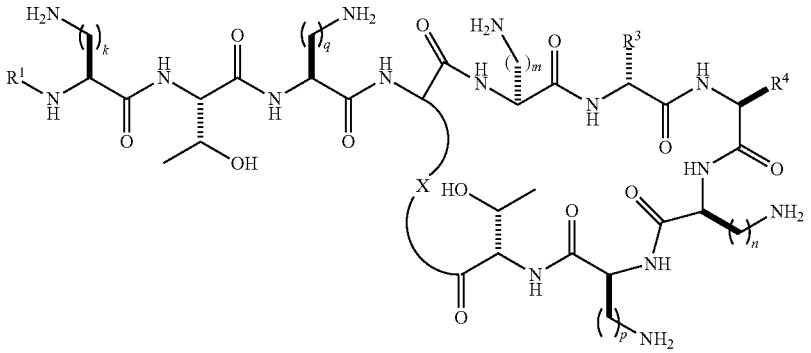

| No. | $R^1$ | $R^3$ | $R^4$ | X | k | q | m | n | p | Compound Data |
|---|---|---|---|---|---|---|---|---|---|---|
| 34 | Octanoyl | D-Leu | Thr | Dab | 2 | 3 | 2 | 2 | 2 | Yield: 57.9 mg, Purity: (98.4%) MS Data: $[M + 2H]^{2+}$ = 579.85 |
| 35 | Octanoyl | D-Leu | Ala | Dab | 2 | 1 | 2 | 2 | 2 | Yield: 59.3 mg, Purity: (98.7%) MS Data: $[M + 2H]^{2+}$ = 550.75 |
| 36 | Octanoyl | D-Leu | Val | Dab | 2 | 1 | 2 | 2 | 2 | Yield: 47.8 mg, Purity: (98.6%) MS Data: $[M + 2H]^{2+}$ = 564.80 |
| 37 | Decanoyl | D-Leu | Thr | Dab | 2 | 1 | 2 | 2 | 2 | Yield: 63.1 mg, Purity: (99.14%) MS Data: $[M + 2H]^{2+}$ = 579.75 |
| 38 | Decanoyl | D-Leu | Ala | Dab | 2 | 1 | 2 | 2 | 2 | Yield: 48.6 mg, Purity: (99.3%) MS Data: $[M + 2H]^{2+}$ = 564.8 |
| 39 | Decanoyl | D-Leu | Val | Dab | 2 | 1 | 2 | 2 | 2 | Yield: 52.9 mg, Purity: (99.3%) MS Data: $[M + 2H]^{2+}$ = 578.85 |
| 40 | Decanoyl | D-Leu | Ala | Dab | 2 | 2 | 2 | 2 | 2 | Yield: 28.5 mg, Purity: (99.6%) MS Data: $[M + 2H]^{2+}$ = 571.5 |
| 41 | Decanoyl | D-Leu | Val | Dab | 2 | 2 | 2 | 2 | 2 | Yield: 59.3 mg, Purity: (99.6%) MS Data: $[M + 2H]^{2+}$ = 585.80 |
| 42 | Heptanoyl | D-Leu | Thr | Dab | 2 | 2 | 2 | 2 | 2 | Yield: 67.0 mg, Purity: (98.9%) MS Data: $[M + 2H]^{2+}$ = 568.80 |
| 43 | Nonanoyl | D-Leu | Thr | Dab | 2 | 2 | 2 | 2 | 2 | Yield: 35.0 mg, Purity: (98.9%) MS Data: $[M + 2H]^{2+}$ = 579.75 |
| 44 | Heptanoyl | D-Leu | Thr | Dab | 2 | 1 | 2 | 2 | 2 | Yield: 59.8 mg, Purity: (99.1%) MS Data: $[M + 2H]^{2+}$ = 558.70 |
| 45 | Octanoyl | D-Leu | Aib | Dab | 2 | 1 | 2 | 2 | 2 | Yield: 67.5 mg, Purity: (97.7%) MS Data: $[M + 2H]^{2+}$ = 557.75 |
| 46 | Octanoyl | D-Leu | Abu | Dab | 2 | 1 | 2 | 2 | 2 | Yield: 52.5 mg, Purity: (99.0%) MS Data: $[M + 2H]^{2+}$ = 557.75 |
| 47 | Octanoyl | D-Leu | Tle | Dab | 2 | 1 | 2 | 2 | 2 | Yield: 45.3 mg, Purity: (97.4%) MS Data: $[M + 2H]^{2+}$ = 571.80 |

TABLE 6-continued

Characterisation data for compounds of the invention represented by formula IIc:

(IIc)

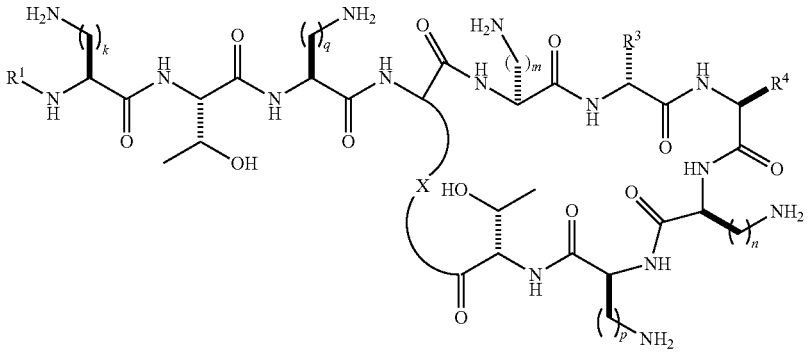

| No. | $R^1$ | $R^3$ | $R^4$ | X | k | q | m | n | p | Compound Data |
|---|---|---|---|---|---|---|---|---|---|---|
| 48 | Octanoyl | D-Leu | Thr | Dab | 1 | 1 | 2 | 2 | 2 | Yield: 57.5 mg, Purity: (98.9%) MS Data: $[M + 2H]^{2+}$ = 558.75 |
| 49 | Octanoyl | D-Nva | Thr | Dab | 2 | 1 | 2 | 2 | 2 | Yield: 53.0 mg, Purity: (99.3%) MS Data: $[M + 2H]^{2+}$ = 558.75 |
| 50 | Octanoyl | D-Leu | Thr | Dab | 2 | 1 | 2 | 2 | 1 | Yield: 63.8 mg, Purity: (99.1%) MS Data: $[M + 2H]^{2+}$ = 558.75 |
| 51 | Octanoyl | D-Leu | Thr | Dab | 2 | 1 | 2 | 1 | 2 | Yield: 64.9 mg, Purity: (98.8%) MS Data: $[M + 2H]^{2+}$ = 558.75 |
| 52 | Octanoyl | D-Leu | Thr | Dab | 2 | 1 | 1 | 2 | 2 | Yield: 43.8 mg, Purity: (99.0%) MS Data: $[M + 2H]^{2+}$ = 558.75 |
| 53 | Octanoyl | D-Leu | Thr | Dab | 2 | 1 | 2 | 2 | 3 | Yield: 52.0 mg, Purity: (96.7%) MS Data: $[M + 2H]^{2+}$ = 572.75 |
| 54 | Octanoyl | D-Leu | Thr | Dab | 2 | 1 | 2 | 3 | 2 | Yield: 45.1 mg, Purity: (99.3%) MS Data: $[M + 2H]^{2+}$ = 572.75 |
| 55 | Octanoyl | D-Leu | Thr | Dab | 2 | 1 | 3 | 2 | 2 | Yield: 60.9 mg, Purity: (99.6%) MS Data: $[M + 2H]^{2+}$ = 572.75 |
| 56 | 4-TFMB | D-Leu | Thr | Dab | 2 | 1 | 2 | 2 | 2 | Yield: 52.5 mg, Purity: (99.1%) MS Data: $[M + 2H]^{2+}$ = 588.75 |
| 57 | 3,4-DCB | D-Leu | Thr | Dab | 2 | 1 | 2 | 2 | 2 | Yield: 52.0 mg, Purity: (99.1%) MS Data: $[M + H]^{+}$ = 596.75 |
| 58 | Nonanoyl | D-Leu | Thr | Dab | 2 | 1 | 2 | 2 | 2 | Yield: 54.0 mg, Purity: (99.3%) MS Data: $[M + 2H]^{2+}$ = 572.7 |
| 59 | Nonanoyl | D-Leu | Abu | Dab | 2 | 1 | 2 | 2 | 2 | Yield: 66.0 mg, Purity: (98.3%) MS Data: $[M + 2H]^{2+}$ = 564.85 |
| 60 | Octanoyl | D-Leu | Abu | Dab | 2 | 2 | 2 | 2 | 2 | Yield: 23.0 mg, Purity: (99.6%) MS Data: $[M + 2H]^{2+}$ = 564.75 |
| 61 | 3-CPA | D-Leu | Thr | Dab | 2 | 1 | 2 | 2 | 2 | Yield: 71.9 mg, Purity: (98.5%) MS Data: $[M + 2H]^{2+}$ = 578.9 |

TABLE 6-continued

Characterisation data for compounds of the invention represented by formula IIc:

(IIc)

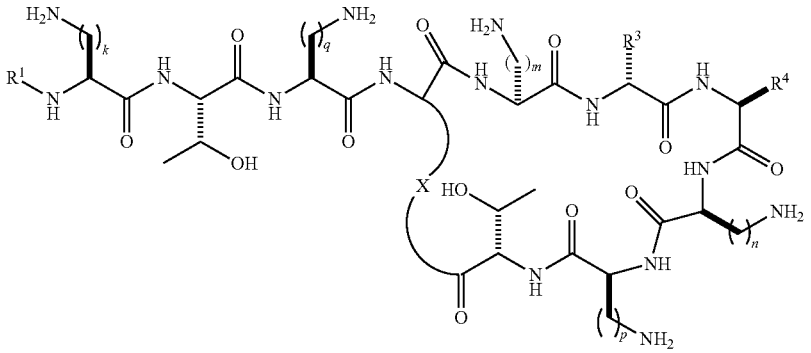

| No. | $R^1$ | $R^3$ | $R^4$ | X | k | q | m | n | p | Compound Data |
|---|---|---|---|---|---|---|---|---|---|---|
| 62 | 2,4-DCPA | D-Leu | Thr | Dab | 2 | 1 | 2 | 2 | 2 | Yield: 74.9 mg, Purity: (98.9%) MS Data: $[M + 2H]^{2+}$ = 595.8 |
| 63 | Heptanoyl | D-Leu | Ala | Dab | 2 | 1 | 2 | 2 | 2 | Yield: 65.4 mg, Purity: (97.9%) MS Data: $[M + 2H]^{2+}$ = 543.80 |
| 64 | Heptanoyl | D-Leu | Abu | Dab | 2 | 1 | 2 | 2 | 2 | Yield: 59.8 mg, Purity: (99.1%) MS Data: $[M + 2H]^{2+}$ = 550.80 |
| 65 | 6-MH | D-Leu | Ala | Dab | 2 | 1 | 2 | 2 | 2 | Yield: 67.4 mg, Purity: (98.7%) MS Data: $[M + 2H]^{2+}$ = 550.75 |
| 66 | 6-MH | D-Leu | Abu | Dab | 2 | 1 | 2 | 2 | 2 | Yield: 68.0 mg, Purity: (97.9%) MS Data: $[M + 2H]^{2+}$ = 557.75 |
| 67 | Hexanoyl | D-Leu | Ala | Dab | 2 | 1 | 2 | 2 | 2 | Yield: 65.9 mg, Purity: (99.2%) MS Data: $[M + 2H]^{2+}$ = 536.75 |
| 68 | Hexanoyl | D-Leu | Abu | Dab | 2 | 1 | 2 | 2 | 2 | Yield: 69.9 mg, Purity: (99.4%) MS Data: $[M + 2H]^{2+}$ = 543.80 |
| 69 | Octanoyl | D-Nva | Abu | Dab | 2 | 1 | 2 | 2 | 2 | Yield: 57.9 mg, Purity: (98.9%) MS Data: $[M + 2H]^{2+}$ = 550.8 |
| 70 | 2,4-DCPA | D-Leu | Abu | Dab | 2 | 1 | 2 | 2 | 2 | Yield: 70.7 mg, Purity: (98.5%) MS Data: $[M + 2H]^{2+}$ = 596.85 |
| 71 | 3,4-DCB | D-Leu | Abu | Dab | 2 | 1 | 2 | 2 | 2 | Yield: 60.7 mg, Purity: (98.2%) MS Data: $[M + 2H]^{2+}$ = 581.65 |
| 72 | 2-CB | D-Leu | Abu | Dab | 2 | 1 | 2 | 2 | 2 | Yield: 61.0 mg, Purity: (99.2%) MS Data: $[M + 2H]^{2+}$ = 563.95 |
| 73 | 2-FB | D-Leu | Abu | Dab | 2 | 1 | 2 | 2 | 2 | Yield: 61.4 mg, Purity: (97.8%) MS Data: $[M + 2H]^{2+}$ = 555.70 |
| 74 | 4-TFMB | D-Leu | Abu | Dab | 2 | 1 | 2 | 2 | 2 | Yield: 67.3 mg, Purity: (97.7%) MS Data: $[M + 2H]^{2+}$ = 58.75 |
| 75 | 2-MB | D-Leu | Abu | Dab | 2 | 1 | 2 | 2 | 2 | Yield: 62.9 mg, Purity: (98.1%) MS Data: $[M + 2H]^{2+}$ = 553.75 |

TABLE 6-continued

Characterisation data for compounds of the invention represented by formula IIc:

(IIc)

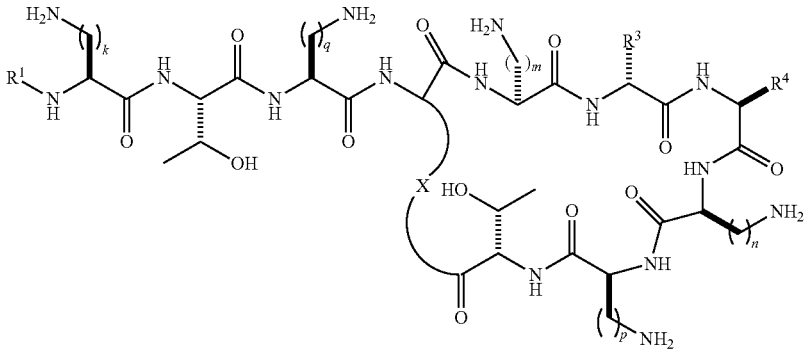

| No. | $R^1$ | $R^3$ | $R^4$ | X | k | q | m | n | p | Compound Data |
|---|---|---|---|---|---|---|---|---|---|---|
| 76 | 2-MPA | D-Leu | Abu | Dab | 2 | 1 | 2 | 2 | 2 | Yield: 67.2 mg, Purity: (98.8%) MS Data: $[M + 2H]^{2+}$ = 560.75 |
| 77 | 4-CPA | D-Leu | Abu | Dab | 2 | 1 | 2 | 2 | 2 | Yield: 67.6 mg, Purity: (99.2%) MS Data: $[M + 2H]^{2+}$ = 570.90 |
| 78 | PA | D-Leu | Abu | Dab | 2 | 1 | 2 | 2 | 2 | Yield: 43.9 mg, Purity: (98.3%) MS Data: $[M + 2H]^{2+}$ = 553.75 |
| 79 | 3-CPA | D-Leu | Abu | Dab | 2 | 1 | 2 | 2 | 2 | Yield: 76.2 mg, Purity: (97.9%) MS Data: $[M + 2H]^{2+}$ = 570.60 |
| 80 | 4-MPA | D-Leu | Abu | Dab | 2 | 1 | 2 | 2 | 2 | Yield: 65.2 mg, Purity: (98.9%) MS Data: $[M + 2H]^{2+}$ = 560.80 |
| 81 | 3,4-DCPA | D-Leu | Abu | Dab | 2 | 1 | 2 | 2 | 2 | Yield: 60.7 mg, Purity: (99.1%) MS Data: $[M + 2H]^{2+}$ = 588.55 |
| 82 | 2,4-DCB | D-Leu | Abu | Dab | 2 | 1 | 2 | 2 | 2 | Yield: 64.3 mg, Purity: (98.9%) MS Data: $[M + 2H]^{2+}$ = 581.65 |
| 83 | 3,4-DMB | D-Leu | Abu | Dab | 2 | 1 | 2 | 2 | 2 | Yield: 63.5 mg, Purity: (98.7%) MS Data: $[M + 2H]^{2+}$ = 560.75 |
| 84 | 2-CPA | D-Leu | Abu | Dab | 2 | 1 | 2 | 2 | 2 | Yield: 61.4 mg, Purity: (99.4%) MS Data: $[M + 2H]^{2+}$ = 570.60 |
| 85 | 2-FPA | D-Leu | Abu | Dab | 2 | 1 | 2 | 2 | 2 | Yield: 60.4 mg, Purity: (99.5%) MS Data: $[M + 2H]^{2+}$ = 562.75 |
| 86 | 3-FB | D-Leu | Abu | Dab | 2 | 1 | 2 | 2 | 2 | Yield: 62.3 mg, Purity: (98.2%) MS Data: $[M + 2H]^{2+}$ = 555.70 |
| 87 | 3-MB | D-Leu | Abu | Dab | 2 | 1 | 2 | 2 | 2 | Yield: 64.8 mg, Purity: (98.1%) MS Data: $[M + 2H]^{2+}$ = 553.75 |
| 88 | 3-CB | D-Leu | Abu | Dab | 2 | 1 | 2 | 2 | 2 | Yield: 59.3 mg, Purity: (97.3%) MS Data: $[M + 2H]^{2+}$ = 564.0 |
| 89 | 2,4-DMB | D-Leu | Abu | Dab | 2 | 1 | 2 | 2 | 2 | Yield: 63.0 mg, Purity: (98.8%) MS Data: $[M + 2H]^{2+}$ = 560.80 |

TABLE 6-continued

Characterisation data for compounds of the invention represented by formula IIc:

(IIc)

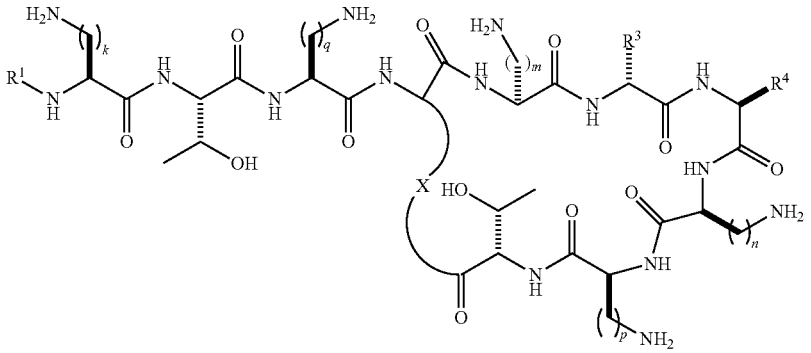

| No. | $R^1$ | $R^3$ | $R^4$ | X | k | q | m | n | p | Compound Data |
|---|---|---|---|---|---|---|---|---|---|---|
| 90 | 2,3-DCB | D-Leu | Abu | Dab | 2 | 1 | 2 | 2 | 2 | Yield: 67.9 mg, Purity: (99.1%) MS Data: $[M + 2H]^{2+}$ = 581.60 |
| 91 | 2,3-DMB | D-Leu | Abu | Dab | 2 | 1 | 2 | 2 | 2 | Yield: 60.6 mg, Purity: (98.5%) MS Data: $[M + 2H]^{2+}$ = 560.80 |
| 92 | 2,4,6-TMB | D-Leu | Abu | Dab | 2 | 1 | 2 | 2 | 2 | Yield: 22.0 mg, Purity: (98.2%) MS Data: $[M + 2H]^{2+}$ = 567.80 |
| 93 | 3,5-DMB | D-Leu | Abu | Dab | 2 | 1 | 2 | 2 | 2 | Yield: 57.1 mg, Purity: (99.0%) MS Data: $[M + 2H]^{2+}$ = 560.80 |
| 94 | 4-CB | D-Leu | Abu | Dab | 2 | 1 | 2 | 2 | 2 | Yield: 62.1 mg, Purity: (98.4%) MS Data: $[M + 2H]^{2+}$ = 563.95 |
| 95 | 2,4,6-TCB | D-Leu | Abu | Dab | 2 | 1 | 2 | 2 | 2 | Yield: 58.0 mg, Purity: (98.7%) MS Data: $[M + 2H]^{2+}$ = 598.70 |
| 96 | 3,5-DCB | D-Leu | Abu | Dab | 2 | 1 | 2 | 2 | 2 | Yield: 63.8 mg, Purity: (98.6%) MS Data: $[M + 2H]^{2+}$ = 581.65 |
| 97 | 3,5-BTFMB | D-Leu | Abu | Dab | 2 | 1 | 2 | 2 | 2 | Yield: 57.0 mg, Purity: (98.9%) MS Data: $[M + 2H]^{2+}$ = 614.75 |
| 98 | 4-MB | D-Leu | Abu | Dab | 2 | 1 | 2 | 2 | 2 | Yield: 60.0 mg, Purity: (98.1%) MS Data: $[M + 2H]^{2+}$ = 553.80 |
| 99 | 4-IPB | D-Leu | Abu | Dab | 2 | 1 | 2 | 2 | 2 | Yield: 51.8 mg, Purity: (97.9%) MS Data: $[M + 2H]^{2+}$ = 567.80 |
| 100 | 4-EB | D-Leu | Abu | Dab | 2 | 1 | 2 | 2 | 2 | Yield: 54.8 mg, Purity: (99.5%) MS Data: $[M + 2H]^{2+}$ = 560.75 |
| 101 | 2-C-4-MB | D-Leu | Abu | Dab | 2 | 1 | 2 | 2 | 2 | Yield: 37.0 mg, Purity: (98.6%) MS Data: $[M + 2H]^{2+}$ = 570.65 |
| 102 | 3-F-4-MB | D-Leu | Abu | Dab | 2 | 1 | 2 | 2 | 2 | Yield: 61.5 mg, Purity: (98.7%) MS Data: $[M + 2H]^{2+}$ = 562.75 |
| 103 | 3,4-DMPA | D-Leu | Abu | Dab | 2 | 1 | 2 | 2 | 2 | Yield: 64.7 mg, Purity: (97.2%) MS Data: $[M + 2H]^{2+}$ = 567.80 |

TABLE 6-continued

Characterisation data for compounds of the invention represented by formula IIc:

(IIc)

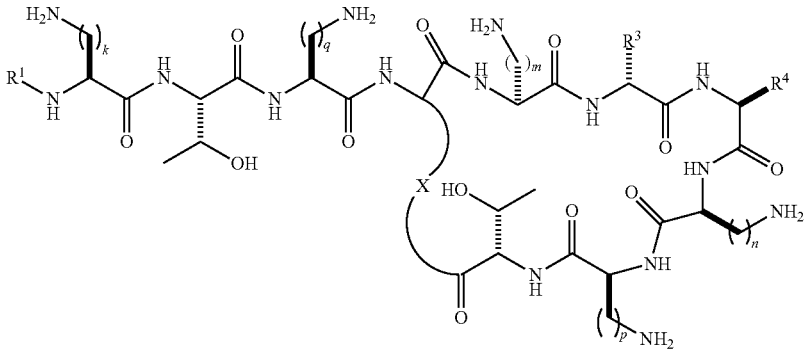

| No. | $R^1$ | $R^3$ | $R^4$ | X | k | q | m | n | p | Compound Data |
|---|---|---|---|---|---|---|---|---|---|---|
| 104 | 4-C-3-MB | D-Leu | Abu | Dab | 2 | 1 | 2 | 2 | 2 | Yield: 62.0 mg, Purity: (97.6%) MS Data: $[M + 2H]^{2+}$ = 570.90 |
| 105 | 3-C-4-MB | D-Leu | Abu | Dab | 2 | 1 | 2 | 2 | 2 | Yield: 64.0 mg, Purity: (98.7%) MS Data: $[M + 2H]^{2+}$ = 570.95 |
| 106 | 3-TFMB | D-Leu | Abu | Dab | 2 | 1 | 2 | 2 | 2 | Yield: 60.0 mg, Purity: (97.6%) MS Data: $[M + 2H]^{2+}$ = 580.75 |
| 107 | 4-C-3-FB | D-Leu | Abu | Dab | 2 | 1 | 2 | 2 | 2 | Yield: 62.7 mg, Purity: (97.5%) MS Data: $[M + 2H]^{2+}$ = 572.90 |
| 108 | 3-F-5-TFMB | D-Leu | Abu | Dab | 2 | 1 | 2 | 2 | 2 | Yield: 66.0 mg, Purity: (98.5%) MS Data: $[M + 2H]^{2+}$ = 589.75 |
| 109 | 2-C-4-TFMB | D-Leu | Abu | Dab | 2 | 1 | 2 | 2 | 2 | Yield: 67.5 mg, Purity: (97.3%) MS Data: $[M + 2H]^{2+}$ = 597.60 |
| 110 | 3-C-4-FB | D-Leu | Abu | Dab | 2 | 1 | 2 | 2 | 2 | Yield: 65.4 mg, Purity: (98.1%) MS Data: $[M + 2H]^{2+}$ = 572.90 |
| 111 | 3-F-4-TFMB | D-Leu | Abu | Dab | 2 | 1 | 2 | 2 | 2 | Yield: 61.3 mg, Purity: (97.5%) MS Data: $[M + 2H]^{2+}$ = 589.75 |
| 112 | 4-C-3-TFMB | D-Leu | Abu | Dab | 2 | 1 | 2 | 2 | 2 | Yield: 60.0 mg, Purity: (96.9%) MS Data: $[M + 2H]^{2+}$ = 598.00 |
| 113 | 4-M-3-TFMB | D-Leu | Abu | Dab | 2 | 1 | 2 | 2 | 2 | Yield: 65.2 mg, Purity: (96.5%) MS Data: $[M + 2H]^{2+}$ = 587.75 |
| 114 | 3-C-5-MB | D-Leu | Abu | Dab | 2 | 1 | 2 | 2 | 2 | Yield: 25.4 mg, Purity: (96.9%) MS Data: $[M + 2H]^{2+}$ = 570.95 |
| 115 | 3-C-4-TFMB | D-Leu | Abu | Dab | 2 | 1 | 2 | 2 | 2 | Yield: 19.2 mg, Purity: (97.0%) MS Data: $[M + 2H]^{2+}$ = 597.95 |
| 116 | 3-C-5-FB | D-Leu | Abu | Dab | 2 | 1 | 2 | 2 | 2 | Yield: 67.7 mg, Purity: (97.4%) MS Data: $[M + 2H]^{2+}$ = 572.95 |
| 117 | 3,5-DCB | D-Leu | Ala | Dab | 2 | 1 | 2 | 2 | 2 | Yield: 17.6 mg, Purity: (95.9%) MS Data: $[M + 2H]^{2+}$ = 574.55 |
| 118 | 3,5-DCB | D-Leu | Thr | Dab | 2 | 1 | 2 | 2 | 2 | Yield: 11.7 mg, Purity: (97.1%) MS Data: $[M + 2H]^{2+}$ = 589.50 |
| 119 | 3-M-4-TFMB | D-Leu | Abu | Dab | 2 | 1 | 2 | 2 | 2 | Yield: 60.2 mg, Purity: (97.4%) MS Data: $[M + 2H]^{2+}$ = 587.85 |
| 120 | 3-M-5-TFMB | D-Leu | Abu | Dab | 2 | 1 | 2 | 2 | 2 | Yield: 65.2 mg, Purity: (97.1%) MS Data: $[M + 2H]^{2+}$ = 587.75 |
| 121 | 3-TFMB | D-Nle | Abu | Dab | 2 | 1 | 2 | 2 | 2 | Yield: 62.4 mg, Purity: (97.5%) MS Data: $[M + 2H]^{2+}$ = 580.75 |

TABLE 6-continued

Characterisation data for compounds of the invention represented by formula IIc:

(IIc)

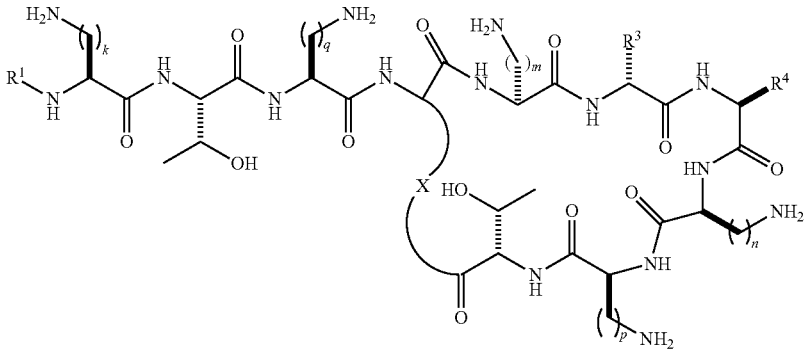

| No. | $R^1$ | $R^3$ | $R^4$ | X | k | q | m | n | p | Compound Data |
|---|---|---|---|---|---|---|---|---|---|---|
| 122 | 3-TFMB | D-Phe | Abu | Dab | 2 | 1 | 2 | 2 | 2 | Yield: 65.6 mg, Purity: (97.2%) MS Data: $[M + 2H]^{2+}$ = 597.75 |
| 123 | 3-TFMB | D-Nle | Thr | Dab | 2 | 1 | 2 | 2 | 2 | Yield: 52.4 mg, Purity: (97.5%) MS Data: $[M + 2H]^{2+}$ = 588.70 |
| 124 | 3-TFMB | D-Phe | Thr | Dab | 2 | 1 | 2 | 2 | 2 | Yield: 63.6 mg, Purity: (97.2%) MS Data: $[M + 2H]^{2+}$ = 605.70 |
| 125 | 3-TFMB | D-Nle | Ala | Dab | 2 | 1 | 2 | 2 | 2 | Yield: 62.3 mg, Purity: (97.8%) MS Data: $[M + 2H]^{2+}$ = 573.70 |
| 126 | 3-TFMB | D-Phe | Ala | Dab | 2 | 1 | 2 | 2 | 2 | Yield: 61.6 mg, Purity: (97.9%) MS Data: $[M + 2H]^{2+}$ = 590.70 |
| 127 | 4-TFMPA | D-Leu | Abu | Dab | 2 | 1 | 2 | 2 | 2 | Yield: 84.6 mg, Purity: (98.6%) MS Data: $[M + 2H]^{2+}$ = 595.70 |
| 128 | Octanoyl | D-Phe | Ala | Dab | 2 | 1 | 2 | 2 | 2 | Yield: 62.6 mg, Purity: 97.1%) MS Data: $[M + 2H]^{2+}$ = 567.80 |
| 129 | Octanoyl | D-Phe | Thr | Dab | 2 | 1 | 2 | 2 | 2 | Yield: 56.8 mg, Purity: (97.7%) MS Data: $[M + 2H]^{2+}$ = 582.80 |
| 130 | Octanoyl | D-Phe | Abu | Dab | 2 | 1 | 2 | 2 | 2 | Yield: 66.3 mg, Purity: (97.3%) MS Data: $[M + 2H]^{2+}$ = 574.75 |
| 131 | Heptanoyl | D-Phe | Abu | Dab | 2 | 1 | 2 | 2 | 2 | Yield: 66.4 mg, Purity: (98.8%) MS Data: $[M + 2H]^{2+}$ = 567.75 |
| 132 | Nonanoyl | D-Leu | Ala | Dab | 2 | 1 | 2 | 2 | 2 | Yield: 62.2 mg, Purity: (97.7%) MS Data: $[M + 2H]^{2+}$ = 557.80 |
| 133 | 3,4,5-TFB | D-Leu | Abu | Dab | 2 | 1 | 2 | 2 | 2 | Yield: 63.3 mg, Purity: (97.8%) MS Data: $[M + 2H]^{2+}$ = 573.70 |
| 134 | 4-C-2-FB | D-Leu | Abu | Dab | 2 | 1 | 2 | 2 | 2 | Yield: 70.3 mg, Purity: (97.7%) MS Data: $[M + 2H]^{2+}$ = 572.60 |
| 135 | 2-C-4-FB | D-Leu | Abu | Dab | 2 | 1 | 2 | 2 | 2 | Yield: 66.2 mg, Purity: (98.0%) MS Data: $[M + 2H]^{2+}$ = 572.90 |
| 136 | 4-C-2-TFMB | D-Leu | Abu | Dab | 2 | 1 | 2 | 2 | 2 | Yield: 74.2 mg, Purity: (98.1%) MS Data: $[M + 2H]^{2+}$ = 597.60 |
| 137 | 2-F-4-TFMB | D-Leu | Abu | Dab | 2 | 1 | 2 | 2 | 2 | Yield: 56.7 mg, Purity: (98.2%) MS Data: $[M + 2H]^{2+}$ = 589.75 |
| 138 | 3-BPC | D-Leu | Abu | Dab | 2 | 1 | 2 | 2 | 2 | Yield: 62.0 mg, Purity: (97.5%) MS Data: $[M + 2H]^{2+}$ = 584.80 |
| 139 | (S,R)-6-MO | D-Leu | Abu | Dab | 2 | 1 | 2 | 2 | 2 | Yield: 54.8 mg, Purity: (98.6%) MS Data: $[M + 2H]^{2+}$ = 564.85 |

TABLE 6-continued

Characterisation data for compounds of the invention represented by formula IIc:

(IIc)

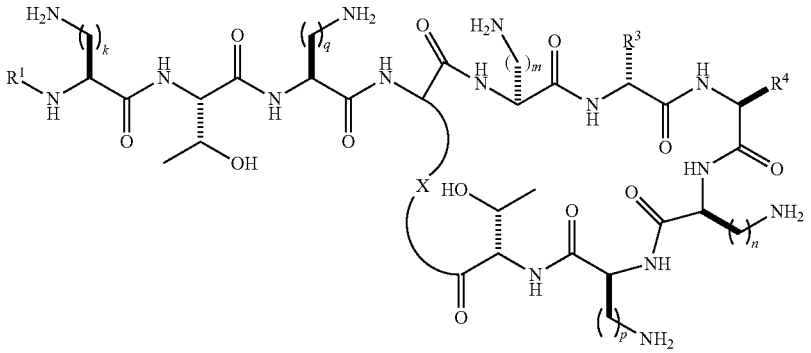

| No. | $R^1$ | $R^3$ | $R^4$ | X | k | q | m | n | p | Compound Data |
|---|---|---|---|---|---|---|---|---|---|---|
| 140 | Octanoyl | D-Phe | Aib | Dab | 2 | 1 | 2 | 2 | 2 | Yield: 68.7 mg, Purity: (97.6%) MS Data: $[M + 2H]^{2+}$ = 574.80 |
| 141 | 3-TFMB | D-Leu | Abu | Dab | 3 | 1 | 2 | 2 | 2 | Yield: 74.0 mg, Purity: (97.1%) MS Data: $[M + 2H]^{2+}$ = 587.70 |
| 142 | 4-BPC | D-Leu | Abu | Dab | 2 | 1 | 2 | 2 | 2 | Yield: 69.3 mg, Purity: (97.3%) MS Data: $[M + 2H]^{2+}$ = 584.80 |
| 143 | Nonanoyl | D-Phe | Ser | Dab | 2 | 1 | 2 | 2 | 2 | Yield: 36.2 mg, Purity: (97.3%) MS Data: $[M + 2H]^{2+}$ = 582.85 |
| 144 | 4-Cl-BP-4-C | D-Leu | Ala | Dab | 2 | 1 | 2 | 2 | 2 | Yield: 56.4 mg, Purity: (96.2%) MS Data: $[M + 2H]^{2+}$ = 595.00 |
| 145 | 3-PP | D-Leu | Abu | Dab | 2 | 1 | 2 | 2 | 2 | Yield: 55.2 mg, Purity: (97.3%) MS Data: $[M + 2H]^{2+}$ = 560.80 |
| 146 | 4-PB | D-Leu | Ala | Dab | 2 | 1 | 2 | 2 | 2 | Yield: 69.8 mg, Purity: (97.9%) MS Data: $[M + 2H]^{2+}$ = 560.80 |
| 147 | 2,4-DCB | D-Leu | Abu | Dab | 2 | 3 | 2 | 2 | 2 | Yield: 67.8 mg, Purity: (97.2%) MS Data: $[M + 2H]^{2+}$ = 595.65 |
| 148 | 2,4-DCPS | D-Leu | Abu | Dab | 2 | 1 | 2 | 2 | 2 | Yield: 10.1 mg, Purity: (94.0%) MS Data: $[M + 2H]^{2+}$ = 599.6 |
| 149 | Octanoyl | D-Leu | Thr | Orn | 2 | 2 | 2 | 2 | 2 | Yield: 54.0 mg, Purity: (98.5%) MS Data: $[M + 2H]^{2+}$ = 579.75 |
| 152 | (S)-6-MO (polymyxin $M_1$) | D-Leu | Thr | Dab | 2 | 2 | 2 | 2 | 2 | Yield: 40.0 mg, Purity: (97.4%) MS Data: $[M + 2H]^{2+}$ = 579.65 |
| 153 | 6-MH (Polymyxin $M_2$) | D-Leu | Thr | Dab | 2 | 2 | 2 | 2 | 2 | Yield: 47.7 mg, Purity: (96.9%) MS Data: $[M + 2H]^{2+}$ = 572.65 |

for $R^3$, $R^4$ and X, the amino acid shown in these columns is indicative of the side chain and stereochemistry at these positions; Dodec = dodecanoyl, 4-BPC = 4-biphenylcarboxyl, PA = phenylacetyl, 6-MH = 6-methylheptanoyl, 4-TFMPA = 4-trifluoromethylphenylacetyl, 2-MB = 2-methylbenzoyl, 3-MB = 3-methylbenzoyl, 4-MB = 4-methylbenzoyl, 3-F-4-MB = 3-fluoro-4-methylbenzoyl, 4-C-3-MB = 4-chloro-3-methylbenzoyl, 3-C-4-MB = 3-chloro-4-methylbenzoyl, 3-C-5-MB = 3-chloro-5-methylbenzoyl, 2-FPA = 2-fluorophenylacetyl, 3-TFMB = 3-trifluoromethylbenzoyl, 4-TFMB = 4-trifluoromethylbenzoyl, 2-C-4-TFMB = 2-chloro-4-trifluoromethylbenzoyl, 4-C-3-TFMB = 4-chloro-3-trifluoromethylbenzoyl, 3-C-4-TFMB = 3-chloro-4-trifluoromethylbenzoyl, 3-F-4-TFMB = 3-fluoro-4-trifluoromethylbenzoyl, 3-F-5-TFMB = 3-fluoro-5-trifluoromethylbenzoyl, 4-M-3-TFMB = 4-methyl-3-trifluoromethylbenzoyl, 3-M-4-TFMB = 3-methyl-4-trifluoromethylbenzoyl, 3-M-5-TFMB = 3-methyl-5-trifluoromethylbenzoyl, 2-F-4-TFMB = 2-fluoro-4-trifluoromethylbenzoyl, 3,4,5-TFMB = 3,4,5-trifluoromethylbenzoyl, 4-C-2-TFMB = 4-chloro-2-trifluoromethylbenzoyl, 3,5-BTFMB = 3,5-bis(trifluoromethyl)benzoyl, 2,4,6-TMB = 2,4,6-trimethylbenzoyl, 2,3-DMB = 2,3-dimethylbenzoyl, 2,4-DMB = 2,4-dimethylbenzoyl, 3,4-DMB = 3,4-dimethylbenzoyl, 3,5-DMB = 3,5-dimethylbenzoyl, 2-C-4-MB = 2-chloro-4-methylbenzoyl, 4-EB = 4-ethylbenzoyl, 4-IPB = 4-Isopropylbenzoyl, 2,4-DCPA = 2,4-dichlorophenylacetyl, 3,4-DCPA = 3,4-dichlorophenylacetyl, 2-CPA = 2-chlorophenylacetyl, 3-CPA = 3-chlorophenylacetyl, 4-CPA = 4-chlorophenylacetyl, 2-CB = 2-chlorobenzoyl, 3-CB = 3-chlorobenzoyl, 4-CB = 4-chlorobenzoyl, 2,3-DCB = 2,3-dichlorobenzoyl, 2,4-DCB = 2,4-dichlorobenzoyl, 3,4-DCB = 3,4-dichlorobenzoyl, 3,5-DCB = 3,5-dichlorobenzoyl, 2,4,6-TCB = 2,4,6-trichlorobenzoyl, 2-FB = 2-fluorobenzoyl, 3-FB = 3-fluorobenzoyl, 2-C-4-FB = 2-chloro-4-fluorobenzoyl, 3-C-4-FB = 3-Chloro-4-fluorobenzoyl, 3-C-5-FB = 3-chloro-5-fluorobenzoyl, 4-C-2-FB = 4-chloro-2-fluorobenzoyl, 4-C-3-FB = 4-chloro-3-fluorobenzoyl, 2-MPA = 2-methylphenylacetyl, 4-MPA = 4-methylphenylacetyl, 3,4-DMPA = 3,4-dimethylphenylacetyl, (S,R)-6-MO = (S,R)-6-methyloctanoyl, (S)-6-MO = (S)-6-methyloctanoyl, 3-BPC = 3-biphenylcarboxyl, 4-Cl-BP-4-C = 4-chloro-biphenyl-4-carboxyl, 3-PP = 3-phenylproponyl, 4-PB = 4-phenylbutanoyl, 2,4-DCPS = 2,4-dichlorophenylsulfonyl, Dab = diaminobutyric acid, , Tle = t-butylglycine, Aib = aminoisobutyric acid, Abu = 2-aminobutyric acid, Phe = phenylalanine, Thr = threonine, Ala = alanine, Ser = serine, Val = valine, Nva = norvaline, Nle = norleucine, Orn = ornithine, D- indicates D-amino acids.

Example 2. Measurements of Minimum Inhibitory Concentrations (MICs)

MICs of the lipopeptides (trifluoroacetic acid salt, TFA) were determined by broth microdilution in cation-adjusted Mueller-Hinton broth (CAMHB) (Oxoid Australia, Thebarton, SA, Australia) according to Clinical and Laboratory Standards Institute standards (Clinical and Laboratory Standards Institute. Performance standards for antimicrobial susceptibility testing; eighteenth informational supplement M100-S18. Wayne, Pa., 2008). Polymyxin B (sulphate) was employed as control. Gram-negative bacteria were examined for compounds 1-153 as well as for a 1:1 combination of compounds 1 and 20: for (1) Pseudomonas aeruginosa, 3 polymyxin-susceptible isolates; (2) Acinetobacter baumannii, 3 polymyxin-susceptible isolates; (3) Klebsiella pneumoniae, 2 polymyxin-susceptible isolates; (4) Enterobacter cloacae, 3 polymyxin-susceptible isolates. The results are illustrated in Table 7.

TABLE 7

Minimum inhibitory concentrations (mg/L) for compounds 1-153

| | Pa | | | Ab | | | Kp | | Ec | | |
|---|---|---|---|---|---|---|---|---|---|---|---|
| Compound | ATCC 27853 | FADDI-PA022 | FADDI-PA025 | ATCC 19606 | FADDI-AB034 | A ATCC 17978 | ATCC 13883 | FADDI-KP032 | FADDI-EC006 | FADDI-EC001 | FADDI-EC003 |
| Colistin | 1 | 1 | 2 | 1 | 0.5 | 0.5 | 1 | 1 | <0.125 | 0.25 | <0.125 |
| Polymyxin B | 1 | 1 | 1 | 1 | 0.5 | 1 | 1 | <0.125 | 0.5 | 0.25 | 0.5 |
| 1 | 4 | 4 | >32 | 1 | 0.25 | 0.25 | 1 | <0.125 | 0.5 | <0.125 | <0.125 |
| 2 | 8 | 8 | >32 | 0.5 | 0.5 | 0.5 | 1 | 0.5 | 0.5 | <0.125 | <0.125 |
| 3 | 4 | 4 | >32 | 0.25 | <0.125 | <0.125 | 2 | <0.125 | 0.25 | 0.5 | <0.125 |
| 4 | 4 | 8 | >32 | 8 | 4 | 8 | 32 | 1 | 1 | 0.5 | 0.25 |
| 5 | 2 | 4 | 16 | <0.125 | 0.25 | <0.125 | 1 | <0.125 | 0.25 | 0.25 | <0.125 |
| 6 | >32 | 4 | >32 | 1 | 0.5 | 1 | >32 | 0.5 | 0.25 | 0.25 | 0.25 |
| 7 | 2 | 4 | >32 | 0.25 | <0.125 | <0.125 | 32 | <0.125 | 0.5 | 0.25 | 0.25 |
| 8 | 4 | 8 | >32 | 2 | 1 | 2 | 32 | 1 | 0.25 | 0.25 | 0.5 |
| 9 | 4 | 8 | 32 | 0.25 | 0.5 | 1 | 16 | 1 | 1 | 0.5 | 1 |
| 10 | 2 | 4 | 4 | 1 | 1 | 0.5 | 2 | 0.5 | 1 | 1 | 0.5 |
| 11 | 4 | 4 | 32 | 2 | 1 | 0.5 | 32 | 0.25 | 0.5 | 0.5 | 0.5 |
| 12 | >32 | 8 | >32 | 4 | 4 | 4 | >32 | 2 | 1 | 0.25 | 0.5 |
| 13 | 4 | 4 | >32 | 1 | 0.5 | 1 | 32 | 0.25 | 0.5 | 0.25 | 0.25 |
| 14 | >32 | 8 | >32 | 16 | 4 | 8 | >32 | 1 | 4 | 0.25 | 0.5 |
| 15 | 16 | 16 | >32 | 2 | 1 | 0.5 | 8 | 1 | 1 | 1 | 2 |
| 16 | 4 | 4 | >32 | 2 | 2 | 0.5 | >32 | 0.25 | 0.25 | 0.5 | 0.25 |
| 17 | 2 | 4 | 16 | <0.125 | 0.25 | <0.125 | <0.125 | 0.25 | 0.5 | 0.25 | 0.25 |
| 18 | 8 | 8 | 2 | 0.5 | 0.5 | 0.5 | 8 | 0.25 | 0.5 | 1 | 0.5 |
| 19 | 32 | 16 | >32 | 2 | 4 | 0.5 | 32 | 0.5 | 0.5 | 1 | 0.5 |
| 20 | 0.5 | 0.5 | >32 | 4 | 2 | 4 | 0.25 | 0.25 | <0.125 | <0.125 | 0.5 |
| 21 | 0.5 | 0.5 | >32 | 1 | 0.5 | 2 | >32 | 0.25 | 0.125 | 0.125 | 0.125 |
| 22 | 1 | 1 | 16 | 1 | 0.5 | 1 | >32 | 0.5 | 0.25 | <0.125 | <0.125 |
| 23 | 1 | 1 | 4 | 0.5 | 0.25 | 0.5 | 2 | <0.125 | 0.25 | <0.125 | <0.125 |
| 24 | 0.5 | 0.5 | 16 | 1 | 1 | 1 | >32 | <0.125 | 0.25 | <0.125 | <0.125 |
| 25 | >32 | 0.5 | >32 | 8 | 4 | 4 | >32 | 0.25 | 0.5 | <0.125 | 0.25 |
| 26 | 0.5 | 2 | >32 | 16 | 16 | 8 | >32 | 2 | 1 | 0.5 | 0.5 |
| 27 | 1 | 1 | 16 | 1 | 1 | 1 | 1 | 0.5 | 0.25 | <0.125 | <0.125 |
| 28 | 2 | 4 | 4 | 2 | 1 | 2 | 0.5 | 2 | 0.5 | 0.5 | 0.5 |
| 29 | 1 | 4 | 32 | 8 | 4 | 2 | 1 | 1 | 0.5 | 0.5 | 1 |
| 30 | 1 | 1 | >32 | 32 | 32 | 32 | >32 | 1 | 4 | 2 | 2 |
| 31 | 0.5 | 0.5 | 16 | 4 | 2 | 4 | >32 | <0.125 | 0.5 | <0.125 | 0.25 |
| 32 | >32 | 1 | >32 | >32 | >32 | >32 | >32 | 1 | >32 | 1 | 1 |
| 33 | 0.5 | 0.5 | 8 | 0.5 | 0.25 | 0.25 | <0.125 | <0.125 | 1 | <0.125 | <0.125 |
| 34 | 1 | 0.5 | >32 | 2 | 2 | 2 | >32 | <0.125 | 4 | <0.125 | <0.125 |
| 35 | 0.5 | 0.5 | 16 | 0.5 | 0.25 | 0.5 | 1 | <0.125 | <0.125 | <0.125 | 0.25 |
| 36 | 1 | 1 | 4 | 0.25 | 0.5 | 0.5 | 0.5 | 0.25 | 0.25 | 0.25 | <0.125 |
| 37 | 1 | 0.5 | 2 | 0.25 | 0.25 | 0.5 | 0.5 | 0.25 | 0.5 | 0.5 | 4 |
| 38 | 1 | 2 | 2 | 0.5 | 1 | 0.5 | 8 | 0.25 | 1 | 0.5 | 0.5 |
| 39 | 1 | 2 | 2 | 0.5 | 1 | 2 | 2 | 0.5 | 0.5 | 0.5 | 0.5 |
| 40 | 0.5 | 2 | 4 | 0.5 | 0.5 | 0.5 | 8 | 0.25 | 0.25 | 0.25 | 0.25 |
| 41 | 1 | 4 | 2 | 1 | 0.5 | 1 | >32 | 0.5 | 0.5 | 1 | 0.5 |
| 42 | 0.5 | 2 | >32 | 4 | 2 | 4 | 4 | <0.125 | 0.25 | <0.125 | <0.125 |
| 43 | 0.5 | 1 | 16 | 0.5 | 1 | 0.5 | 0.5 | <0.125 | 0.5 | 0.25 | <0.125 |
| 44 | 0.5 | 1 | 16 | 1 | 1 | 1 | 32 | <0.125 | <0.125 | 0.25 | <0.125 |
| 45 | 0.5 | 1 | 16 | 8 | 2 | 4 | >32 | 0.5 | 0.5 | 0.5 | 0.25 |
| 46 | 0.5 | 0.5 | 2 | 0.25 | 0.25 | 0.25 | <0.125 | <0.125 | <0.125 | <0.125 | 0.25 |
| 47 | 1 | 1 | 8 | 8 | 1 | 2 | 16 | <0.125 | 0.25 | 0.5 | 0.5 |
| 48 | 0.5 | 2 | 4 | 1 | 1 | 1 | 32 | 0.25 | <0.125 | 0.25 | <0.125 |
| 49 | 0.5 | 0.25 | 16 | 1 | 0.5 | 0.5 | >32 | <0.125 | 0.25 | 0.5 | 0.5 |
| 50 | 1 | 0.5 | >32 | 0.5 | 1 | 0.5 | 32 | <0.125 | <0.125 | <0.125 | <0.125 |
| 51 | 1 | 0.5 | >32 | 4 | 8 | 4 | >32 | 0.25 | 1 | 0.25 | 0.25 |
| 52 | 0.5 | 1 | >32 | 1 | 0.5 | 0.5 | 32 | <0.125 | 0.5 | 0.25 | 0.25 |
| 53 | 8 | 2 | >32 | 16 | 8 | 8 | >32 | 0.25 | 8 | 0.5 | 2 |
| 54 | 4 | 2 | 16 | 0.5 | 0.25 | 0.5 | 0.5 | 0.25 | 0.25 | <0.125 | <0.125 |
| 55 | >32 | >32 | >32 | >32 | >32 | >32 | >32 | 2 | >32 | 1 | 4 |
| 56 | 0.5 | 2 | 4 | 2 | 1 | 1 | 16 | 0.25 | 0.25 | <0.125 | <0.125 |
| 57 | 0.5 | 0.5 | 4 | 2 | 0.5 | 1 | 0.5 | <0.125 | 1 | 1 | 1 |
| 58 | 0.5 | 2 | 2 | 0.25 | 1 | 0.5 | 0.25 | 0.25 | 0.5 | 0.25 | 0.25 |

TABLE 7-continued

| Minimum inhibitory concentrations (mg/L) for compounds 1-153 | | | | | | | | | | | |
|---|---|---|---|---|---|---|---|---|---|---|---|
| | Pa | | | Ab | | | Kp | | Ec | | |
| Compound | ATCC 27853 | FADDI-PA022 | FADDI-PA025 | ATCC 19606 | FADDI-AB034 | A ATCC 17978 | ATCC 13883 | FADDI-KP032 | FADDI-EC006 | FADDI-EC001 | FADDI-EC003 |
| 59 | 1 | 2 | 2 | 2 | 0.5 | 1 | 0.25 | <0.125 | 0.5 | 1 | 1 |
| 60 | 0.5 | 0.5 | 8 | 1 | 0.5 | 0.5 | 1 | <0.125 | 0.5 | <0.125 | <0.125 |
| 61 | 0.5 | 0.5 | >32 | 4 | 1 | 2 | >32 | 0.25 | 0.25 | 0.25 | 0.25 |
| 62 | 0.5 | 1 | 1 | 2 | 1 | 1 | >32 | 0.25 | 0.25 | <0.125 | <0.125 |
| 63 | 0.5 | 2 | >32 | 2 | 1 | 1 | 32 | 0.25 | 0.5 | 0.5 | <0.125 |
| 64 | 1 | 2 | 8 | 0.5 | 1 | 0.5 | 16 | <0.125 | 0.25 | 0.5 | <0.125 |
| 65 | 1 | 2 | 16 | 0.5 | 1 | 0.25 | 4 | <0.125 | 0.25 | 0.5 | <0.125 |
| 66 | 1 | 2 | 4 | 0.25 | 0.5 | 0.25 | 4 | <0.125 | 0.25 | 0.5 | <0.125 |
| 67 | 0.5 | 0.5 | 2 | 4 | 4 | 2 | >32 | 1 | 0.5 | <0.125 | 0.25 |
| 68 | 0.5 | 0.5 | 2 | 2 | 1 | 1 | 32 | 0.25 | <0.125 | 0.25 | <0.125 |
| 69 | 0.5 | 0.5 | 8 | 0.5 | 0.25 | 0.5 | 16 | <0.125 | <0.125 | 0.25 | <0.125 |
| 70 | 1 | 1 | 2 | 0.5 | 1 | 0.5 | 16 | 0.25 | 0.5 | 0.5 | 0.25 |
| 71 | 0.5 | 4 | 1 | 0.5 | 0.25 | 0.25 | 16 | 0.5 | 1 | 1 | 0.25 |
| 72 | 0.5 | 0.5 | 4 | 8 | 4 | 4 | 16 | 1 | 0.5 | 0.5 | 0.25 |
| 73 | 0.5 | 1 | 4 | 8 | 4 | 4 | 1 | 1 | 1 | 0.25 | 0.25 |
| 74 | 0.5 | 0.5 | 2 | 0.5 | 1 | 0.5 | .25 | 0.25 | 2 | <0.125 | 0.25 |
| 75 | 0.5 | 1 | 2 | 1 | 1 | 1 | 2 | 0.5 | 0.5 | 0.25 | 0.25 |
| 76 | 0.5 | 1 | 4 | 2 | 1 | 1 | 0.5 | 0.5 | 0.5 | 0.25 | 0.25 |
| 77 | 0.25 | 0.5 | 4 | 4 | 1 | 0.5 | 0.25 | <0.125 | 0.25 | 0.5 | <0.125 |
| 78 | 1 | 0.5 | 4 | 4 | 2 | 2 | 1 | 0.5 | 0.5 | 0.25 | 0.25 |
| 79 | 0.5 | 1 | 1 | 1 | 1 | 0.5 | 8 | <0.125 | 2 | 0.25 | <0.125 |
| 80 | 0.5 | 1 | 2 | 4 | 2 | 1 | 16 | 0.5 | 4 | <0.125 | 0.25 |
| 81 | 2 | 4 | 1 | 1 | 0.25 | 0.5 | 4 | <0.125 | 0.25 | 0.25 | <0.125 |
| 82 | 0.5 | 0.5 | 1 | 0.5 | 0.25 | 0.5 | 1 | <0.125 | <0.125 | <0.125 | <0.125 |
| 83 | 1 | 1 | 2 | 2 | 0.5 | 1 | >32 | 0.25 | 0.25 | 0.25 | 0.25 |
| 84 | 0.5 | 2 | 2 | 8 | 2 | 2 | >32 | 0.5 | 0.5 | <0.125 | 0.25 |
| 85 | 0.5 | 2 | 2 | 4 | 2 | 2 | 32 | 1 | 1 | 0.5 | 1 |
| 86 | 0.5 | 1 | 2 | 4 | 1 | 2 | 4 | 1 | 1 | 1 | 1 |
| 87 | 0.5 | 1 | 2 | 2 | 2 | 1 | 1 | 1 | 2 | 2 | 1 |
| 88 | 0.5 | 1 | 2 | 2 | 0.5 | 0.5 | 8 | 0.5 | 0.5 | 1 | 0.25 |
| 89 | 0.5 | 1 | 4 | 4 | 1 | 1 | <0.125 | 0.25 | 2 | <0.125 | <0.125 |
| 90 | 0.5 | 2 | 2 | 2 | 8 | 1 | <0.125 | 0.5 | 0.25 | 0.5 | 8 |
| 91 | 0.5 | 2 | 4 | 4 | 2 | 1 | 2 | 0.5 | 0.5 | <0.125 | <0.125 |
| 92 | 0.5 | 0.5 | 4 | 4 | 4 | 0.5 | 0.25 | 0.25 | 2 | <0.125 | 0.25 |
| 93 | 2 | 4 | 2 | 1 | 0.5 | 0.5 | 2 | 0.5 | 4 | 0.25 | 1 |
| 94 | 0.5 | 0.5 | 2 | 1 | 0.25 | 0.5 | 1 | 0.25 | 0.5 | 0.25 | 0.25 |
| 95 | 2 | 4 | 2 | 0.25 | 0.25 | 0.25 | 16 | <0.125 | 1 | <0.125 | 0.25 |
| 96 | 0.25 | 0.25 | 0.5 | 0.5 | 0.25 | 0.25 | <0.125 | <0.125 | 0.5 | 1 | 1 |
| 97 | 0.5 | 0.5 | 1 | 0.5 | 0.25 | <0.125 | <0.125 | <0.125 | 0.5 | 0.5 | 0.25 |
| 98 | 0.5 | 0.5 | 2 | 2 | 2 | 2 | >32 | 1 | 2 | 1 | 0.25 |
| 99 | 1 | 0.5 | 2 | 1 | 0.25 | 0.25 | >32 | 0.5 | 0.5 | 0.25 | 0.25 |
| 100 | 0.5 | 0.5 | 2 | 2 | 1 | 1 | >32 | 0.5 | 0.5 | 0.25 | 0.5 |
| 101 | 0.5 | 2 | 2 | 0.5 | 1 | 0.5 | 8 | 0.25 | 0.25 | <0.125 | <0.125 |
| 102 | 0.5 | 0.5 | 2 | 2 | 1 | 1 | >32 | 0.5 | 4 | 1 | 0.5 |
| 103 | 0.5 | 0.5 | 2 | 0.5 | 0.5 | 0.5 | 16 | <0.125 | 0.5 | <0.125 | <0.125 |
| 104 | 0.5 | 0.5 | 2 | 1 | 0.25 | 0.5 | 8 | 1 | 0.5 | 0.5 | 0.25 |
| 105 | 0.5 | 1 | 2 | 0.5 | 0.25 | 0.5 | >32 | 0.25 | 1 | 1 | 0.5 |
| 106 | 0.5 | 0.5 | 2 | 0.5 | 0.25 | 0.5 | 0.5 | 0.25 | 0.25 | 0.25 | 0.5 |
| 107 | 0.5 | 0.5 | 2 | 2 | 0.25 | 0.5 | 8 | 0.25 | 0.25 | 0.25 | 0.25 |
| 108 | 0.5 | 0.5 | 2 | 0.5 | 0.5 | 0.5 | 0.5 | 0.25 | 0.5 | 1 | 0.5 |
| 109 | 0.5 | 0.5 | 2 | 0.25 | 1 | 1 | 4 | 0.25 | 0.25 | 1 | <0.125 |
| 110 | 0.5 | 0.5 | 1 | 2 | 0.5 | 0.5 | 16 | 0.25 | 0.5 | 1 | 1 |
| 111 | 0.5 | 1 | 1 | 0.5 | 0.25 | 0.5 | 16 | 0.25 | 0.25 | 0.5 | 0.25 |
| 112 | 0.5 | 0.5 | 1 | 0.25 | 0.25 | <0.125 | 0.25 | 0.5 | 0.5 | 0.5 | 0.25 |
| 113 | 1 | 0.5 | 2 | 0.5 | 0.25 | 0.25 | <0.125 | 0.25 | 1 | 1 | 0.25 |
| 114 | 0.5 | 1 | 1 | 2 | 0.5 | 0.5 | 32 | 0.25 | 0.25 | 0.25 | 0.25 |
| 115 | 1 | 0.5 | 1 | 0.5 | 0.5 | 0.5 | 0.25 | <0.125 | 0.25 | 0.25 | 0.25 |
| 116 | 0.5 | 0.5 | 1 | 0.5 | 0.25 | 0.5 | 0.25 | 0.5 | 0.25 | 0.25 | 0.25 |
| 117 | 0.25 | 2 | 2 | 1 | 1 | 0.25 | 4 | 0.25 | 1 | 0.25 | 0.25 |
| 118 | 0.5 | 2 | 2 | 2 | 1 | >32 | 32 | 0.25 | 0.5 | 1 | 0.25 |
| 119 | 0.5 | 0.5 | 2 | 1 | 0.25 | 0.5 | 1 | <0.125 | 0.25 | <0.125 | <0.125 |
| 120 | 1 | 1 | 2 | 1 | 0.5 | 0.5 | 1 | 0.5 | 0.25 | 0.25 | 0.25 |
| 121 | 0.5 | 1 | 2 | 0.5 | 0.5 | 0.5 | 0.5 | 0.25 | 0.25 | 0.25 | 0.25 |
| 122 | 2 | 2 | 2 | 0.5 | 0.5 | 0.25 | 0.5 | 0.5 | 0.25 | 0.5 | 0.5 |
| 123 | 0.5 | 0.5 | 2 | 1 | 0.5 | 1 | 32 | 0.5 | 1 | 0.5 | 0.5 |
| 124 | 0.25 | 0.5 | 2 | 1 | 0.25 | 1 | 1 | 0.25 | 0.5 | 0.5 | <0.125 |
| 125 | 0.25 | 0.5 | 2 | 1 | 0.5 | 1 | 0.5 | 0.25 | 1 | 0.5 | 0.5 |
| 126 | 0.25 | 1 | 2 | 1 | 1 | 1 | 0.25 | 0.5 | 0.5 | 0.5 | 0.5 |
| 127 | 0.5 | 0.5 | 16 | 4 | 0.5 | 1 | 16 | 0.5 | 0.5 | <0.125 | 0.25 |
| 128 | 0.5 | 1 | 4 | 0.25 | 0.25 | 0.25 | <0.125 | 0.25 | 0.5 | <0.125 | 0.25 |
| 129 | 0.5 | 1 | 2 | 0.5 | 0.25 | 0.25 | 2 | <0.125 | 0.5 | 0.5 | <0.125 |
| 130 | 0.5 | 2 | 2 | 0.25 | 0.25 | 0.25 | 16 | 0.5 | 1 | 0.25 | 0.25 |
| 131 | 0.5 | 2 | 4 | 0.25 | 0.25 | 0.25 | 32 | <0.125 | <0.125 | <0.125 | <0.125 |

TABLE 7-continued

| Minimum inhibitory concentrations (mg/L) for compounds 1-153 | | | | | | | | | | | |
|---|---|---|---|---|---|---|---|---|---|---|---|
| | Pa | | | Ab | | | Kp | | Ec | | |
| Compound | ATCC 27853 | FADDI-PA022 | FADDI-PA025 | ATCC 19606 | FADDI-AB034 | A ATCC 17978 | ATCC 13883 | FADDI-KP032 | FADDI-EC006 | FADDI-EC001 | FADDI-EC003 |
| 132 | 0.5 | 1 | 4 | 0.5 | 0.25 | 0.5 | 32 | 0.25 | <0.125 | 0.25 | <0.125 |
| 133 | 0.5 | 0.5 | 2 | 2 | 0.25 | 0.5 | >32 | 0.25 | 0.25 | 0.5 | 0.25 |
| 134 | 0.5 | 1 | 1 | 2 | 0.5 | 2 | >32 | <0.125 | <0.125 | 0.25 | <0.125 |
| 135 | 0.5 | 1 | 2 | 4 | 1 | 1 | 4 | 0.25 | <0.125 | <0.125 | <0.125 |
| 136 | 0.5 | 2 | 1 | 0.5 | 0.25 | 0.5 | 4 | <0.125 | 0.25 | <0.125 | <0.125 |
| 137 | 0.5 | 1 | 4 | 0.5 | 0.25 | 0.25 | 1 | <0.125 | <0.125 | <0.125 | <0.125 |
| 138 | 1 | 2 | 1 | 1 | 0.5 | 0.5 | 2 | 0.5 | 0.5 | 0.5 | 1 |
| 139 | 1 | 2 | 1 | 0.5 | 0.25 | 0.25 | <0.125 | <0.125 | 1 | 0.5 | 0.25 |
| 140 | 1 | 1 | 4 | 2 | 1 | 0.5 | 0.25 | 0.25 | 1 | 0.5 | 0.25 |
| 141 | 1 | 1 | 2 | 16 | 4 | 4 | >32 | 0.5 | 4 | 2 | 1 |
| 142 | 1 | 1 | 1 | 1 | 0.25 | 0.5 | 0.5 | 0.25 | 0.5 | 0.25 | 1 |
| 143 | 0.5 | 0.5 | 16 | 1 | 0.5 | 1 | 0.25 | 0.25 | 0.5 | 1 | 0.5 |
| 144 | 1 | 2 | 1 | 1 | 0.5 | 1 | 0.5 | 1 | 1 | 2 | 1 |
| 145 | 0.5 | 0.5 | 1 | 1 | 0.5 | 0.5 | 1 | <0.125 | <0.125 | 0.5 | <0.125 |
| 146 | 0.5 | 0.5 | >32 | 4 | 2 | 1 | 1 | 0.5 | 0.5 | 0.5 | 0.25 |
| 147 | 1 | 1 | >32 | 4 | 2 | 4 | 4 | 0.5 | 1 | <0.125 | 1 |
| 148 | 1 | 1 | 16 | 2 | 1 | 0.5 | 1 | 0.5 | 1 | 2 | 4 |
| 149 | >32 | >32 | >32 | >32 | >32 | >32 | >32 | 16 | >32 | >32 | >32 |
| 1/20[#] | 0.5 | 0.5 | >32 | 0.5 | 0.5 | 0.5 | 0.25 | <0.125 | 0.25 | <0.125 | 1 |
| 150 | 4 | 4 | >32 | 0.25 | 0.25 | 0.25 | 8 | 0.5 | 0.5 | 0.5 | 0.5 |
| 151 | 4 | 4 | >32 | 0.5 | 0.5 | 0.25 | 16 | 0.5 | 0.25 | 0.25 | 0.25 |
| 152 | 1 | 1 | 32 | 1 | 1 | 1 | >32 | 0.5 | 0.25 | 0.5 | 0.5 |
| 153 | 0.5 | 4 | >32 | 2 | 1 | 2 | >32 | 0.25 | 0.5 | 0.25 | 0.25 |

Pa = Pseudomonas aeruginosa,
Ab = Acinetobacter baumannii,
Kp = Klebsiella pneumonia,
Ec = Enterobacter cloacae,
[#]1:1 ratio of compounds 1 and 20.

As is evident from the above data, the exemplified compounds have comparable or improved antibacterial efficacy against one or more of the above Gram-negative bacterial isolates.

Example 3. In Vivo Efficacy in Mouse Blood Infection Model

P. aeruginosa ATCC 27853, A. baumannii ATCC 19606 and K. pneumoniae FADDI-KP032 were subcultured on nutrient agar plates. One colony of each bacterial strain was dispersed in 10-mL CAMHB and incubated overnight. On day 2, an aliquot (0.2 mL) of each overnight culture suspension was dispersed in 20-mL CAMHB and incubated for 1.5-2.5 h for production of early log-phase growth bacterial culture. The bacteria in the early log-phase growth suspension were concentrated by centrifugation (3,220 g for 10 min) and re-suspended in sterile 0.9% saline for inoculation into mice. The bacterial cell concentration (colony forming unit [CFU]/mL) in saline was estimated by determining the optical density (OD) of the suspension at 600 nm, and confirmed by plating the suspension on nutrient agar plates. Swiss mice (22 to 28 g) were rendered neutropenic by injecting two doses of cyclophosphamide intraperitoneally, −4 day (150 mg/kg) and −1 day (100 mg/kg) prior to inoculation. Bloodstream infection was established by injecting intravenously 50 μL of early log-phase bacterial suspension ($10^8$-$10^9$ CFU/mL). The exact injection volume for each bacterial suspension was calculated based upon the OD value of the bacterial suspension and the desired inoculum for each isolate.

Solutions for administration of colistin, polymyxin B or the compounds were prepared at a concentration of 1 mg (free base) per mL in sterile 0.9% saline. At 2 h after inoculation, a mouse in the treatment groups was injected intravenously with one of the above solutions at 4 μL/g body weight (BW) (i.e. free base 4 mg/kg BW), while the same volume of saline was injected into the control mice. At 0 h or at 4 h after the administration of antibacterial drug or saline (control), animals were euthanised by inhalation of overdose isoflurane. The skin on the chest and fore-paws of each animal was thoroughly cleansed with 70% ethanol and Betadine®. The blood was collected via cardiac puncture using a 1-mL syringe rinsed with heparin (5,000 IU/mL), diluted serially in sterile 0.9% saline and plated on nutrient agar plates using a spiral plater.

The agar plates were incubated at 37° C. overnight. The bacterial colonies on the plate were counted and CFU/mL of the blood was calculated. The $\log_{10}$ CFU/mL of blood in each mouse was calculated. The in vivo activity of the compounds against the bacteria was calculated as the difference of the $\log_{10}$ CFU/mL values between the treated mice and the control mice at 4 h (Δ log=$\log_{10}$ (treated)CFU/mL−$\log_{10}$ (control)CFU/mL). The results obtained are documented in Table 8.

Any compound showing a decrease in bacterial loading (Δ log) of ≥2 at 4 h is considered to have good in vivo efficacy in this initial screening model. As is evident from the Table below, the compounds of the invention have comparable or improved in vivo antibacterial efficacy compared to the clinically available polymyxin B (Reduction of bacterial loading for the polymyxin B control used in the corresponding experiment is shown in brackets next to the reduction in bacterial loading for the compound).

TABLE 8

In vivo efficacy in mouse blood infection model

| | P. aeruginosa ATCC 27853 | | A. baumannii ATCC 19606 | | K. pneumoniae FADDI-KP032 | |
|---|---|---|---|---|---|---|
| Compound | MIC (mg/L) | Δ log (Treated-Control at 4 h)^ | MIC (mg/L) | Δ log (Treated-Control at 4 h)^ | MIC (mg/L) | Δ log (Treated-Control at 4 h)^^ |
| 1 | 4 | 0.40 (−2.44) | <0.125 | −2.13 (−2.32) | 0.5 | −3.49 (−3.66) |
| 2 | 8 | — | 0.5 | −2.70 (−2.58) | 0.5 | −3.44 (−3.15) |
| 3 | 4 | — | 0.25 | −2.02 (−2.58) | <0.125 | −3.45 (−3.15) |
| 4 | 4 | — | 8 | — | 1 | −1.84 (−3.15) |
| 5 | 2 | −0.54 (−2.21) | <0.125 | −2.60 (−2.58) | <0.125 | −3.74 (−3.15) |
| 6 | >32 | — | 1 | −2.35 (−2.58) | 0.5 | — |
| 7 | | −0.61 (−2.21) | 0.25 | −2.87 (−2.58) | <0.125 | −3.39 (−3.15) |
| 8 | 4 | −0.05 (−3.45) | 2 | — | 1 | — |
| 18 | 8 | — | 0.5 | −1.57 (−1.79) | 0.25 | — |
| 19 | 32 | — | 2 | −1.58 (−1.79) | 0.5 | — |
| 20 | 0.5 | −2.13 (−2.21) | 4 | −1.86 (−1.90) | 0.25 | −3.50 (−3.15) |
| 21 | 0.5 | −2.26 (−2.21) | 1 | −2.43 (−2.58) | 0.25 | — |
| 22 | 1 | −3.10 (−2.21) | 1 | −1.50 (−2.58) | 0.5 | −3.11 (−3.15) |
| 23 | 1 | −2.48 (−2.21) | 0.5 | −2.82 (−2.58) | <0.125 | −3.88 (−3.15) |
| 24 | 0.5 | −2.31 (−2.21) | 1 | −2.16 (−2.58) | <0.125 | −3.21 (−3.15) |
| 25 | >32 | | 8 | 0.27 (−2.58) | 0.25 | −2.65 (−3.15) |
| 26 | 0.5 | −0.04 (−3.45) | 16 | — | 2 | — |
| 27 | 1 | −3.67 (−3.45) | 1 | — | 0.5 | — |
| 29 | 1 | −2.80 (−3.45) | 8 | — | 1 | — |
| 30 | 1 | −0.39 (−3.45) | 32 | — | 1 | — |
| 33 | 0.5 | −1.55 (−2.83) | 0.5 | −1.40 (−2.08) | <0.125 | −2.80 (−3.00) |
| 35 | 0.5 | −3.36 (−3.74) | 0.5 | −1.60 (−1.57) | <0.125 | −3.12 (−3.00) |
| 46 | 0.5 | −2.53 (−3.91) | 0.25 | −1.56 (−1.57) | <0.125 | −2.93 (−2.64) |
| 58 | 0.5 | −3.00 (−2.83) | 0.25 | −2.15 (−1.86) | 0.25 | −3.21 (−3.13) |
| 59 | 1 | −2.82 (−2.87) | 2 | — | <0.125 | — |
| 61 | 0.5 | −4.75 (−3.91) | 4 | — | 0.25 | — |
| 62 | 0.5 | −2.69 (3.35) | 2 | — | 0.25 | — |
| 70 | 1 | −3.11 (−3.91) | 0.5 | — | 0.25 | — |
| 71 | 0.5 | −4.04 (−3.91) | 0.5 | −1.82 (−1.86) | 0.5 | −2.98 (−3.13) |
| 74 | 0.5 | −3.10 (−3.83) | 0.5 | −2.34 (−1.86) | 0.25 | −2.94 (−3.13) |
| 77 | 0.25 | −2.28 (−3.35) | 4 | — | <0.125 | — |
| 79 | 0.5 | −2.28 (−3.35) | 1 | — | <0.125 | — |
| 82 | 0.5 | −3.44 (−3.35) | 0.5 | −1.44 (−1.79) | <0.125 | −3.33 (−3.13) |
| 83 | 1 | −3.63 (−3.35) | 2 | — | 0.25 | — |
| 88 | 0.5 | −3.33 (−3.83) | 2 | −2.46 (−1.86) | 0.5 | — |
| 94 | 0.5 | −3.23 (−3.83) | 1 | −1.26 (1.86) | 0.25 | — |
| 96 | 0.25 | −3.45 (−3.83) | 0.5 | −2.42 (−1.86) | <0.125 | −2.75 (−3.13) |
| 99 | 1 | −3.21 (−3.83) | 1 | — | 0.5 | — |
| 100 | 0.5 | −3.83 (−3.83) | 2 | — | 0.5 | — |
| 104 | 0.5 | −3.08 (−2.99) | 1 | −1.35 (−1.86) | 1 | −3.23 (−3.13) |
| 105 | 0.5 | −2.54 (−2.99) | 0.5 | −1.31 (−1.86) | 0.25 | — |
| 106 | 0.5 | −2.33 (−2.99) | 0.5 | — | 0.25 | −2.77 (−3.13) |
| 107 | 0.5 | −2.98 (−2.99) | 2 | — | 0.25 | — |
| 108 | 0.5 | −2.32 (−2.99) | 0.5 | −1.82 (−1.79) | 0.25 | −2.84 (−3.13) |
| 109 | 0.5 | −2.68 (−2.99) | 0.25 | −1.54 (−1.86) | 0.25 | −3.47 (−3.13) |
| 110 | 0.5 | −3.30 (−2.99) | 2 | −1.57 (−1.79) | 0.25 | −2.50 (−3.13) |
| 111 | 1 | −3.65 (−2.99) | 0.5 | −1.66 (−1.79) | 0.25 | — |
| 112 | 0.5 | −3.15 (−2.99) | 0.25 | — | 0.5 | — |
| 113 | 0.5 | −2.61 (−2.87) | 0.5 | −1.60 (−1.79) | 0.25 | — |
| 114 | 0.5 | −2.57 (−2.87) | 2 | — | 0.25 | — |
| 115 | 1 | −2.71 (−2.87) | 0.5 | — | 0.125 | — |
| 116 | 0.5 | −2.81 (−2.87) | 0.5 | −1.51 (−.179) | 0.5 | — |
| 117 | 0.25 | −2.99 (−3.14) | 1 | — | 0.25 | — |
| 118 | 0.5 | −3.53 (−3.14) | 2 | — | 0.25 | — |
| 119 | 0.5 | −3.40 (−3.14) | 1 | — | <0.125 | — |
| 120 | 1 | −3.20 (−3.14) | 1 | — | 0.5 | — |
| 121 | 0.5 | −2.81 (−3.14) | 0.5 | — | 0.25 | — |
| 122 | 2 | −3.70 (−3.14) | 0.5 | −1.58 (−1.79) | 0.5 | — |
| 123 | 0.5 | −2.96 (−3.14) | 1 | −1.53 (−1.79) | 0.5 | — |
| 124 | 0.25 | −3.36 (−3.14) | 1 | — | 0.25 | — |
| 125 | 0.25 | −3.66 (−3.14) | 1 | — | 0.25 | — |
| 126 | 0.25 | −3.97 (−3.14) | 1 | — | 0.5 | −2.68 (−3.13) |
| 127 | 0.5 | −3.51 (−3.59) | 4 | — | 0.5 | — |
| 129 | 0.5 | −3.45 (−3.59) | 0.5 | −1.42 (−1.26) | <0.125 | −3.64 (−3.24) |
| 130 | 0.5 | −3.66 (−3.59) | 0.25 | — | 0.5 | — |
| 131 | 0.5 | −3.80 (−3.59) | 0.25 | −1.75 (−1.26) | <0.125 | −3.44 (−3.24) |
| 132 | 0.5 | −4.39 (−3.59) | 0.5 | −1.58 (−1.26) | 0.25 | −3.16 (−3.24) |
| 133 | 0.5 | −3.23 (−3.59) | 2 | — | 0.25 | — |
| 138 | 1 | −2.98 (−3.23) | 1 | — | 0.5 | — |
| 139 | 1 | −3.19 (−3.23) | 0.5 | — | <0.125 | — |
| 140 | 1 | −3.27 (−3.23) | 2 | — | 0.25 | — |
| 142 | 1 | −3.89 (−3.23) | 1 | — | 0.25 | — |

TABLE 8-continued

| In vivo efficacy in mouse blood infection model | | | | | | |
|---|---|---|---|---|---|---|
| | P. aeruginosa ATCC 27853 | | A. baumannii ATCC 19606 | | K. pneumoniae FADDI-KP032 | |
| Compound | MIC (mg/L) | Δ log (Treated-Control at 4 h)^ | MIC (mg/L) | Δ log (Treated-Control at 4 h)^ | MIC (mg/L) | Δ log (Treated-Control at 4 h)^^ |
| 143 | 0.5 | −3.47 (−3.23) | 1 | — | 0.25 | — |
| 144 | 1 | −2.98 (−3.23) | 1 | — | 1 | — |
| 146 | 0.5 | −3.63 (−3.23) | 4 | — | 0.5 | — |
| 1/20* | | −1.52 (−2.83) | | −1.86 (−2.08) | | −2.82 (−3.00) |
| 150 | 4 | −0.29 (−3.18) | 0.25 | −1.46 (−1.17) | 0.5 | −3.77 (−2.99) |
| 151 | 4 | −0.40 (−2.20) | 0.5 | −1.59 (−2.53) | 0.5 | −4.71 (−4.06) |
| 152 | 1 | −3.24 (−3.18) | 1 | −1.61 (−1.17) | 0.5 | −3.86 (−2.99) |
| 153 | 0.5 | −2.73 (−3.18) | 2 | −1.26 (−1.17) | 0.25 | −3.59 (−2.99) |

— Not determined

^The Δ log (Treated-Control at 4 h) for the polymyxin B control used in the corresponding experiment is shown in brackets next to the Δ log (Treated-Control at 4 h) for each compound.

*1:1 ratio of compound 1 and 20.

Example 4. Nephrotoxicity in a Mouse Model

PMB sulphate (Batch 20120204) and colistin sulphate (Batch 20120719) were supplied by Betapharma (Shanghai Co., Ltd, China). Stock solutions of compounds in saline (5 mg base/mL) were stored at 4° C. before use. The mice were subcutaneously administered with the drug/compound at 12 mg base/kg, 6 doses in one day every 2 h. At ~20 h after the last dose, mice were euthanised by inhalation of an overdose of isoflurane. Immediately after blood sampling, the right kidney from each mouse was collected immediately and placed in 10% formalin in 5-mL plastic tubes separately, and the left kidney placed in a pre-weighed in 14-mL plastic tubes, weighed again and stored at −20° C. pending for homogenization and analysis of polymyxin and colistin. The frozen kidney samples were thawed, homogenized in 2 mL of Milli-Q water and stored in a −20° C. freezer. The formalin-fixed kidneys were then sent to the Australian Phenomics Network-Histopathology and Organ Pathology (The University of Melbourne, Parkville, VIC, Australia) for histological examination. The samples were examined by a pathologist who was blind to the treatment groups.

Lesions were rated as follows: mild acute tubular damage with tubular dilation, prominent nuclei and a few pale tubular casts (Grade 1); severe acute tubular damage with necrosis of tubular epithelial cells and numerous tubular casts (Grade 2); acute cortical necrosis/infarction of tubules and glomeruli with or without papillary necrosis (Grade 3). The grades were given the following scores: grade 1=1, grade 2=4, and grade 3=10. The percentages of the kidney slices affected were scored as follows: <1%=0, 1 to <5%=1, 5 to <10%=2, 10 to <20%=3, 20 to <30%=4, 30 to <40%=5, and >40%=6. The overall kidney histology score was calculated as the product of percentage score and grade score. These scores were then expressed as a semiquantitative score on a scale of 0 to +5 for renal histological changes. These scores were assigned as follows: SQS 0=no significant change (overall score, <1); SQS+1=mild damage (overall score, 1 to <15); SQS+2=mild to moderate damage (overall score, 15 to <30); SQS+3=moderate damage (overall score, 30 to <45); SQS+4=moderate to severe damage (overall score, 45 to <60); and SQS+5=severe damage (overall score, >60) (Yousef, J., Chen, G., Hill, P., Nation, R., Li, J., 2011, Antimicrobial Agents And Chemotherapy [P], vol 55, issue 9, American Society for Microbiology, USA., pp. 4044-4049).

The results obtained are documented in Table 9. Any compound with a kidney histology score of ≤+1.0 is considered to have a low nephrotoxicity in this model.

TABLE 9

| In vivo nephrotoxicity in a mouse model | | |
|---|---|---|
| Compound* | Max Overall Kidney Histology Score | Max Kidney Histology Score |
| Polymyxin B | 60.0 | +5 |
| Colistin | 60.0 | +5 |
| 1 | 5.0 | +1 |
| 2 | 3.0 | +1 |
| 3 | 3.0 | +1 |
| 5 | 6.0 | +1 |
| 6 | 0.0 | 0 |
| 7 | 6.0 | +1 |
| 9 | 0.0 | 0 |
| 11 | 0.1 | 0 |
| 16 | 0.0 | 0 |
| 17 | 6.0 | +1 |
| 19 | 5.0 | +1 |
| 20 | 0.0 | 0 |
| 21 | 0.0 | 0 |
| 22 | 0.2 | 0 |
| 23 | 0.2 | 0 |
| 24 | 3.0 | +1 |
| 27 | 0.1 | 0 |
| 33 | 0.0 | 0 |
| 35 | 2.0 | +1 |
| 36 | 0.1 | 0 |
| 37 | 0.1 | 0 |
| 42 | 0.0 | 0 |
| 43 | 0.1 | 0 |
| 44 | 0.0 | 0 |
| 46 | 4.0 | +1 |
| 58 | 0.1 | 0 |
| 59 | 4.0 | +1 |
| 60 | 1.0 | +1 |
| 62 | 0.1 | 0 |
| 63 | 0.0 | 0 |
| 64 | 0.0 | 0 |
| 65 | 0.0 | 0 |
| 66 | 4.0 | +1 |
| 70 | 2.0 | +1 |
| 71 | 0.0 | 0 |
| 75 | 0.0 | 0 |
| 77 | 2.0 | +1 |
| 78 | 0.0 | 0 |
| 79 | 5.0 | +1 |
| 82 | 0.0 | 0 |
| 83 | 0.0 | 0 |
| 88 | 0.0 | 0 |

TABLE 9-continued

| In vivo nephrotoxicity in a mouse model | | |
|---|---|---|
| Compound* | Max Overall Kidney Histology Score | Max Kidney Histology Score |
| 89 | 0.1 | 0 |
| 90 | 0.0 | 0 |
| 91 | 0.0 | 0 |
| 92 | 0.0 | 0 |
| 93 | 0.0 | 0 |
| 94 | 0.0 | 0 |
| 95 | 0.0 | 0 |
| 96 | 2.0 | +1 |
| 100 | 0.0 | 0 |
| 103 | 0.1 | 0 |
| 104 | 0.0 | 0 |
| 105 | 2.0 | +1 |
| 106 | 0.0 | 0 |
| 107 | 0.0 | 0 |
| 108 | 6.0 | +1 |
| 109 | 0.0 | 0 |
| 110 | 0.0 | 0 |
| 111 | 6.0 | +1 |
| 113 | 6.0 | +1 |
| 116 | 0.0 | 0 |
| 120 | 6.0 | +1 |
| 121 | 4.0 | +1 |
| 123 | 0.0 | 0 |
| 124 | 3.0 | +1 |
| 125 | 0.0 | 0 |
| 126 | 0.0 | 0 |
| 128 | 3.0 | +1 |
| 129 | 4.0 | +1 |
| 132 | 0.0 | 0 |
| 133 | 0.0 | 0 |
| 134 | 0.0 | 0 |
| 135 | 0.0 | 0 |
| 1/20# | 0.0 | 0 |
| 150 | 24.0 | +2 |
| 151 | 0.1 | 0 |
| 152 | 2.0 | +1 |
| 153 | 0.0 | 0 |

#1:1 ration of compound 1 and 20.

As can be observed from the above data, colistin and polymyxin B display severe nephrotoxicity in this model. On the other hand, the compounds of the present invention displayed no significant nephrotoxicity.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The claims defining the invention are as follows:

1. A compound of formula (IIb):

(IIb)

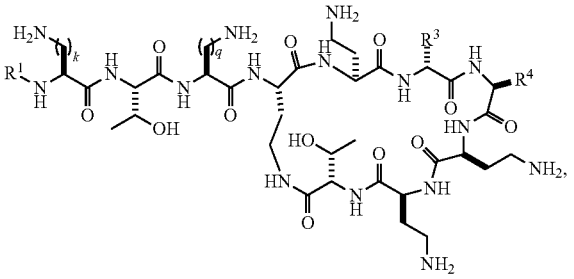

wherein:

$R^1$ is selected from [hexanoyl, hepatanoyl, octanoyl, nonanoyl, decanoyl, dodecanoyl, 7 methyloctanoyl, S-5-methylheptanoyl, R-5-methylheptanoyl, S,R-5-methylheptanoyl (racemic mixture),] 4-biphenylcarboxyl, 4-trifluoromethylbenzoyl, 4-ethylbenzoyl, 3,4-dichlorobenzoyl, 4-chlorobenzoyl, 3-chlorobenzoyl, pentafluorobenzoyl, 4-methylbenzoyl, 4-ethylphenylacetyl, phenylacetyl, 4-methylphenylacetyl, 4-trifluoromethylphenylacetyl, pentafluorophenylacetyl, 3,4-dichlorophenylacetyl, 4-chlorophenylacetyl, 3-chlorophenylacetyl, 2-chlorobenzoyl, 2-fluorobenzoyl, 2-methylbenzoyl, 2-chlorophenylacetyl, 2-fluorophenylacetyl, 2-methylphenylacetyl, 2,3-dichlorobenzoyl, 2,3-dimethylbenzoyl, 2,4-dichlorophenylacetyl, 2,4-dichlorobenzoyl, 2,4-dimethylbenzoyl, 2-chloro-4-methylbenzoyl, 2-chloro-4-trifluoromethylbenzoyl, 3-fluorobenzoyl, 3-methylbenzoyl, 3-trifuoromethylbenzoyl, 3,4-dimethylbenzoyl, 3-fluoro-4-methylbenzoyl, 4-chloro-3-methylbenzoyl, 3,4-dimethylphenylacetyl, 3-chloro-4-methylbenzoyl, 4-chloro-3-fluorobenzoyl, 3-fluoro-4-trifluoromethylbenzoyl, 3-chloro-4-fluorobenzoyl, 4-methyl-3-trifluoromethylbenzoyl, 3-methyl-4-trifluoromethylbenzoyl, 3-methyl-5-trifluoromethylbenzoyl, 3,5-dimethylbenzoyl, 3,5-dichlorobenzoyl, 3,5-bis(trifluoromethyl) benzoyl, 3-fluoro-5-trifluoromethylbenzoyl, 3-chloro-5-methylbenzoyl, 3-chloro-5-fluorobenzoyl, 2,4,6-trimethylbenzoyl, 2,4,6-trichlorobenzoyl, 2-chloro-4-fluorobenzoyl, 4-chloro-2-fluorobenzoyl, 3,4,5-trifluoromethylbenzoyl, 4-chloro-2-trifluoromethylbenzoyl, 2-fluoro-4-trifluoromethylbenzoyl, 3-biphenylcarboxyl, 4-chlorobiphenyl-4-carboxyl, 3-phenylproponyl, 4-phenylbutanoyl, 2,4-dichlorophenylsulfonyl, 4-chloro-3-trifluoromethylbenzoyl, 4-isopropylbenzoyl, 4-chloro-3-fluorobenzoyl, *and* 3-chloro-4-trifluoromethylbenzoyl;

$R^3$ represents a side chain of an amino acid selected from leucine, phenylalanine, norleucine, norvaline or t-butylglycine;

$R^4$ represents a side chain of an amino acid selected from alanine, threonine, serine, valine, t-butylglycine, 2-aminobutyric acid or 2-aminoisobutyric acid; and k and q are individually selected from 1, 2, or 3; or pharmaceutically acceptable salts thereof.

2. The compound according to claim 1, wherein $R^4$ represents the side chain of an amino acid selected from alanine, threonine, serine, 2-aminobutyric acid, or 2-aminoisobutyric acid.

3. The compound of claim 2, wherein $R^3$ represents the side chain of D-leucine; $R^4$ represents the side chain of 2-aminobutyric acid; $R^1$ is 2,4-dichlorobenzoyl; k is 2; and q is 1.

4. The compound of claim 1, selected from the group consisting of:

| Compound | $R^1$ | $R^3$ | $R^4$ | k | q |
|---|---|---|---|---|---|
| 29 | 4-BPC | D-Leu | Thr | 2 | 2 |
| 30 | PA | D-Leu | Thr | 2 | 2 |
| 56 | 4-TFMB | D-Leu | Thr | 2 | 1 |
| 57 | 3,4-DCB | D-Leu | Thr | 2 | 1 |
| 61 | 3-CPA | D-Leu | Thr | 2 | 1 |
| 62 | 2,4-DCPA | D-Leu | Thr | 2 | 1 |
| 70 | 2,4-DCPA | D-Leu | Abu | 2 | 1 |
| 71 | 3,4-DCB | D-Leu | Abu | 2 | 1 |
| 72 | 2-CB | D-Leu | Abu | 2 | 1 |
| 73 | 2-FB | D-Leu | Abu | 2 | 1 |
| 74 | 4-TFMB | D-Leu | Abu | 2 | 1 |
| 75 | 2-MB | D-Leu | Abu | 2 | 1 |
| 76 | 2-MPA | D-Leu | Abu | 2 | 1 |
| 77 | 4-CPA | D-Leu | Abu | 2 | 1 |
| 78 | PA | D-Leu | Abu | 2 | 1 |
| 79 | 3-CPA | D-Leu | Abu | 2 | 1 |
| 80 | 4-MPA | D-Leu | Abu | 2 | 1 |
| 81 | 3,4-DCPA | D-Leu | Abu | 2 | 1 |
| 82 | 2,4-DCB | D-Leu | Abu | 2 | 1 |
| 83 | 3,4-DMB | D-Leu | Abu | 2 | 1 |
| 84 | 2-CPA | D-Leu | Abu | 2 | 1 |
| 85 | 2-FPA | D-Leu | Abu | 2 | 1 |
| 86 | 3-FB | D-Leu | Abu | 2 | 1 |
| 87 | 3-MB | D-Leu | Abu | 2 | 1 |
| 88 | 3-CB | D-Leu | Abu | 2 | 1 |
| 89 | 2,4-DMB | D-Leu | Abu | 2 | 1 |
| 90 | 2,3-DCB | D-Leu | Abu | 2 | 1 |
| 91 | 2,3-DMB | D-Leu | Abu | 2 | 1 |
| 92 | 2,4,6-TMB | D-Leu | Abu | 2 | 1 |
| 93 | 3,5-DMB | D-Leu | Abu | 2 | 1 |
| 94 | 4-CB | D-Leu | Abu | 2 | 1 |
| 95 | 2,4,6-TCB | D-Leu | Abu | 2 | 1 |
| 96 | 3,5-DCB | D-Leu | Abu | 2 | 1 |
| 97 | 3,5-BTFMB | D-Leu | Abu | 2 | 1 |
| 98 | 4-MB | D-Leu | Abu | 2 | 1 |
| 99 | 4-IPB | D-Leu | Abu | 2 | 1 |
| 100 | 4-EB | D-Leu | Abu | 2 | 1 |
| 101 | 2-C-4-MB | D-Leu | Abu | 2 | 1 |
| 102 | 3-F-4-MB | D-Leu | Abu | 2 | 1 |
| 103 | 3,4-DMPA | D-Leu | Abu | 2 | 1 |
| 104 | 4-C-3-MB | D-Leu | Abu | 2 | 1 |
| 105 | 3-C-4-MB | D-Leu | Abu | 2 | 1 |
| 106 | 3-TFMB | D-Leu | Abu | 2 | 1 |
| 107 | 4-C-3-Fb | D-Leu | Abu | 2 | 1 |
| 108 | 3-F-5-TFMB | D-Leu | Abu | 2 | 1 |
| 109 | 2-C-4-TFMB | D-Leu | Abu | 2 | 1 |
| 110 | 3-C-4-FB | D-Leu | Abu | 2 | 1 |
| 111 | 3-F-4-TFMB | D-Leu | Abu | 2 | 1 |
| 112 | 4-C-3-TFMB | D-Leu | Abu | 2 | 1 |
| 113 | 4-M-3-TFMB | D-Leu | Abu | 2 | 1 |
| 114 | 3-C-5-MB | D-Leu | Abu | 2 | 1 |
| 115 | 3-C-4-TFMB | D-Leu | Abu | 2 | 1 |
| 116 | 3-C-5-FB | D-Leu | Abu | 2 | 1 |
| 117 | 3,5-DCB | D-Leu | Ala | 2 | 1 |
| 118 | 3,5-DCB | D-Leu | Thr | 2 | 1 |
| 119 | 3-M-4-TFMB | D-Leu | Abu | 2 | 1 |
| 120 | 3-M-5-TFMB | D-Leu | Abu | 2 | 1 |
| 121 | 3-TFMB | D-Nle | Abu | 2 | 1 |
| 122 | 3-TFMB | D-Phe | Abu | 2 | 1 |
| 123 | 3-TFMB | D-Nlc | Thr | 2 | 1 |
| 124 | 3-TFMB | D-Phe | Thr | 2 | 1 |
| 125 | 3-TFMB | D-Nlc | Ala | 2 | 1 |
| 126 | 3-TFMB | D-Phe | Ala | 2 | 1 |

-continued

| Compound | $R^1$ | $R^3$ | $R^4$ | k | q |
|---|---|---|---|---|---|
| 127 | 4-TFMPA | D-Leu | Abu | 2 | 1 |
| 134 | 4-C-2-FB | D-Leu | Abu | 2 | 1 |
| 135 | 2-C-4-FB | D-Leu | Abu | 2 | 1 |
| 136 | 4-C-2-TFMB | D-Leu | Abu | 2 | 1 |
| 137 | 2-F-4-TFMB | D-Leu | Abu | 2 | 1 |
| 138 | 3-BPC | D-Leu | Abu | 2 | 1 |
| 141 | 3-TFMB | D-Leu | Abu | 3 | 1 |
| 142 | 4-BPC | D-Leu | Abu | 2 | 1 |
| 144 | 4-Cl-BP-4-C | D-Leu | Ala | 2 | 1 |
| 145 | 3-PP | D-Leu | Abu | 2 | 1 |
| 146 | 4-PB | D-Leu | Ala | 2 | 1 |
| 147 | 2,4-DCB | D-Leu | Abu | 2 | 3 |
| 148 | 2,4-DCPS | D-Leu | Abu | 2 | 1, |

or pharmaceutically acceptable salts thereof, wherein 4-BPC=4-biphenylcarboxyl, PA=phenylacetyl, 4-TFMPA=4-trifluoromethylphenylacetyl, 2-MB=2-methylbenzoyl, 3-MB=3-methylbenzoyl, 4-MB=4-methylbenzoyl, 3-F-4-MB=3-fluoro-4-methylbenzoyl, 4-C-3-MB=4-chloro-3-methylbenzoyl, 3-C-4-MB=3-chloro-4-methylbenzoyl, 3-C-5-MB=3-chloro-5-methylbenzoyl, 2-FPA=2-fluorophenylacetyl, 3-TFMB=3-trifuoromethylbenzoyl, 4-TFMB=4-trifluoromethylbenzoyl, 2-C-4-TFMB=2-chloro-4-trifluoromethylbenzoyl, 4-C-3-TFMB=4-chloro-3-trifluoromethylbenzoyl, 3-C-4-TFMB=3-chloro-4-trifluoromethylbenzoyl, 3-F-4-TFMB=3-fluoro-4-trifluoromethylbenzoyl, 3-F-5-TFMB=3-fluoro-5-trifluoromethylbenzoyl, 4-M-3-TFMB=4-methyl-3-trifluoromethylbenzoyl, 3-M-4-TFMB=3-methyl-4-trifluoromethylbenzoyl, 3-M-5-TFMB=3-methyl-5-trifluoromethylbenzoyl, 2-F-4-TFMB=2-fluoro-4-trifluoromethylbenzoyl, 4-C-2-TFMB=4-chloro-2-trifluoromethylbenzoyl, 3,5-BTFMB=3,5-bis(trifluoromethyl)benzoyl, 2,4,6-TMB=2,4,6-trimethylbenzoyl, 2,3-DMB=2,3-dimethylbenzoyl, 2,4-DMB=2,4-dimethylbenzoyl, 3,4-DMB=3,4-dimethylbenzoyl, 3,5-DMB=3,5-dimethylbenzoyl, 2-C-4-MB=2-chloro-4-methylbenzoyl, 4-EB=4-ethylbenzoyl, 4-IPB=4-Isopropylbenzoyl, 2,4-DCPA=2,4-dichlorophenylacetyl, 3,4-DCPA=3,4-dichlorophenylacetyl, 2-CPA=2-chlorophenylacetyl, 3-CPA=3-chlorophenylacetyl, 4-CPA=4-chlorophenylacetyl, 2-CB=2-chlorobenzoyl, 3-CB=3-chlorobenzoyl, 4-CB=4-chlorobenzoyl, 2,3-DCB=2,3-dichlorobenzoyl, 2,4-DCB=2,4-dichlorobenzoyl, 3,4-DCB=3,4-dichlorobenzoyl, 3,5-DCB=3,5-dichlorobenzoyl, 2,4,6-TCB=2,4,6-trichlorobenzoyl, 2-FB=2-fluorobenzoyl, 3-FB=3-fluorobenzoyl, 2-C-4-FB=2-chloro-4-fluorobenzoyl, 3-C-4-FB=3-Chloro-4-fluorobenzoyl, 3-C-5-FB=3-chloro-5-fluorobenzoyl, 4-C-2-FB=4-chloro-2-fluorobenzoyl, 4-C-3-FB=4-chloro-3-fluorobenzoyl, 2-MPA=2-methylphenylacetyl, 4-MPA=4-methylphenylacetyl, 3,4-DMPA=3,4-dimethylphenylacetyl, 3-BPC=3-biphenylcarboxyl, 4-C1-BP-4-C=4-chloro-biphenyl-4-carboxyl, 3-PP=3-phenylproponyl, 4-PB=4-phenylbutanoyl, 2,4-DCPS=2,4-dichlorophenylsulfonyl, Abu=2-aminobutyric acid, Phe=phenylalanine, Thr=threonine, Ala=alanine, Leu=leucine, and Nle=norleucine.

* * * * *